United States Patent [19]

Sundblom et al.

[11] Patent Number: 4,758,220
[45] Date of Patent: Jul. 19, 1988

[54] SURGICAL CASSETTE PROXIMITY SENSING AND LATCHING APPARATUS

[75] Inventors: Leif J. Sundblom, Castro Valley; Daniel D. Rogers, Berkeley, both of Calif.

[73] Assignee: Alcon Laboratories, Inc., Fort Worth, Tex.

[21] Appl. No.: 780,613

[22] Filed: Sep. 26, 1985

[51] Int. Cl.⁴ .......................................... A61M 31/00
[52] U.S. Cl. ...................... 604/65; 604/22; 604/31; 604/35; 604/67; 604/119
[58] Field of Search ............. 128/204.25; 604/22, 604/27, 30, 31, 33–35, 65, 67, 118, 114, 131; 422/64, 65, 100; 360/72.3; 73/44.2, 52

[56] References Cited

U.S. PATENT DOCUMENTS

| | | | |
|---|---|---|---|
| 3,028,750 | 4/1962 | Rondeaw | 73/49.2 |
| 3,269,800 | 8/1966 | Lukrec | 422/65 |
| 3,728,063 | 4/1973 | Langecker | 73/49.2 |
| 3,910,102 | 10/1975 | McLean | 73/49.2 |
| 3,985,508 | 10/1976 | Williams | 422/65 |
| 4,058,362 | 11/1977 | Gilford | 422/65 |
| 4,113,436 | 9/1978 | Werder et al. | 422/65 |
| 4,153,194 | 5/1979 | Leonard, Jr. | 228/29 |
| 4,236,825 | 12/1980 | Gilford et al. | 423/63 |
| 4,276,048 | 6/1981 | Leaback | 422/65 |
| 4,296,070 | 10/1981 | Montalto et al. | 422/64 |
| 4,361,253 | 11/1982 | Flynn et al. | 422/100 |
| 4,378,034 | 3/1983 | Albertson | 73/49.2 |
| 4,387,076 | 6/1983 | Cabrera et al. | 422/65 |
| 4,395,258 | 7/1983 | Wang | 604/65 |
| 4,462,249 | 7/1984 | Adams | 73/49.2 |
| 4,536,807 | 8/1985 | Kato et al. | 360/72.3 |

FOREIGN PATENT DOCUMENTS

| | | | |
|---|---|---|---|
| 565999 | 8/1975 | Switzerland | 73/49.2 |
| 717596 | 2/1980 | U.S.S.R. | 73/52 |

OTHER PUBLICATIONS

Grieshaber brochure (rotatable intraocular microscissors).
Grieshaber brochure (membrane pealer and cutter).
United Surgical Corporation brochure, Phacotron Plus TM.
Surgical Design brochure, Ocusystem TM.
CooperVision Brochures: CooperVision System Six TM; CooperVision Cavitron/Kelman Model 6500PIS and Model 7500 I/A System Three.
CooperVision Brochure, Cavitron/Kelman Phacoemulsifier/Aspirator Model 8001 and Model 9001.
Two Brochures on the CooperVision Ocutome Disposable Vitrectomy Probe and the CooperVision Anterior Pack.
Site TXR System 2000 Brochure.

*Primary Examiner*—Lee S. Cohen
*Assistant Examiner*—David Shay
*Attorney, Agent, or Firm*—Ron Fish

[57] ABSTRACT

There is disclosed herein a system for providing control of multiple functions needed to perform eye surgery. A microprocessor based system controls a vacuum generation system using venturis and linear valves and a pneumatic system for driving vitrectomy probes and pneumatic scissors in either a variable frequency, multicut mode or a proportional cut mode where the cutting pressure is proportional to the position of a foot operated position sensor. The frequency of the vitrectomy probe cutting action can also be controlled and the level of vacuum can be controlled from a foot operated position sensor which can also be used to turn on or off a fragmentation device. The footswitch can also be used to turn irrigation fluid on or off, and the flow rate can be controlled from a control on the front panel. By making a certain foot motion in any certain aspiration modes, reflux of the aspiration line can be controlled. The vacuum level is continuously monitored over all aspiration conditions and adjusted to stay as close as possible to the desired vacuum level. A cassette proximity sensing system senses the presence of a cassette, and aids the user in drawing in and latching the cassette. The vacuum integrity of the cassette is automatically checked by the microprocessor each time one is drawn into the machine. The microprocessor also monitors the cassette for fullness an initiates a transfer to empty one bottle of the cassette into another bottle for storage when the first bottle becomes full. A back-up system checks the accuracy of cassette liquid level sensing apparatus by double checking for liquid in the line leading to the vacuum generation system. If water is detected, a fluid transfer from one bottle of the cassette to the other is initiated.

9 Claims, 24 Drawing Sheets

VAC.
LINE TO TOOL

SURGICAL CASSETTE PROXIMITY SENSING AND LATCHING APPARATUS

BACKGROUND OF THE INVENTION

The invention pertains to the field of surgical instrument systems for supporting eye surgeons in performing eye surgery on the human or an animal eye.

Eye surgeons who perform cataract removal and vitrectomy operations as well as other procedures need surgical instruments which fulfill certain basic needs of the surgeon. The most common of these needs is to cut and remove tissue. Other needs include introducing ultrasonic energy into certain parts of the eye to break up certain undesirable tissue formations, irrigation of the portion of the eye being operated upon, transmitting light into the area of the eye being operated upon, and control of surgical scissors. It is convenient for the surgeon to have an instrument which can perform all these functions under control of the surgeon in the operating room.

Various surgical instruments exist which support various of these functions. However there are few surgical instruments that can perform all these functions. Further, these functions can be done in many different ways, some of which are better than others. For example, it is useful for the surgeon to have vacuum at his disposal to aspirate cut-away tissue and to have complete control of the maximum level of vacuum and the actual level of vacuum in the system under various aspiration conditions. Further, it is useful for the surgeon to be able to request more or less vacuum without having to use his hands or tell another person how much vacuum he wants. If the surgeon accidently aspirates something he or she did not mean to aspirate with the instrument, it is useful to be able to cause a reflux of the system to force the item out of the aspiration line.

Many prior art systems use peristaltic pumps or diaphragm pumps to generate the desired vacuum. These pumps are sometimes noisy and are slow to generate the desired vacuum level. Further, it is desirable to have a fast response time for changes in the desired vacuum levels, and for the system to display both the actual vacuum and the desired maximum vacuum. It is also useful for the system to automatically monitor the actual vacuum level under all aspiration conditions and to automatically adjust it to match the requested vacuum level such that the surgeon does not have to request more vacuum when vacuum in the system falls caused by varying aspiration conditions. Few prior art systems, if any, offer all these features.

It is also desirable for the surgeon to have an instrument which gives him powered surgical scissors which can cut tissue in several modes. A multicut mode where the scissors blades automatically open and close at a frequency controlled by the surgeon is useful. It is also useful to have a mode where the scissors blades close in proportion to the amount of pressure the surgeon places on a foot pedal. Such a scissors mechanisim should be light, small and simple and not pose any danger of electrical shock to the patient or electrical current leakage into the eye in the case of a worn or defective instrument. Few, if any, prior art systems offer all these features.

Further, it is useful for the instrument to be able to support an ultrasonic fragmentation device such that the surgeon can turn such an instrument on and off during the course of a surgery to break up tissue formations ultrasonically.

It is also frequently necessary during posterior work in the eye, i.e., behind the lens, to transmit light into the eye so that the surgeon can see effectively. The prior art instruments sometimes have light probes which carry light from a source in the instrument into the eye. However, the light sources are frequently quite close to the end of the light probe, and, as a result, the light probes get hot enough to burn the fingers of a surgeon or nurse who attempts to remove the probe before it has cooled down.

Few if any prior art systems offer all the useful features mentioned above, and few solve all the problems posed above.

SUMMARY OF THE INVENTION

The invention is a cassette-handling system for sensing the proximity of a cassette for storing aspirated material in a system for support of eye surgeons in performing eye surgery and for drawing the cassette into a sealed relationship with the vacuum seals of the machine using the machine's own power. This makes the insertion of the cassette substantially easier than machines where manual insertion is used since great physical power is required to push a cassette into its receptacle and to adequately compress the vacuum seals to have a positive vacuum seal.

A positive cassette latching mechanism is employed wherein a microprocessor senses the proximity of the cassette by reading a microswitch mounted such that when a cassette is pushed partially in, the switch is activated. When this fact is sensed, the microprocessor activates a solenoid-operated valve to gate air to a piston which activates a latch mechanism to engage a portion of the cassette and pull it into sealing engagement with the rest of the unit. When the operator elects to remove a cassette, a switch on the front panel is pushed, and the microprocessor senses this fact and vents the pressure in the first piston to atmosphere to unlock the cassette and activates another solenoid-operated valve to gate air to a piston which pushes the cassette free.

The microprocessor also tests the integrity of the vacuum seal after the cassette is latched into position. This is done by activating a vacuum generation system and gating the vacuum through to the cassette. A vacuum sensor coupled to the vacuum system which includes the cassette and the vacuum seals between the cassette and the rest of the system is then read to determine the level of vacuum that is reached in the cassette. If the vacuum does not reach a certain vacuum level within a specified time, then one failure is recorded and the vacuum generation process is tried again. If the cassette or vacuum seal fails again to allow vacuum to reach the specified level within the specified time, a second failure is recorded, an error message is displayed, and the second part of the vacuum integrity test is not reached. If the first part of the vacuum integrity test is passed either the first or second time it is attempted, then the second part is performed. This second part involves waiting a certain time with the cassette evacuated. After the waiting period, the vacuum level in the cassette is read again and subtracted from the constant representing the vacuum level reached in the first part of the test. If the vacuum level has dropped more than a certain amount, the cassette or seals have a leak which is too large, and an error message is displayed.

DETAILED DESCRIPTION OF THE PREFERRED EMBODIMENT

Figure 1A:
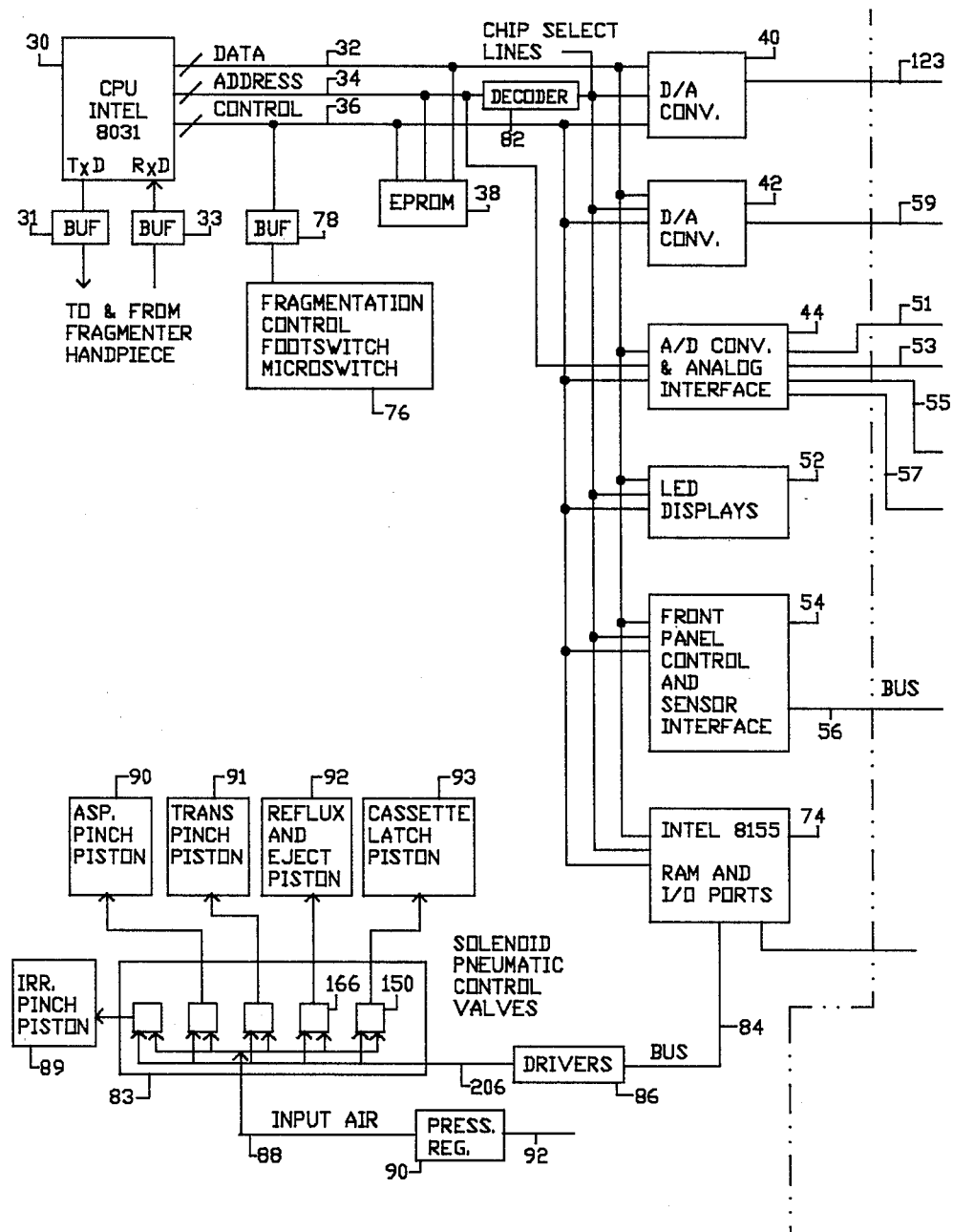
FIGS. 1A and B is a block diagram of the apparatus of the system comprising the invention.
Figure 1B:
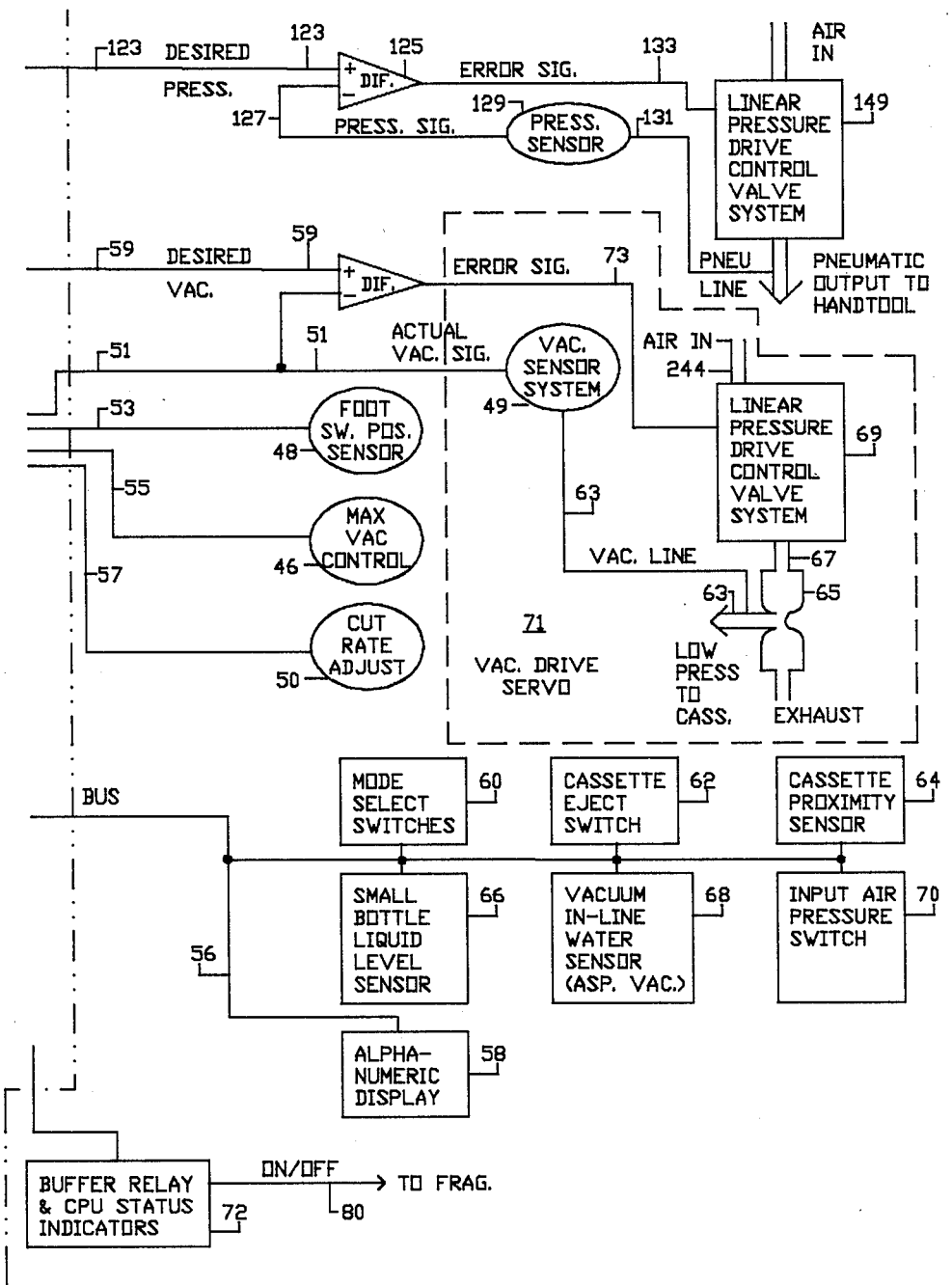

Referring to FIG. 1 there is shown a block diagram of the invention. A CPU 30 acts as the central controller of the system, and is coupled to the units it controls by data, address and control buses 32, 34 and 36 respectively. In the preferred embodiment, the CPU 30 is an Intel 8031 microprocessor. The programs which controls operations of the microprocessor and all the units to which it is coupled to implement the process of the invention are included herewith as Appendices A, B and C. These appendices represent three different embodiments of the invention. The microcode of the particular embodiment of the invention is stored in a programmable read-only memory (PROM) 38 which the microprocessor 30 accesses for instructions to carry out the process of the invention. Appendix C represents an embodiment of the invention which implements all the features to be described herein. Appendix A represents an embodiment which implements all the features of the Appendix C embodiment except the reflux feature. Appendix B represents an embodiment which implements all the features of the embodiment of Appendix C except the light source and insulation system for the light probe and except for the pneumatically driven scissors. For simplicity's sake the following description will be directed to the embodiment of Appendix C since such a description also describes the processes implemented in the other embodiments and the apparatus used to carry them out.

In other embodiments other microprocessors or even minicomputers could be used with suitable adjustments in the object code of Appendices A, B and C to the machine language used by the particular computer selected. Generally, the microprocessor 30 controls a vacuum generation system, a pneumatic pressure system and various solenoid operated valves, relays, displays and indicators to implement the processes carried out in the various modes in which the machine operates. Interface with the user is provided through front panel control switches, potentiometers, a foot switch and a display.

The microprocessor 30 is coupled to the digital-to-analog converters 40 and 42 to control the pneumatic and vacuum systems respectively. Details of the operation of these systems will be given below.

An analog-to-digital converter 44 is used by the microprocessor to convert analog data from various sensors and controls indicating conditions the machine is controlling to digital data the microprocessor can read. To control the vacuum and pneumatic systems, certain information must be supplied to the microprocessor 30 by the user.

For example, in the irrigation and aspiration mode, the vitrectomy mode and the fragmentation mode, vacuum is supplied by the system to a hand tool used by the surgeon to aspirate tissue and irrigation fluids and body fluids from the area being operated upon. There are two user inputs to control this vacuum generation process. One is the maximum vacuum that the surgeon desires the machine to generate, and the other is the desired vacuum at any particular time. The maximum vacuum is set by the surgeon by a potentiometer or other control 46 on the front panel. The actual vacuum or the vacuum desired by the surgeon at any particular time is read from a footswitch position sensor 48 which the surgeon pushes up and down to signal his desire for more or less vacuum. The footswitch position sensor is also used to control the frequency of blade closure, i.e., the cut rate in the multicut scissors driving mode. Details on how the footswitch is read will be given below in the description of the vacuum control system.

In the vitrectomy mode, a cutting probe of a structure well known in the art is pneumatically driven with pulses of pressurized air. The frequency of these pulses is controlled by a cut rate adjust control 50, which can be a potentiometer. The cut rate adjust control 50 is also used to control the flow of aspiration fluid in the irrigation and aspiration mode such that a variable flow can be achieved. An address supplied by the microprocessor to the A/D converter 44 tells it which of these analog inputs connected to multiple channel inputs of the A/D converter to select and convert to a digital number.

A display 52, which is comprised of light emitting diodes in the preferred embodiment but which can be any type of display, is used by the microprocessor 30 to display the cut rate in the vitrectomy mode in the form of a bar graph. The display, in the preferred embodiment, is comprised of a plurality of LED's arranged in a line. The relative cut rate is displayed as the number of LED's which are lit. Other formats for the display of this information are possible and will be apparent to those skilled in the art.

A front panel control and sensor interface 54 is coupled by a bus 56 to several switches and an alphanumeric display 58. The alphanumeric display 58 is used by the microprocessor 30 to display various items of information such as the mode in which the machine is currently operating, the actual vacuum, maximum vacuum desired and other messages. Several mode select switches 60 on the front panel are used by the surgeon to select which of the several modes in which the machine is to operate. There are five main modes in which the machine operates with the irrigation and aspiration mode having three submodes. Mode selection can be by toggling three switches as in the preferred embodiment, by rotary switch or by a separate switch for each mode. The details on how to implement this mode selection will be apparent to those skilled in the art.

A cassette eject switch 62 is used by the surgeon when the cassette (not shown) becomes full and must be removed. When this switch is pushed, the microprocessor 30 causes certain solenoid operated valves to be operated which unlatch and eject the cassette from its chamber in the front panel. A cassette proximity sensor 64 in the form of a microswitch is mounted in the cassette chamber such when a new cassette is pushed part way into the chamber, the switch changes states. This change is read by the microprocessor, which causes certain solenoid operated valves to be operated such that a mechanism is activated which engages and pulls in the cassette to a locked position in its chamber.

The cassette, as will be seen in connection with the discussion of another figure herein, has two bottles for storage of aspirated material. Material is aspirated into a small bottle until it is full. The fact that the small bottle is full is sensed by the microprocessor 30 through a small bottle liquid level sensor 66. This sensor is a pair of wires protruding through the top of the small bottle in the preferred embodiment. When liquid reaches the top of the bottle, current flows between the wires which is sensed and which signals the microprocessor that the small bottle is full. The microprocessor then initiates a transfer of the aspirated liquid from the small bottle to the large bottle in a manner which will be described later.

The manner in which this sensing is done is as follows. In the preferred embodiment, the irrigation solution which is aspirated is a saline solution and is relatively conductive. When this solution reaches the wires in the top of the small bottle, an appreciable current flows. A high impedance voltage source is connected to one of the pins and and the other pin is grounded. A comparator having a reference voltage coupled to one of its inputs has its other input coupled to the non-grounded pin. Normally the input coupled to the non-grounded pin will be a logic one until water reaches the wires. When that happens the pin connected to the comparator goes to logic zero, and the comparator changes states. Since the output of this comparator is frequently polled, the microprocessor senses the change, and initiates a transfer.

A vacuum line water sensor 68 is also included for protection of the machine in case the above described fluid transfer mechanism fails. It is possible that the fluid transfer mechanism may fail for some reason such as corroded wires in the top of the small bottle. If this happens, the small bottle can fill up, and water can enter the vacuum line to the vacuum generating apparatus. This is an undesirable condition, and the machine must be shut down if it occurs to prevent damage to the internals of the machine. The vacuum line water sensor 68 senses the presence of solution in the vacuum line in the manner described above for the small bottle liquid level sensor 66. When the microprocessor senses this condition, the machine is shut down until the condition is cleared.

An input air pressure switch 70 monitors the pressurized air input to the system to provide a warning if the input air pressure falls below a certain minimum air pressure acceptable for machine operation.

A buffer unit and relay 72 provide on/off control for a known fragmenter handpiece. The presence of the fragmenter handpiece and cable connecting the system to this device is tested for by the microprocessor 30 by sending a signal to the fragmenter handpiece out the serial transmit data port through a buffer 31. If the fragmenter handpiece is present, this signal returns on the cable to the microprocessor 30 receive data port through a buffer 33. Such fragmenter handpieces use ultrasonic sound transducers to generate sound waves which are used to break up various tissue formations which the surgeon wishes to remove such as cataracts. Such ultrasonic transducers must be supplied with power and provided with on/off control from the host system. The invention supplied power and provides this on/off control through the relay unit 72. The unit 72 consists basically of a latch and relay driver which is addressed through a RAM and I/O port unit 74. The RAM and I/O port unit 74 has a scratchpad RAM unit in which the microprocessor 30 can store values to control certain aspects of the machine operation such as the desired scissors pressure, and the error number if any error condition occurs. The microprocessor has internal RAM also which is used to store various initialization values for the interrupts. Certain interrupt routines are used in controlling the pneumatic and vacuum systems. Each time a new mode of operation is entered, these interrupts are initialized for that particular mode, and these initialization values are accessed from the internal RAM to initialize the routine. These initialization values could be stored in the external RAM also, but this is not preferred because the delays of bus access would slow down operations compared to retrieving these values from internal RAM.

The unit 74 also has I/O ports which can be individually addressed by the microprocessor when the microprocessor wishes to write data to or read data from a particular peripheral. One of these I/O ports is coupled to the buffer and fragmentation control relay unit 72. When the surgeon wishes to turn on the fragmentation device, he kicks the footswitch either left or right depending upon which way is assigned to be the "on" direction. A microswitch in the footswitch is actuated by this action and changes states. This microswitch 74 is coupled to pins 4 and 5 of the microprocessor through a buffer 78. When the microprocessor polls this footswitch and determines that fragmentation is desired, it addresses the particular I/O port coupled to the buffer and fragmentation control relay unit 72 and writes data into the latch and buffer in the unit 72 indicating that fragmentation is desired. This data is then used to control relay driver circuitry in the unit 74 which activates a relay coupled to the bus 80. This bus provides a signal to the fragmentation transducer handpiece that fragmentation is desired. Although power is not supplied on the bus 80, in some embodiments it could be so supplied.

The microprocessor 30 addresses the various peripheral units using the address bus 34 and a decoder 82. When a particular unit is to be addressed for reading or writing, the address of that unit is placed on the address bus 34 and the decoder 82 decodes the address. The decoder 82 then activates a chip select line connected to the chip enable input of a particular peripheral unit. That unit then activates its data ports and control ports from the tri-state condition so as to be able to red data from or send data to the microprocessor 30 on the data bus 32 and the read the status of various control signals on the control bus 36.

The I/O ports in the RAM and I/O unit 74 are also individually coupled to several solenoid operated pneumatic control valves 83 by a bus 84 and some solenoid drivers 86. These solenoid operated valves 83 gate pneumatic air pressure on an input air line 88 to one of a number of pneumatic pistons 89–93 which perform various fluid valve and latching functions. These functions will be explained more fully in connection with the discussion of the pneumatic control system below. Each of the solenoid operated valves can be individually actuated by the microprocessor 30 through the RAM and I/O port unit 74, the bus 84 and the drivers 86. A pressure regulator 90 insures that the input air pressure on the line 88 remains stable despite fluctuations of the air pressure on the line 92.

VACUUM CONTROL SYSTEM

The system of the invention operates in several modes. Some of these modes require the generation of vacuum for transmission to a hand tool for aspiration of cut tissue or irrigation fluid from the area in which the surgeon is working. The surgeon controls the level of vacuum desired by means of the footswitch position sensor 48 which is read by the microprocessor 30. The microprocessor addresses the A/D converter 44, and reads its digital output word. This word is a digital representation of the relative displacement of the footswitch position sensor relative to its end stops. The microprocessor 30 generates this word by reading the setting of the maximum vacuum control 46 by addressing the A/D converter 44, and selecting the maximum vacuum control as the desired analog input to convert to a digital value. As can be seen from FIG. 1, the A/D converter is connected to several analog inputs, i.e., from the vacuum sensor 49 on the line 51, from the footswitch position sensor 48 on the line 53, from the max vacuum control 46 on the line 55, and from the cut rate adjust knob 50 on the line 57. The particular input selected depends upon the state of three bits of the address bus.

After the maximum vacuum control 46 and the foot switch position sensor 48 have been read, the desired actual vacuum level is derived by the microprocessor by multiplying the maximum vacuum setting by the fraction of the total possible displacement the foot switch had when it was read. The resultant digital number is sent to the D/A converter 42 by addressing it using decoder 82 and writing the data into the input latch of the converter 42. The foot switch position sensor 48 and maximum vacuum control 46 are polled periodically by the microprocessor through an interrupt service routine performed every time a timer internal to the microprocessor times out. Thus the desired vacuum digital word sent to the D/A converter 42 can be changed at least as often as the vacuum control interrupt occurs if the foot switch position has changed in the interim. In the preferred embodiment, this interrupt occurs 100 times every second.

The desired vacuum word is converted to an analog signal which is transmitted on a line 59 to the non-inverting input of a differential amplifier 61. The differential amplifier 61 has its inverting input coupled to the electrical vacuum signal on the line 51 from a vacuum sensor 49. This sensor is pneumatically coupled by a line 63 to the throat of a venturi 65. The venturi serves to convert air flowing under pressure through it to subatmospheric pressure. The pressurized air input or main air channel of the venturi 65 is coupled by an air line 67 to a solenoid operated linear valve 69. Such valves are known in the art, and ar manufactured by Precision Dyanmics, Inc. under the Model Number A2011-S51. Fundamentally the linear valve control system 69 works as follows.

Figure 2A:
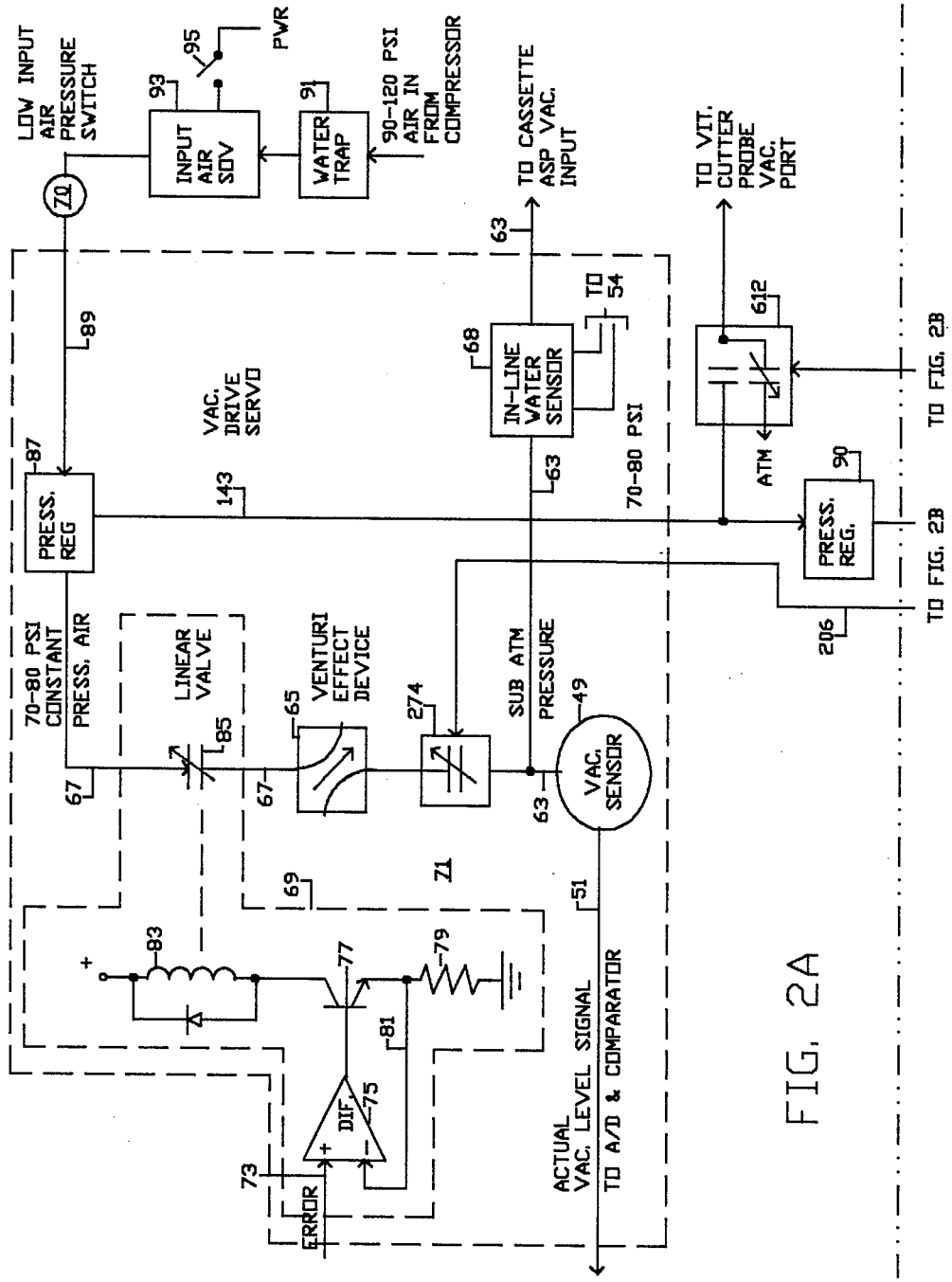
FIGS. 2A and B is block diagram of the pneumatic and vacuum systems and portions of the vacuum and pneumatic control systems.
Figure 2B:
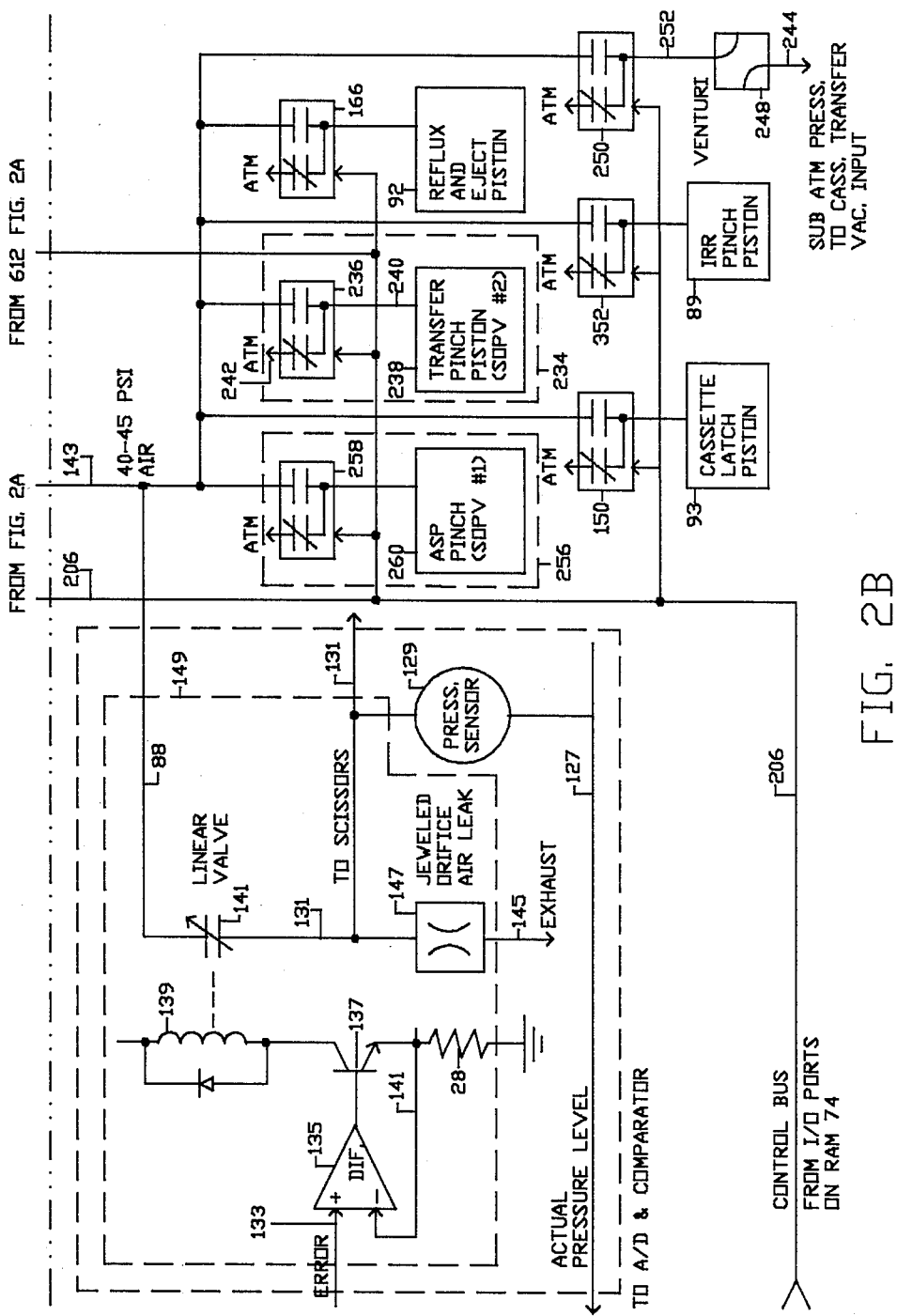

Referring to FIG. 2, there is shown a more detailed diagram of the pneumatic and vacuum system of the invention. The vacuum drive servo system 71 outlined in phantom in FIG. 1 is also outlined in phantom in FIG. 2 with the reference numeral 71. The difference amplifier 61 in FIG. 1 subtracts the actual vacuum signal on the line 51 from the analog desired vacuum signal on the line 59 and generates an analog error signal on a line 73. The magnitude of this error signal is indicative of how much difference there is between the desired vacuum and the actual vacuum being generated by the system. This analog voltage must be converted to a current proportional to the magnitude of the error voltage. This is done by another difference amplifier 75, a driver transistor 77 and an emitter feedback resistor 79. The output of the difference amplifier 75 drives the base of the transistor 77 whose emitter current flows through the resistor 79. A feedback voltage from the high side of the resistor 79 is fed back into the inverting input of the amplifier 75 on a line 81 and is subtracted from the error voltage on the line 73. The difference between these two voltages on lines 73 and 81 is converted to base drive for the transistor 77 thereby converting the difference voltage into collector current which flows through the solenoid coil 83 of the linear valve system 69. The magnetic flux caused by this current opens a linear valve portion 85 in proportion while the intensity of the magnetic flux. The valve portion modulates the flow of pressurized air through the valve on the pneumatic line 67. This pressurized air is regulated at a pressure of from 70–80 psi by a pressure regulator 87. Input to the pressure regulator 87 is a pneumatic line 89 which carries pressurized air from a compressor at 90–120 psi through a water trap 91 and an input air solenoid operated valve 93. The water trap prevents water from entering the pneumatic system, and the solenoid operated valve 93 allows the input air supply to be controlled such that the pressurized air is gated into the system when the power is applied to the system as symbolized by the switch 95.

Figure 3:
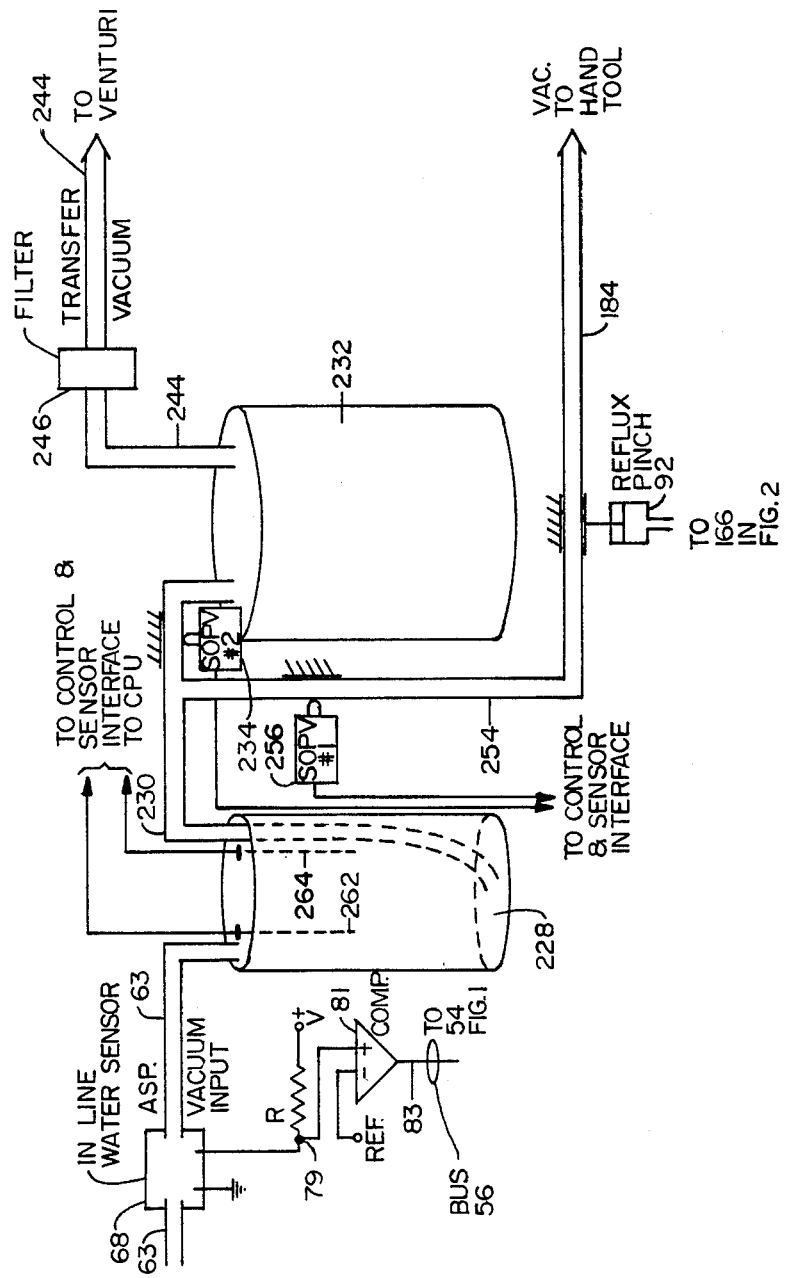
FIG. 3 is a block diagram of the cassette liquid-handling system showing the fluid flows, vacuum lines and the valves used in controlling fluid flow.

The solenoid operated valve 85 thereby converts the analog error signal on the line 73 into an air flow having a flow rate which is related to the magnitude of the error signal. When the error signal is large, the flow of air is increased. This air flows through a venturi effect device such as is described in U.S. Pat. No. 3,474,953. This device converts the air flowing under pressure into a subatmospheric pressure in the throat of the device by the venturi effect. This subatmospheric pressure is piped on a pneumatic line 63 to the cassette collection device through an in line water sensor 68. The in line water sensor 68 functions to detect the presence of fluid in the vacuum line 63. This condition can occur if the cassette becomes full and the mechanism in the cassette to detect this full condition fails. When such a failure occurs, fluid can be sucked into the vacuum line 63. Generally this fluid is a saline solution used to irrigate the area where the surgeon is working, and it is both conductive and corrosive. If this fluid gets into the machine through the venturi throat, it can corrode connections and other apparatus in the machine. To prevent this, the in line water sensor 68 is provided. This sensor has two gold plated electrodes which are not subject to corrosion. When fluid is present in the line 63, current can flow between these electrodes which can be detected. This detection is accomplished by connecting a voltage source to one of the wires through a resistor, and connecting the other wire to ground. The non-inverting input of a comparator is then connected to the wire which is coupled to the voltage source. The inverting input of the comparator is then connected to a reference voltage, preferably one between the voltage V applied to one of the wires and ground. This arrangement is shown in FIG. 3 which shows the details of the cassette vacuum system and control valves. When fluid is aspirated into line 63 and enters the in line water sensor 68, it collects around the wires and forms a conductive path between the wire to which the voltage V has been applied. This causes the voltage at the node 79 to fall to ground potential or slightly above. A comparator 81 senses this change, and its output line 83 changes states. This output line 83 is coupled by the bus 56 to a latch in the front panel control and sensor interface 54 in FIG. 1 and sets a flag. This latch is polled by the microprocessor from time to time, and when the flag is set, the microprocessor shuts the machine down to prevent damage.

Returning to consideration of the vacuum control system, the subatmospheric pressure on the line 63 is coupled to the vacuum sensor 49 through a solenoid operated valve 274, the purpose of which will be explained in connection with the discussion of FIG. 9A. The solenoid operated valve 274 is controlled by the microprocessor 30 through a connection to the control bus 206 and remains open for all purposes relevant here thereby allowing vacuum generated in the venturi 65 to be communicated to the vacuum line 63. The vacuum sensor 49 converts the vacuum level into an electrical signal on the line 51. This "actual" vacuum level signal is coupled to the inverting input of the differential amplifier 61 so as to change the error signal on the line 73. When the microprocessor 30 first requests a certain vacuum level, the actual vacuum signal on the line 51 is zero and the error signal is large. As the differential amplifier 75 and the transistor 77 convert this error signal into increased current through the coil 83, and increased air flow through the venturi 65, the vacuum level begins to increase, i.e., the pressure in line 63 becomes increasingly lower than atmospheric pressure. The vacuum sensor 49 converts this change to higher vacuum, to an increase in voltage on the line 51. The rise in voltage on the line 51 causes the error signal on the line 73 to decrease. The tendency of the system is to reduce the error signal to near zero, but a zero error signal can never be actually obtained as long as the footswitch is depressed. This is because the aspiration tool is always sucking, but vacuum conditions are changing as material is sucked into the tube in varying amounts. When material is sucked into the tube in such quantities as to partially occlude the tube, the vacuum rises and the error signal changes in the downward direction. When no material or little material is being sucked into the tube, the vacuum falls, and the error signal rises. The feedback system responds to these changes in actual vacuum by changing the position of the linear valve to change the air flow rate. The direction of the change is such as to change the vacuum level back towards the desired value. The overall effect is to tend to stabilize the vacuum level at the level requested by the surgeon through the footswitch. To the surgeon, the actual vacuum level seems to change with his manipulation of the footswitch.

Figure 4A:
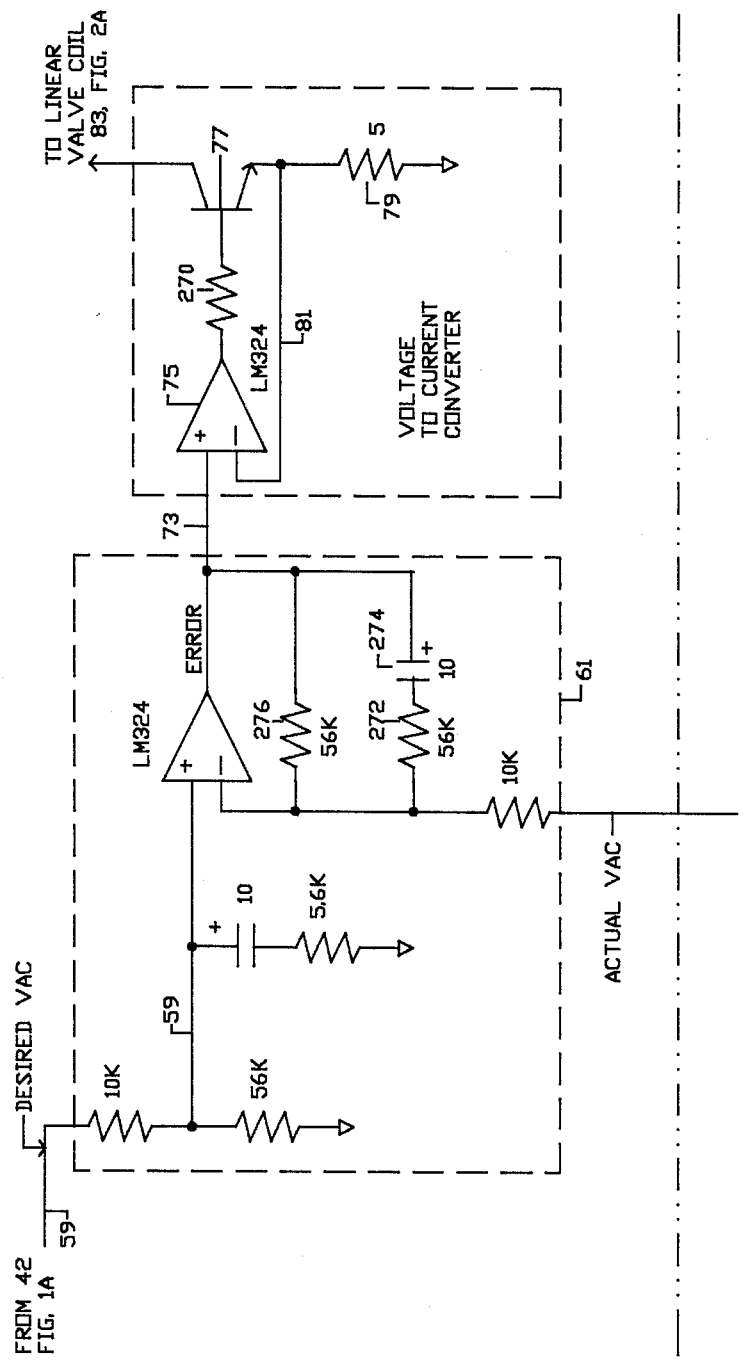
FIGS. 4A and B is a detailed schematic diagram of the vacuum control system electronics.
Figure 4B:
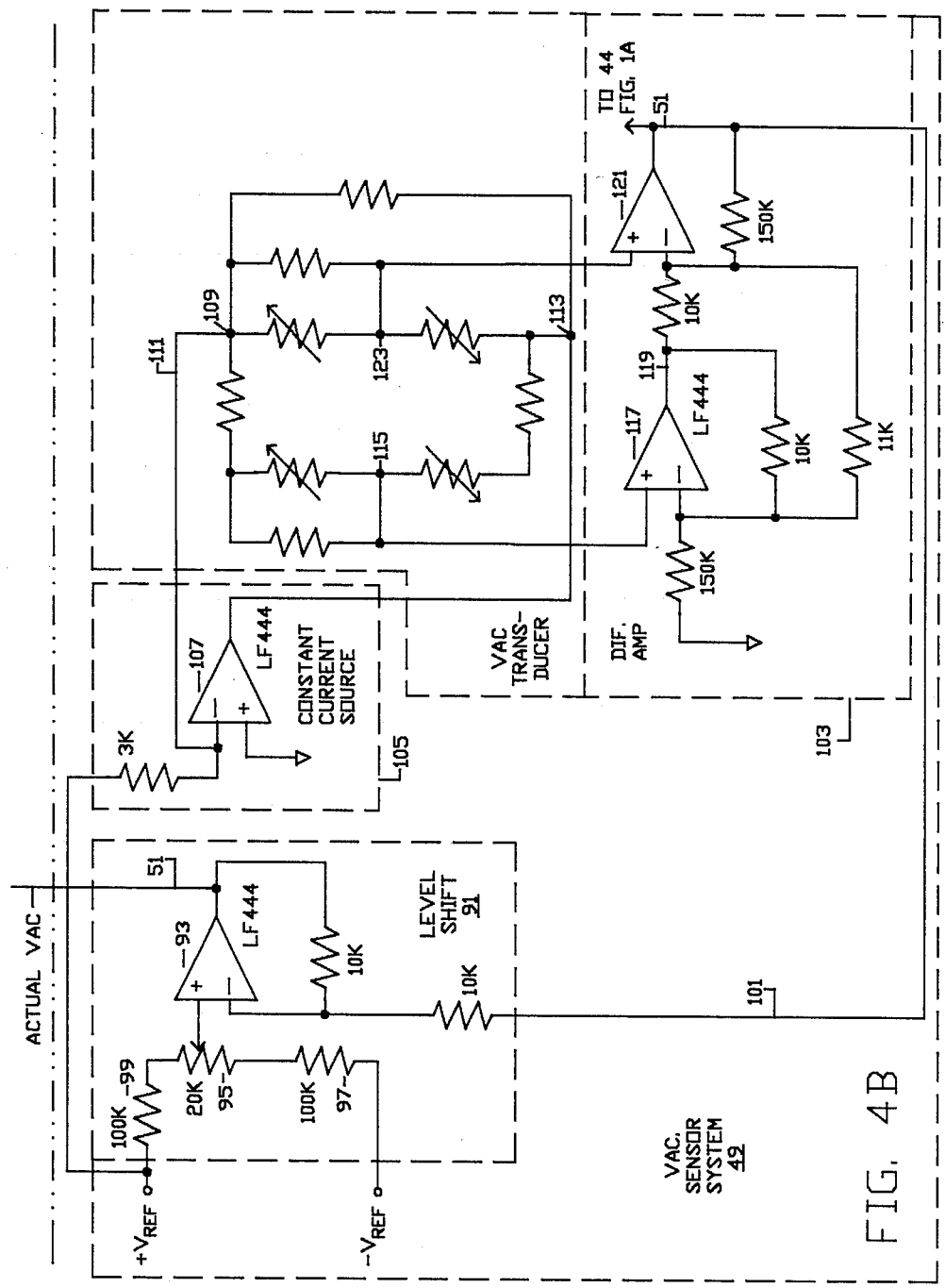

Referring to FIG. 4, there is shown a schematic diagram for the analog feedback system for controlling the actual vacuum signal to the level of the desired vacuum requested by the microprocessor shown in block diagram form in FIGS. 1 and 2. The desired vacuum level comes in on line 59 in the form of an analog signal from the digital-to-analog converter 42. A portion of this signal is applied to the non-inverting input of a differential amplifier 85 which, together with all the associated gain and bandwidth setting components inside the phantom line, performs the function of the differential amplifier system 61 in FIG. 1 to generate the error signal on the line 73. The feedback resistors 276, 272 and a capacitor 274 establish a non-linear gain for the amplifier 61 over the bandwidth of the system. The transfer function of the system has a gain of approximately 10 from D.C. to approximately 15-20 hertz. The gain then begins to roll off at approximately 10 db/decade until it reaches a value of approximately 0.5 at 200 hertz. The gain remains at that level until parasitic capacitances cause a rolloff to zero.

The error signal on the line 73 is coupled to the voltage to current converter comprised of the differential amplifier 75 and the transistor 77 which functions as described above.

The actual vacuum feedback signal on the line 51 is coupled to the inverting input of the differential amplifier 61 through a level shifter 91. This level shifter has an adjustable reference voltage applied to the non-inverting input of a differential amplifier 93. This reference voltage is taken from the wiper of a potentiometer 95 in a voltage divider comprised of resistors 97 and 99 coupled between positive and negative terminals of a voltage reference source (not shown). The actual vacuum signal from the vacuum sensor 49 is coupled to the inverting input of the differential amplifier 93. This signal, on a line 101 is taken from the output of a high gain differential amplifier 103 which senses the actual vacuum condition by interpreting the voltages on a resistor bridge inside the vacuum transducer. The vacuum transducer is a resistor bridge coupled to a constant current source 105. The constant current source is comprised of a differential amplifier with its inverting input coupled to a reference voltage and its non-inverting input coupled to ground. The output of the differential amplifier 107 is coupled to one node of the resistor bridge of the vacuum transducer. The top node 109 of the bridge is coupled to the positive voltage reference voltage by the line 111. This line serves as a source of negative feedback voltage to stabilize the current sunk by the differential amplifier from the node 113 since varying current sunk from the bride will change the voltage at the node 109.

Changing vacuum conditions, changes the voltage at a node 115 in the bridge by virtue of the changing values of the resistors comprising the bridge. This voltage is coupled to the non-inverting input of differential amplifier 117. This amplifier amplifies the voltage at the node 115 and presents the resultant output voltage on an output 119 which is coupled to the inverting input of another differential amplifier 121. The non-inverting input of this amplifier 121 is coupled to a node 123 which is located in the bridge such that its voltage also varies with changing vacuum conditions. The result of this arrangement is that the voltage at the node 115 is subtracted from the voltage at the node 123. The difference is the actual vacuum signal on the line 101 which is level shifted and coupled to the differential amplifier 61 on the line 51.

PNEUMATIC PRESSURE CONTROL SYSTEM

Referring again to FIGS. 1 and 2, there is shown a block diagram of the pneumatic pressure control system. The system has several modes in which greater than atmospheric pneumatic pressure is supplied and controlled by the system to hand held cutting tools used by the surgeon. For example, in the scissors proportional cut mode, pneumatic pressure in proportion to the position of the footswitch is applied to a pneumatically driven scissors. In the scissors multicut mode, a pneumatic waveform in the form of a triangular having a frequency proportional to the position of the footswitch 48 is transmitted to the pneumatically operated scissors. The pneumatic pressure control system operates somewhat like the vacuum control system in that the mode switches 60 are consulted as to the mode desired by the operator and then the footswitch is read. After the footswitch is read and a calculation of the cut rate or desired pressure is made, the microprocessor writes a digital word to the D/A converter 40 in FIG. 1. This word is converted to an analog signal on the line 123 which is coupled to the non-inverting input of a differential amplifier 125. The inverting input of this differential amplifier 125 is coupled to an actual pressure signal on a line 127. This signal is generated by a pressure sensor 129 which has a pneumatic input coupled to a pneumatic pressure line 131 which can be coupled to a hand held pneumatically driven scissors. The differential amplifier 125 subtracts the actual pressure signal on the line 127 from the desired pressure signal on a line 123 to generate an error signal on a line 133. Referring to FIG. 3, this error signal is applied to the non-inverting input of another differential amplifier 135 which is analogous in function to the amplifier 75. The output of this amplifier is coupled to the base of a transistor 137 which has an emitter feedback resistor 139. The emitter node is coupled by a line 141 to the inverting input of the differential amplifier 135, and the combination of the amplifier 135, the transistor 137 and the resistor 139 function in the same way as in the vacuum control system to convert the error voltage on the line 133 to a current flowing in the coil 139 of a solenoid operated linear valve 141. This current is a function of the error voltage and sets up a magnetic flux which causes the valve portion 141 to modulate the flow of pressurized air on a pneumatic line 88 to the pneumatic line 131 in accordance with the level of the error signal on the line 133. The pneumatic line 88 carries pressurized air at a regulated pressure of from 40 to 45 psi established by a pressure regulator 90 which is coupled by a pneumatic line 143 carrying pressurized air from the pressure regulator 87 at a pressure from 70–80 psi. The modulated air flow on the pneumatic line 131 is coupled to an exhaust 145 (to atmosphere) by a jeweled orifice 147. The jeweled orifice converts the modulated flow into a modulated pressure by virtue of the controlled leakage of pressurized air through a constant diameter port to atmosphere. The error signal generation circuitry and feedback system just described is similar in construction and operation to the vacuum control system described above, and will not be further described. The elements inside the phantom box 149 in FIG. 2 together comprise the linear pressure drive control valve system 149 in FIG. 1.

CASSETTE PROXIMITY SENSING AND LATCHING MECHANISM

Figure 5:
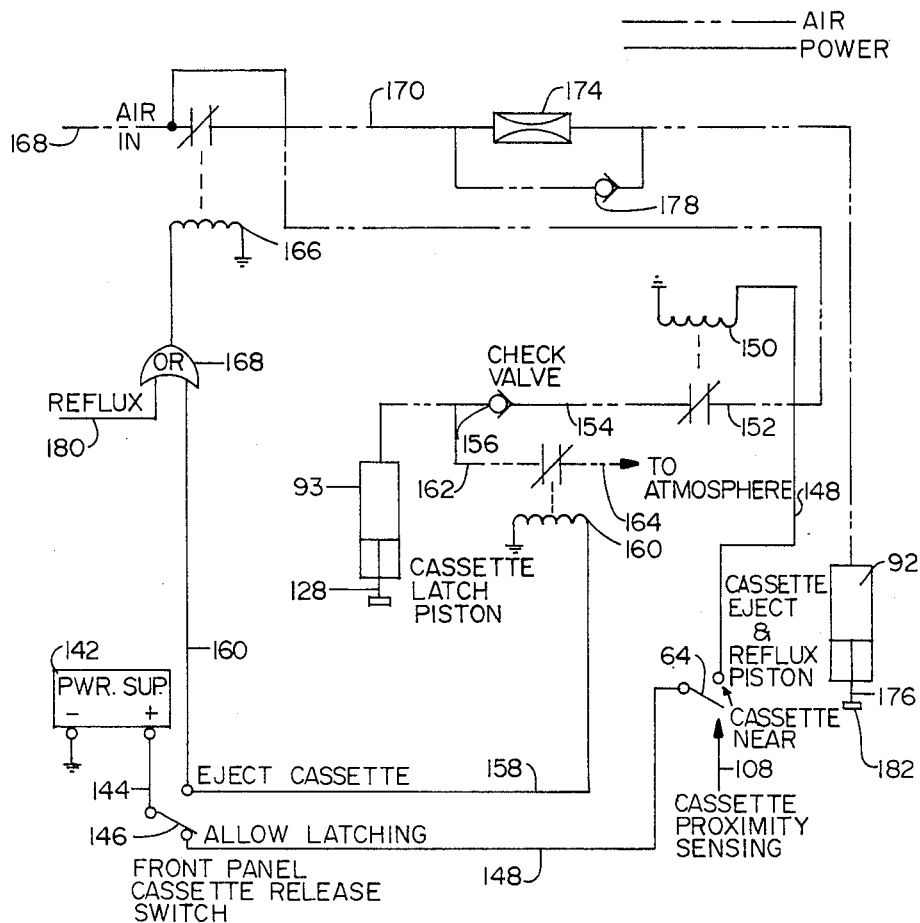
FIG. 5 is a diagram of an analog embodiment of the cassette-handling system.

Referring to FIG. 5, there is shown a schematic diagram of an electrical and pneumatic control system for sensing the proximity of a cassette and latching it into the cassette receptacle on the front panel. Although the preferred embodiment is to do the cassette latching function in software, a method which will be described below, FIG. 5 is an alternative embodiment which is instructive as to the individual sub elements of the task.

Proximity sensing of the cassette means sensing when the cassette is pushed partially into the cassette receptacle on the front panel such that power assisted apparatus may take over and engage the cassette to pull it in and positively lock it into place. The advantage of this is that it insures that the vacuum seals between the cassette and the vacuum manifolds in the vacuum generating apparatus of the balance of the system are positively sealed. The advantage of using a cassette is in the ability of the cassette double egress structure to improve the vacuum response time of the system as detailed in U.S. Pat. No. 4,475,904 which is hereby incorporated by reference. The principal advantage of the automatic latching system is ease of insertion of the cassette. That is, a great deal of strength is required to push the cassette into a latched position with the vacuum port projections compressing rubber grommets on the back of the cassette receptacle around the vacuum manifold openings. With the cassette latching mechanism, no strength at all is needed, because when the cassette is partially in the receptacle, the automatic latching mechanism takes over, and the cassette is pulled into the vacuum seal position using the strength of the pneumatic system of the machine.

Figure 6B:
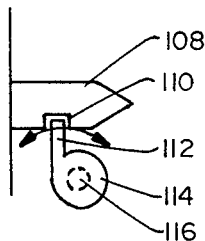
FIGS. 6A and B is a top view of the mechanical aspects of the cassette-handling system.
Figure 6A:
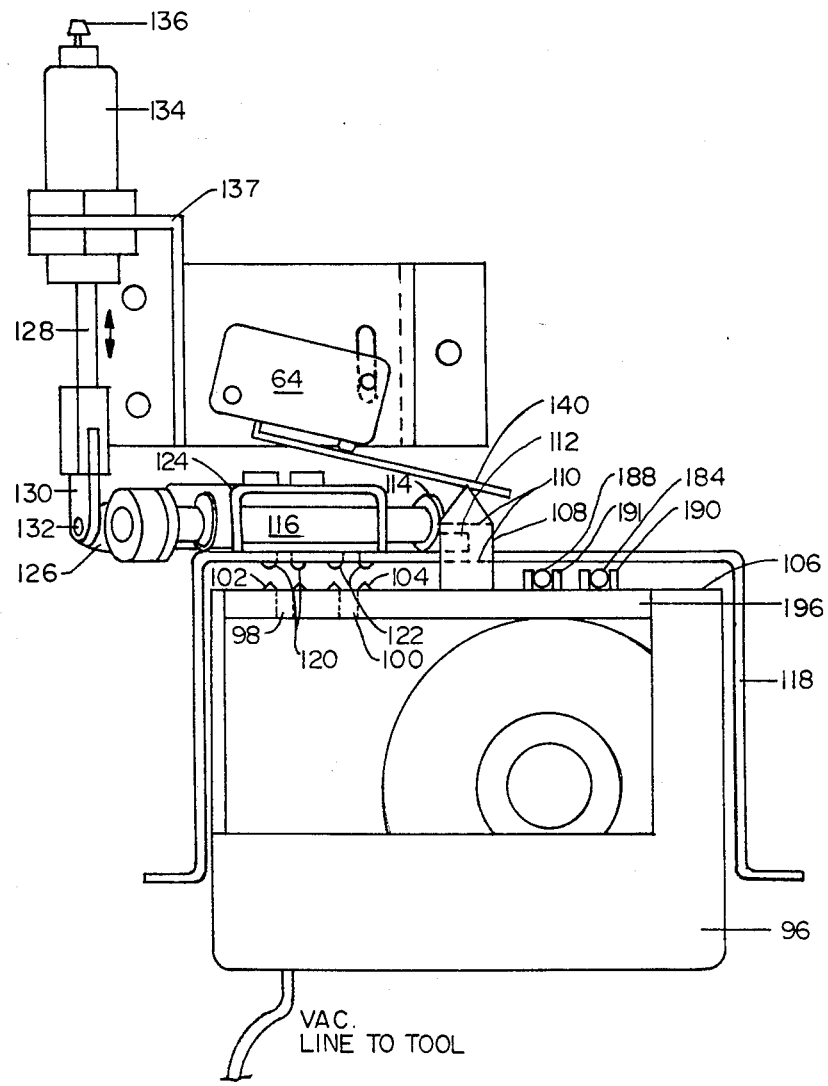

Proximity sensing is accomplished by a microswitch 64 in the preferred embodiment. In other embodiments, any known means of proximity sensing can be used. Whatever apparatus is used, it must sense when a cassette is partially pushed into the cassette receptacle, and pull it the rest of the way into the receptacle such that the vacuum seals are positively sealed, and the cassette is held firmly in such engagement. FIG. 6 shows the physical placement of this microswitch in the preferred embodiment. The cassette 96 is generally a cubicle, plastic box with a small vacuum bottle and a large vacuum bottle inside it. The vacuum bottles are connected together by vacuum hoses (not shown), and there are vacuum hoses (also not shown) which connect to two vacuum ports 98 and 100. Each vacuum port 98 and 100 has a projecting ring 102 and 104, respectively, which defines the interface perimeter of the vacuum port. This ring is triangular in shape in the preferred embodiment, and is molded in the plastic of the back surface 106 of the cassette 96. In FIG. 3, the vacuum ports 98 and 100 are shown side by side for clarity, but in the preferred embodiment, they are vertically arranged such that one is above the other. Any arrangement for placement of these ports will do however.

Figure 7:
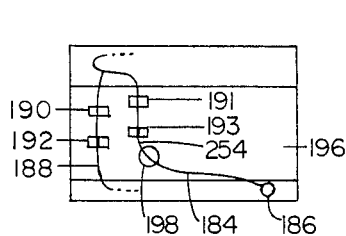
FIG. 7 is a back view of the cassette showing the routes of the surgical tubing comprising the liquid transfer system.

The back surface 106 of the cassette also has a probe 108 molded therein. This probe projects out from the back of the cassette, and has a generally cylindrical shape in the preferred embodiment although other shapes would also work. The purpose of the probe 108 is to engage a microswitch 64 placed so as to sense proximity of the cassette, and to provide a location where the cassette may be engaged by the latching mechanism. The latter is provided by a groove 110 formed in the probe which may be engaged by a tang 112 which is moved by the latching mechanism. The groove 110 is formed in the bottom of the probe 108 in the preferred embodiment, so only the phantom outlines may be seen in FIG. 6 since FIG. 6 is a top view of the cassette latching mechanism. FIG. 7 shows a side view of the probe 108 showing how the tang 112 on the latching mechanism engages a slot 110 in the probe 108. The tang 112 is a projection from the circumference of a wheel 114 attached to a shaft 116. When the shaft 116 is turned by the cassette latching mechanism, the tang 112 moves in an arc so as to move the end of the tang into the slot 110 to engage a wall of that slot. Thus the tang 112 engages the probe 108, and pulls the cassette into the receptacle 118.

When the cassette is pulled into the receptacle, the projecting rings 102 and 104 are brought into contact with elastic seals 120 and 122. In the preferred embodiment, these seals are rubber grommets which surround the openings of the various vacuum lines in the vacuum generation system. When the tang 112 has moved to its farthest position in the clockwise position in FIG. 4, the projecting rings 102 and 104 will compress the grommets 120 and 122 sufficiently to make a vacuum seal. The tang 112, wheel 114 and shaft 116 turn in unison, the shaft being supported by bearings in a support plate 124 mounted on the back of the receptacle 118. The shaft 116 has attached to the end thereof another tang 126. The tang 126 is connected to a piston shaft 128 by a coupling 130 and a pin 132. The piston shaft 128 moves longitudinally in the direction of the arrow, and this motion is translated into rotational motion of the shaft 116 by the action of the coupling 130 and the pin 132. The piston shaft 128 is an extension of a pneumatic piston 93 which receives pressurized air at a pneumatic input 136. This pressurized air forces the piston inside the unit 93 to move against an internal spring (not shown) until the forces of the air and spring acting on the piston are in equilibrium. A support bracket 136 supports the piston 93 and the microswitch 64.

Referring again to FIG. 5, which the probe 108 contacts the actuator arm 140 of the microswitch and closes the switch, current from the power supply 142 through a branch 144, a front panel cassette release switch 146 and a circuit branch 148 to a solenoid operated valve 150 coil and ground. The valve actuated by the solenoid actuated valve opens and allows pressurized air to pass from an input pressurized air line 152 to an output air line 154. This pressurized air passes through a one way check valve 156 into the pneumatic piston 93 where it pushes piston shaft 128 outward. This outward motion of the piston shaft 128 causes the tang 112 to engage the probe 108 and pull the cassette into engagement with the vacuum seals.

When the cassette is to be released, the surgeon presses the cassette release switch 146 on the front panel. This switches the line 144 into contact with the lines 158 and 160. The line 158 conducts current to a solenoid operated valve 160 which opens an air valve which connects the pneumatic piston 93's drive line 162 to the atmosphere through air line 164. This releases air pressure on the pneumatic piston 93 thereby releasing pressure by the tang 112 tending to hold the cassette in sealed position.

The line 160 is coupled to a solenoid operated air valve 166 through an OR gate 168. This OR gate has a reflux signal as its other input. This signal will be explained below. The solenoid operated valve 166 opens an air valve which gates pressurized air on an air line 168 to an air line 170 coupled to a reflux/eject piston 92 through a flow restricter 174. The pressurized air in the reflux/eject unit causes the piston shaft 176 to move outward and contact the back of the cassette and push it out of the cassette receptacle. This reflux/eject piston unit is not shown in FIG. 6, but the mechanical details of how to implement this function will be apparent to those skilled in the art. The flow restricter 174 prevents the eject/reflux piston from violently ejecting the cassette, and a check valve 178 bypasses the flow restricter to gate air back toward the solenoid operated valve 166 when a new cassette is pushed in thereby pushing the piston back into the reflux/eject piston unit and driving air out of the chamber therein.

REFLUX SYSTEM

Reflux is a process to eject materials which have accidently been sucked into an aspiration tube in a hand tool during eye surgery. Reflux requires that the vacuum to the aspiration tube be shut down, and some means be employed to apply pressure to the contents of the tube to force some of the materials in the tube to be forced out. In the prior art, several methods of reflux have been used. Most devices which have a reflux capability, and some do not have any such capability, merely vent the aspiration tube to atmosphere, but do not apply any positive or active form of forcing material out of the tube. Gravity is the only means by which materials are pulled out of the tube. This system has the disadvantage that if a piece of tissue is sucked into the tube and becomes lodged there tightly enough that gravity will not dislodge it, the surgeon is left in a difficult situation. Only two other systems have any form of positive pressure application to the tube during reflux. The United Surgical Corporation "Extra Plus" machine uses a peristaltic pump to generate the vacuum used for aspiration. When reflux is desired, the pump is reversed. This system has the disadvantage that it only works when a peristaltic pump is used for generating vacuum. Peristaltic pumps do not reach vacuum levels as quickly as the vacuum generation system of the present invention, and cannot change vacuum levels as rapidly as the venturi system used in the system herein described. Thus the advantage of a powerful reflux is offset by the disadvantage of the necessity of using peristaltic pumps to generate the vacuum and the reflux pressure. Peristaltic pumps are also more complicated, expensive and less reliable than the venturi used in the system herein described.

The Heslin-Mackool Surgical Design Corporation "Occusystem" uses gravity feed of reflux fluid by a separate tube which joins the aspiration tube near the tip of the instrument. The disadvantage of this system is that it requires additional components to implement the reflux system other than those used for the rest of the machine function, so the cost is higher. Further, the reflux fluid reservoir must be elevated, and the reflux fluid enters the aspiration tube at the tip. Thus any materials sucked past the point of juncture of the reflux tube, will not be ejected.

In contrast, the invention uses a positive reflux pressure generation method in addition to venting the aspiration tube to atmosphere. No additional components are needed to implement the reflux system other than those components already present to implement other functions.

Figure 8:
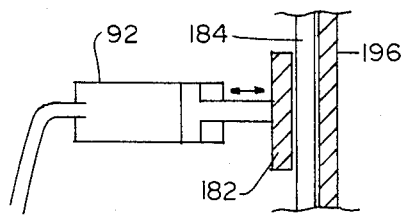
FIG. 8 is a side view of the reflux and eject piston's interaction with the surgical tubing carrying vacuum to the surgeon's hand tool.

Referring to FIGS. 5, 7 and 8, the analog embodiment of the reflux system is shown as part of the cassette handling system. The method of applying positive reflux pressure used in the invention is to pinch the surgical tubing used to conduct the subatmospheric pressure to the aspiration port after the subatmospheric pressure is cut off. This is done to decrease the volume of the surgical tubing to zero at the location under the reflux piston. This sudden reduction of volume in the surgical tubing filled with aspirated material, causes a portion of the aspirated material equal to the decrease in volume of the surgical tubing to be ejected from the aspiration port. The reflux piston 92 is the same pneumatic piston as was used for ejecting the cassette in the case where the front panel cassette release switch was pushed. However, when reflux is desired by the surgeon, a reflux signal is generated on the line 180 which passes through the OR gate 168 and energizes the solenoid operated valve 166 to apply air pressure through the air lines 168 and 170 and the flow restricter 174 to the pneumatic reflux piston 92. Since the line 158 is not energized during a reflux, the solenoid operated valve 160 is not energized, and the cassette remains latched. The reflux piston has a large "foot" on the end of the piston that is aligned with the path of the surgical tubing which conducts the aspiration vacuum or subatmospheric pressure to the hand tool. FIGS. 7 and 8 show front and side views of the back of the cassette with the internal details eliminated to illustrate how the reflux piston interacts with the cassette back wall and the surgical tubing to cause the reflux. FIG. 7 details the paths of two of the surgical tubes carrying vacuum in the cassette. The line 184 carries vacuum to a port 186 on the front of the cassette for coupling to the hand tool. The tube 188 carries vacuum for other purposes internal to the cassette operation and is not involved in reflux operation. Each tube is held in place by clamping projections 190–193, each of which comprises a pair of projecting plastic guides molded into the back wall 196 of the cassette between which the tube is pressed. A top view of the tubes 188 and 184 and the projecting guides 190 and 191 is shown in FIG. 6. The target area 198 in FIG. 7 is the area where the reflux piston foot squeezes the tube 184 to cause the reflux. FIG. 8 illustrates this squeezing action. The back wall 196 of the cassette provides a solid surface against which the tube 184 can be squeezed. The foot 182 of the reflux and eject piston is shown in the retracted position when no pressure is applied to the tube 184. When the piston 92 is pressurized, the foot 182 is pushed right and squeezes the tube 184 reducing its volume to zero under the foot thereby causing the reflux surge to be ejected from the aspiration port.

SYSTEM FIRMWARE

The preferred embodiment for the cassette handling system is use of a software subroutine running on the CPU 30 in FIG. 1 to handle the logic of proximity sensing, cassette ejection and reflux. To illustrate this preferred embodiment reference is made to FIG. 2 which shows the pneumatic system of the invention, and FIGS. 9A and 9B which show a flow chart of processing steps for the cassette handling subroutines. The system's pneumatic and vacuum system shown in FIG. 2 are involved in this cassette handling. The pertinent part of FIG. 2 with respect to cassette handling are the solenoid operated air valves 166 and 150 in the lower right hand of the figure, and the reflux and eject piston 92 and the cassette latch piston 93 pneumatically coupled to these solenoid operated valves. The solenoid operated valves are also pneumatically coupled to a pressurized air source of air at a regulated pressure of from 40 to 45 psi controlled by the regulator 90. The solenoid operated valves are comprised of two air inputs and a single air output which can be pneumatically coupled to either air input depending upon the state of an electrical control signal on a control line coupled to the CPU. For example, the solenoid operated valve 166 has a pneumatic input connected to the pressurized air bus 88 and a pneumatic input coupled to the atmosphere. The pneumatic output is coupled to the reflux and eject piston 92, and is pneumatically coupled to the air bus 88 when the control signal on a control line in the control bus 206 is in the "pressurize" state, and is pneumatically coupled to the atmosphere when the control signal on the line 206 is in the "open" state. The same is true for the solenoid operated valve 150.

The control lines on the control bus 206 come from the RAM and I/O ports 74 in FIG. 1 through the bus 84 and the drivers 86. In the preferred embodiment, the drivers 86 are output stages of the I/O ports 74. Each solenoid operated valve has its own drive line and its own I/O port such that each can individually "pressurized" or opened to atmosphere by the CPU 30. When the CPU wishes to pressurize a particular valve, it addresses that valve using the decoder 82 and the proper I/O port and writes a particular bit or code to that I/O port. This bit is latched, and controls the state of the driver 86 driving the coil of the solenoid operated valve so addressed. The desired input is then connected to the output.

Figure 9A:
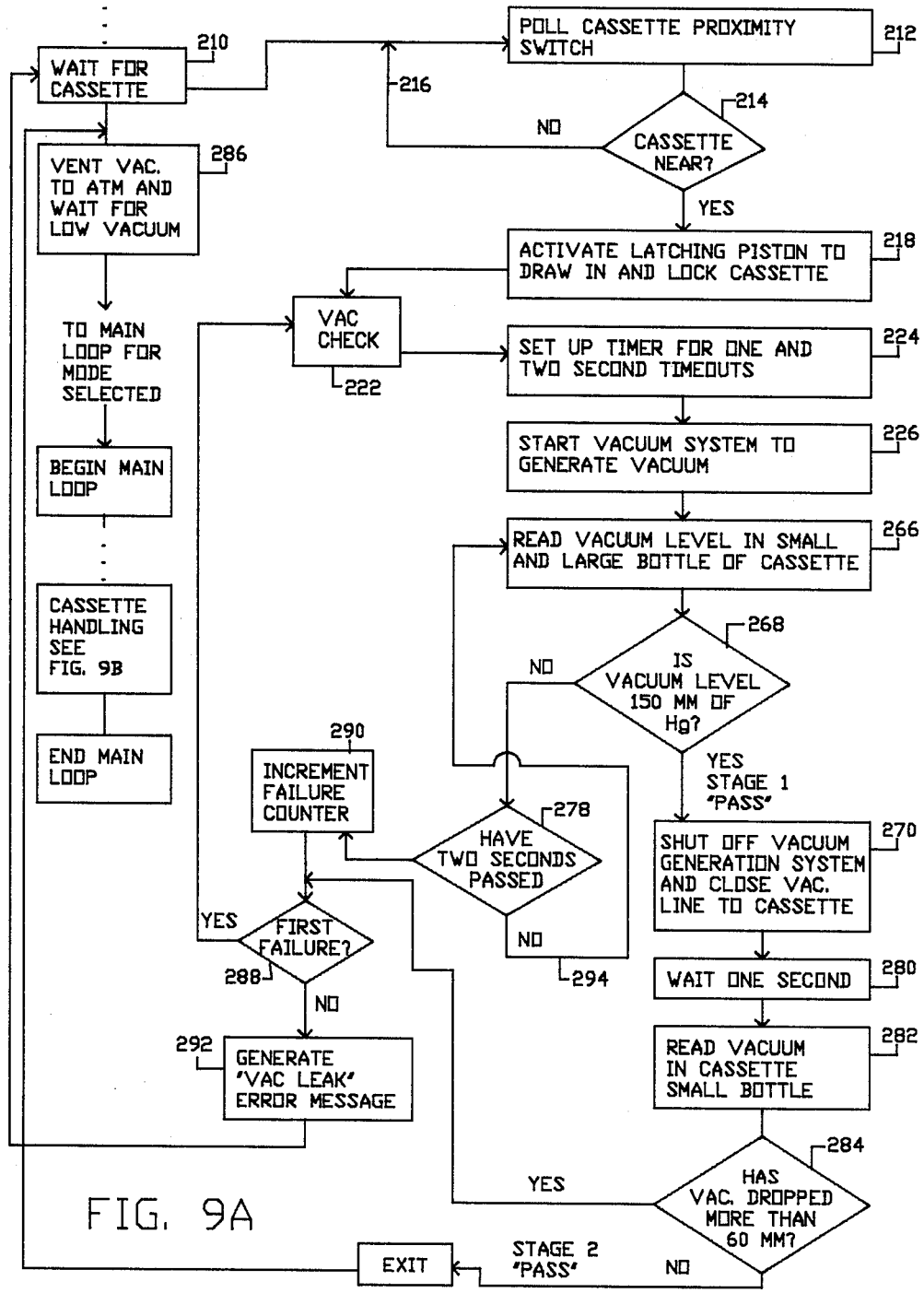
FIGS. 9A and B is a flow chart of the cassette-handling process of the preferred embodiment and the reflux process.

Referring to FIG. 9A there is shown a flow diagram of part of the cassette handling process implemented by the invention wherein the cassette proximity is sensed, the cassette is pulled in and latched, and the vacuum seals are tested. The process starts with the step 210 where the machine waits for the cassette to be pushed into the front panel receptacle. The substeps of this waiting step consist of the steps 212 and 214. Step 212 consists of addressing the cassette proximity sensor switch 64 through the front panel control and sensor interface 54 and reading the state of the switch. The data read from the switch 64 is then compared in step 214 to data reflecting the state of the switch when a cassette is near and a determination is made regarding whether a cassette has been partially pushed into the front panel. If the answer is no, processing proceeds back to step 212 as symbolized by branch 216. If the answer is yes, processing proceeds to the step 218 to pull the cassette into the receptacle.

Step 218 represents the steps of addressing the cassette latch piston 93 solenoid operated valve 150 through the RAM and I/O ports 74 and writing a "pressurize" command to it. This command causes pressurized air on the pneumatic line 88 to be coupled to the pneumatic line 220 in FIG. 2 thereby causing the piston 93 to move. As explained with reference to FIG. 3, this movement of the piston engages the cassette and pulls it into tight sealing engagement with the vacuum seals.

The vacuum seal check process is symbolized by the step 222, and the first substep in this process is to set up some internal timers in the microprocessor 30 for a two second timeout in step 224. Next, the vacuum system is started in step 226 to generate vacuum on the vacuum manifold coupled to the cassette through the vacuum seals. To do this, the microprocessor sends a digital word to the D/A converter 42 requesting a vacuum level of 150 millimeters of mercury. The vacuum control system then generates an error signal which causes the vacuum level to begin to rise in the vacuum line 63 and in the small and large bottles of the cassette. To understand this, the reader should refer to FIG. 3 which shows a schematic diagram of vacuum system of the cassette.

In FIG. 3, the cassette is comprised of a small vacuum bottle which has one vacuum input in the top of the bottle coupled to the vacuum line 63. Another vacuum line 230 is used to transfer liquid from the small bottle to a large bottle 232. The vacuum line 230 extends into the small bottle 228 such that its vacuum input is located at the bottom of the small bottle 228. The other end of the vacuum line 230 is coupled to a vacuum input of the large bottle 232. A solenoid operated pinch valve system 234 serves to control transfers of liquid between the small bottle and the large bottle by pinching or not pinching the surgical tubing used for the vacuum line 23. In FIG. 2, the solenoid operated pinch valve system 234 is comprised of a solenoid operated valve 236 coupled to a transfer pinch piston 238. The SOV 236 has a pneumatic input coupled to the pneumatic line 88 and a pnuematic output line 240 which is coupled to the pneumatic input of the transfer pinch piston 238. When the microprocessor wishes to isolate the large bottle from the small bottle, it addresses the I/O port on the RAM and I/O circuit 74 and writes a "vent" bit into the I/O port latch. This causes the SOV 236 to close the valve allowing pressurized air to vent from the pneumatic line 240 thereby allowing the transfer pinch piston to push outward and pinch the surgical tubing of line 230 closed. When the microprocessor wishes to allow a liquid transfer from the small bottle to the large bottle, it addresses the I/O port assigned to the the SOV 236 and sets the bit to "pressurize". This causes the SOV 236 to connect the pneumatic line 240 to the pneumatic buss line 88. This vents the pressure in the transfer pinch piston such that a spring can return the piston to an "unpinched" position. To actually cause a liquid transfer to occur, the microprocessor opens the vacuum line 230, and applies vacuum to another vacuum line 244 coupled to another vacuum input of the large bottle 232. This vacuum line 244 is connected through a water trap 246 to a venturi 248 shown in FIG. 2. The water trap 246 prevents fluid from being aspirated into the machine via the line 244 if the large bottle becomes full. To apply vacuum to the line 244, the microprocessor addresses an SOV 250 which has a pneumatic input coupled to the pneumatic line 88 and writes an "open" bit to it causing the valve to allow pressurized air to pass between the line 88 and the venturi air flow input 252. The flow of air through the venturi causes a vacuum to arise in the vacuum line 244. This evacuates the large bottle and the transfer line 230. Because there is fluid in the small bottle, the fluid is sucked into the transfer tube 230 and moves to the large bottle 232. As liquid leaves the small bottle it is replaced with air from the vacuum line 63 because the microprocessor 30 has previously sent a digital word to the D/A converter 42 requesting zero vacuum. This closes the linear valve 85 in FIG. 2, and allows the vacuum line 63 to suck air from the atmosphere through the throat of the venturi 65. The small bottle 228 also has two electrodes 262 and 264 affixed to the top of the bottle and projecting down into it. Together, these two electrodes, and some electronics similar to the comparator and power supply coupled to the in line water sensor 68, comprise the small bottle liquid level sensor 66 shown in FIG. 1. The microprocessor 30 polls this liquid level sensor 66 from time to time to check the status of the small bottle. When the bottle is full, the sensor 66 senses this fact, and the microprocessor 30 initiates the liquid transfer process described above to empty the small bottle.

The vacuum line 230 is also coupled to the hand tool by a vacuum line 254 through a segment of surgical tubing which is subject to pinching by an aspiration solenoid operated pinch valve system 256. Referring again to FIG. 2, this pinch valve system is comprised of a solenoid operated valve 258 and an aspiration pinch piston 260. This system operates identically to the transfer pinch valve system and will not be further described except to say that the aspiration pinch valve system 256 is caused by the microprocessor to pinch the surgical tubing such that the vacuum line 254 is isolated from the line 230 during liquid transfers from the small bottle to the large bottle. During aspiration of fluid from the area of the operation, the pinch valve system 256 is left open such that the vacuum on the line 63 is transferred to the line 230 and onto the line 254. The microprocessor causes the transfer pinch valve system 234 to be closed during the aspiration of fluid from the operation site such that the vacuum on the line 63 draws the fluid into the small bottle, and no fluid is sucked into the large bottle. The line 244 can be vented to the atmosphere during such operations. This small bottle/large bottle system allows the vacuum response time of the system to smaller than would be the case if only a large bottle was used. This makes the system more agile and easier for the surgeon to work with.

Returning to consideration of the cassette handling and vacuum seal testing process, the step 266 represents the step of reading the vacuum sensor 49 with the pinch valve 234 open and the pinch valve 256 in FIG. 3 closed. The valve 250 in FIG. 2 should also be in the "pressurize" position such the venturi 248 is generating subatmospheric pressure in the vacuum line 244 to test the seal on this vacuum line as well as the seal on the vacuum line 63. The vacuum level on the line 63 will then represent the vacuum level in the small and large bottles will then be represented by the vacuum level on the line 63.

The step 268 represents a comparison of the vacuum level reading from step 266 to a constant of 150 mm of Hg stored in memory. If this level of vacuum is reached within two seconds, the first stage of the vacuum test is passed, and the vacuum system is shut down and the cassette is sealed off to check for small bottle leaks in the step 270. This is done by addressing the solenoid operated valve 274 in FIG. 2 and closing it so as to seal the venturi 65 off from the vacuum line 63. The solenoid operated pinch valve 234 in FIG. 3 must also be closed to isolate the small bottle 228 from the large bottle 232 so as to prevent the venturi 248 in FIG. 2 from bleeding away all the small bottle vacuum through the line 244. The large bottle 232 is therefore allowed to return to atmospheric pressure. The large bottle need not be checked for large leaks, since if there were any, the vacuum would never have risen to 150 mm of Hg in the first place within the two second timeout period of step 278 to be described below.

After the small bottle 228 has been isolated, the microprocessor waits for one second as symbolized by the step 280. This done by waiting for timeout of a timer set in step 224 for timeouts every second. Upon the occurrence of this timeout, the vacuum sensor 49 is again read to determine the vacuum level in the line 63 and the small bottle 228. This step is symbolized by the step 282. If the vacuum has not fallen more than 60 mm of Hg, then the cassette and seals have passed. This test is represented by step 284. The microprocessor 30 then exits the cassette testing routine, vents the small bottle vacuum to atmosphere by reopening the solenoid operated valve 274 in step 286, and proceeds to the main loop of the particular mode selected.

In the event there is a large vacuum leak somewhere in the cassette, the seals or the vacuum lines leading to the cassette, the cassette vacuum will never reach 150 millimeters of mercury, or will reach it very slowly depending upon the size of the leak. To detect this condition, a test symbolized by the step 278 is performed. This step represents a time limit on the rate of pressure fall toward the goal of 150 mm of Hg vacuum level being tested for in step 268. During the fall of pressure, the branch instruction of step 268 causes the test and branch instructions of the step 278 to be performed each time the test of step 268 indicates that the vacuum level has not yet risen to 150 mm of Hg. The test of step 278 is to determine whether two seconds has passed. If it has, then the cassette has failed, and processing proceeds to the test of a step 288 after adding one to a failure register or incrementing a failure counter in a step 290. A cassette will be given two chances to pass the vacuum test, after which it will be failed and an error message displayed. The test of step 288 reads the number in the failure counter and determines if it is one or greater than one. If the failure number is one indicating a first failure, processing proceeds to the step 222, and the vacuum check is repeated starting with the step 224. If the failure number is greater than one, the step 292 is performed to write an error message to the display indicating a vacuum leak exists. Processing then proceeds to the step 210 to wait for insertion of the next cassette.

If the two second timeout tested for in the step 278 has not yet occurred, then processing returns to the step 266 as symbolized by the line 294. If at any time before the two second timeout during the execution of the loop between steps 268 and 278, the vacuum level reaches 150 mm of Hg, control passes out of the loop to the step 270 previously described. That completes the description of the vacuum testing procedure of the cassette handling routine.

Figure 9B:
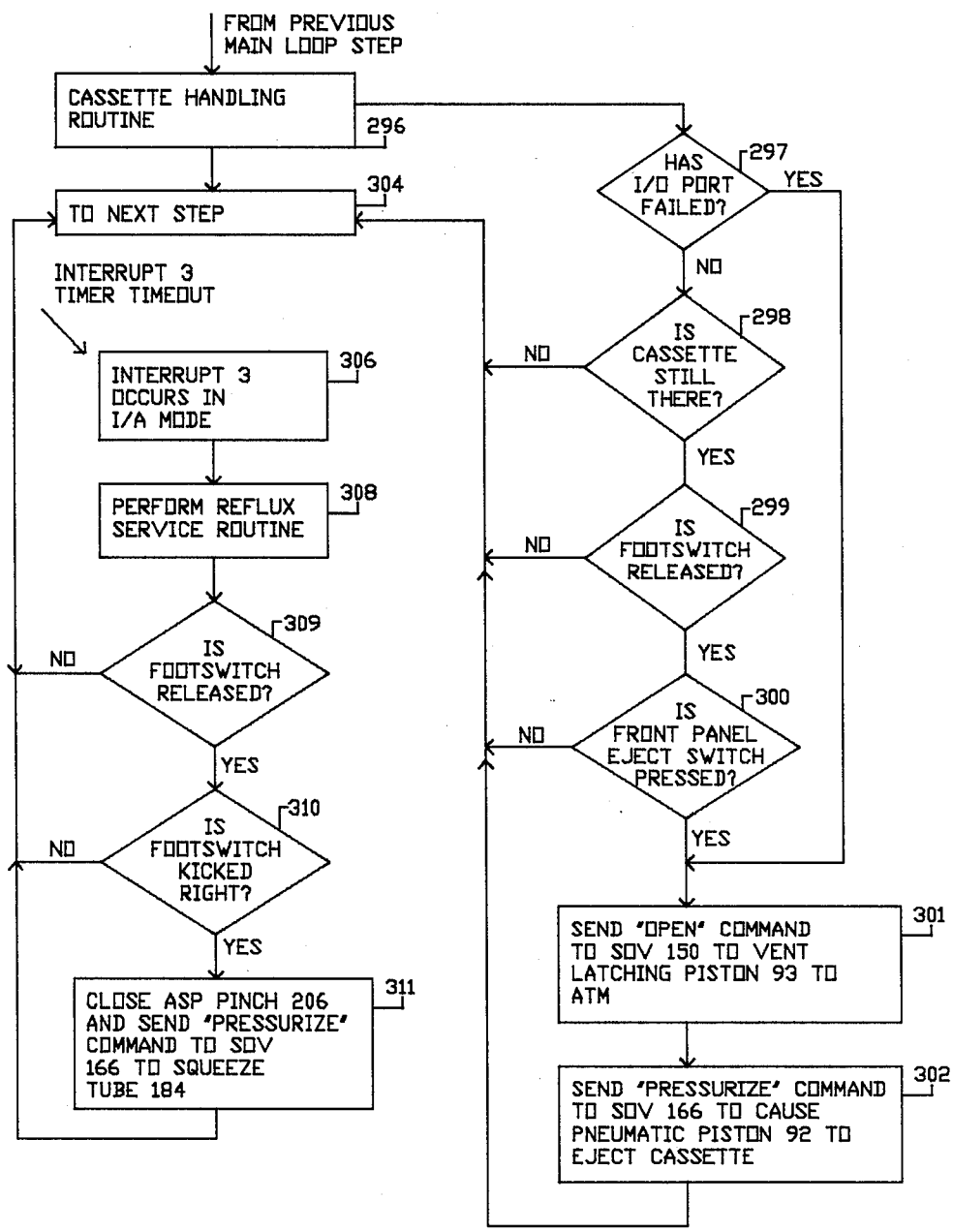

FIG. 9B illustrates the process implemented by the microprocessor 30 in handling cassette ejection and performing reflux. The routine is entered from some step in the main loop of the particular mode in which the system is operating as symbolized by the step 296. The cassette handling routine of step 296 is comprised of the steps 297-302. The step 297 is a test for I/O port failure. The I/O ports of the unit 74 can be tested by writing bits to the latches therein and reading these bits. If these ports fail, the machine will not be capable of operation, and the cassette must be ejected to signal this inability to operate. The step 297 tests the I/O ports, and branches to the step 301 upon a failure of an I/O port. The step 301 represents the I/O instruction of addressing the solenoid operated valve 150 in FIG. 2, and writing an "open" command to it to vent the latching piston 93 in FIGS. 2 and 6 to atmosphere thereby clearing the way to eject the cassette. Next, the step 302 is performed wherein the solenoid operated valve 166 in FIG. 2 is addressed, and a "pressurize" command is sent to it via the control bus 206 thereby allowing the pressurized air on the pneumatic line 88 to enter the reflux and eject piston 92 and push its piston outward. The piston contacts the back of the cassette and pushes it out of the receptacle.

Returning to step 297, if the I/O port did not fail, then a test 298 is performed. This test is to determine if the cassette is still present, for if it is not present, then there is no need to go any further and interrogate the the front panel cassette eject switch. This test is performed by addressing the cassette proximity sensor 64 and reading its current state as best visualized in FIG. 6.

Next the test of step 299 is performed to determine if the surgeon has released pressure on the footswitch. If the footswitch is still depressed, the cassette should not be ejected, because the surgeon might still be operating. In such a case, processing proceeds to the next step in the main loop which is symbolized by a block 304.

If the footswitch is not depressed, then the front panel eject switch may be pushed to eject the cassette, and the microprocessor will do so. Only if all the previous conditions have been satisfied, will the front panel eject switch be polled in a step 300. If the switch has not been pushed, processing proceeds to the step 304 to continue with the main loop. If it has been pushed, then processing proceeds to the step 301 and the step 302 where the cassette is ejected as previously described.

REFLUX SYSTEM

The microprocessor 30 has several on board timers which are initialized by the microprocessor to generate interrupts periodically. Each interrupt is serviced by performance by the microprocesor of a service routine stored in PROM 38 in FIG. 1. Each interrupt controls different functions, and each interrupt occurs during any mode the machine is operating in. However, since each interrupt has several functions, and not all the functions are needed in each mode, there are branching instructions in each interrupt which test the front panel mode select switches 60 to determine the mode. Once the mode is determined, processing in the service routine is vectored to the proper portion of the service routine which performs the functions relevant to the particular mode. The reflux capability of the system is a portion of the service routine for interrupt 3, and the flow diagram for the reflux process is given in FIG. 9B.

Referring to FIG. 9B, step 306, when the interrupt 3 timer times out, the interrupt occurs and the microprocessor vectors itself to the starting address for the interrupt 3 service routine as symbolized by step 306. The step 308 next performed, represents a test in the interrupt 3 service routine to determine the mode of operation of the system. If the system is in the I/A mode, i.e., irrigation and aspiration, then reflux is one of the functions which may be performed if the surgeon so requests. The steps 309-311 represent the individual steps of the reflux portion of the interrupt 3 service routine.

Step 309 represents a test and branch instruction to read the position of the footswitch to determine whether it is released. The surgeon requests reflux by releasing the footswitch and kicking it to the right. Two tests must be performed to determine whether this condition exists, and the step 309 is one of them. The other test is performed in the step 310. If the result of the test of the step 309 is that the footswitch is not released, then reflux is not being requested and processing returns to the next step in the interrupt service routine or the next step in the interrupt 3 service routine depending upon whether other functions in the service routine need to be performed for the particular mode. If the footswitch is released, then processing branches to the test of the step 310 where the footswitch is tested to determine whether it is kicked to the right. There is a microswitch 76 in FIG. 1 located in the footswitch which is positioned to detect if the footpedal is kicked to the right. This microswitch is used in both the fragmentation control function in the I/A and Frag mode, and for the reflux control functon in the I/A without Frag mode. It is this footswitch which is read by the step 310. Referring to FIGS. 10 and 2, if the microswitch 76 indicates that the footswitch is kicked right, then the solenoid operated valve 258 in FIG. 2 is addressed and a "close" command is sent to it to gate pressurized air through to the aspiration pinch valve 260 to cause it to pinch off the surgical tubing carrying vacuum to the surgeon's hand tool. Then the solenoid operated valve 166 in FIGS. 1 and 2 is addressed and a "pressurize" command is sent to it to gate pressurized air through to the reflux and eject piston 92 shown in FIG. 8. This causes surgical tube 184 to be squeezed thereby causing its volume to be decreased and some material at the opening in the vacuum line at the hand tool to be squeezed out.

SYSTEM CONTROL FIRMWARE

The system, when first started, performs a series of tests to verify that certain critical components are in working order. When the system is first powered up, processing starts at a cold start step 314, and proceeds to a step 316 to perform certain power on tests. These tests include a test of the EPROM 38 in FIG. 1 in step 318 and a check of the external RAM 74 in FIG. 1 in a step 320. The step 318 adds up all the bytes in the EPROM 38 to form a checksum and compares that checksum to a constant to determine if all the bits stored in the EPROM are still in their original state. If the checksum is correct, then the test of step 320 is performed. If the checksum is not correct, then step 322 is performed to display an error message. The test of step 320 involves the writing of a number to the external RAM followed by a read of that number. If the answer is correct, then processing proceeds to step 324.

Step 324 is a system check step which checks the timing of the A/D converter as symbolized by step 326. The first step in this process is to start the A/D conversion process as symbolized by the step 328. This step consists of addressing the A/D converter and sending a chip select signal to its start input. Next, the end of conversion output signal from the A/D converter is read to see if the conversion is done as step 330. Step 332 is a branch if the end of conversion bit indicates that the conversion is done. If the conversion is not done, a loop counter is incremented in step 334. The step 333 is a read of the loop counter and comparison to a maximum acceptable loop count. If the loop count is less than the maximum, as tested in step 335, then processing returns to step 330. In case the A/D converter fails completely and never generates an end of conversion bit there must be some manner of detecting this fact. The test of step 335 is such a safeguard. If the result of the comparison is that the maximum count has been exceeded, then step 340 is performed to display an error message.

If the conversion is done, a branch to the step 336 is done where the contents of the loop counter are compared to a fixed constant set at a maximum number of loop times that can be tolerated for conversion time. If the number of loops performed during this conversion exceeds the maximum as tested in step 338, then the conversion is too slow, and an error message is displayed in step 340. If less than the maximum, then the test is passed, and processing branches to the step 342.

The step 342 is an initialization of all variables used in the system. For example a byte is sent the RAM and I/O port circuit 74 in FIG. 1 to cause it to enter the proper mode of operation, all solenoid operated valves are set to their proper initial state, the vitrectomy probe is turned off, the aspiration pinch valve 260 is closed, and the pressure and vacuum levels are set to zero. Further, all LED's in the displays are cleared to the off state, the low air pressure switch 70 is read to determine if the input air pressure is at an acceptable pressure, and a message to release the footswitch is displayed. Finally, the vacuum sensor is read to verify that the vacuum system is safe and an error message is displayed if vacuum is not zero or if the footswitch is depressed for more than 8 seconds.

Next processing proceeds to a warm start step 344 where all interrupts are masked, and all the pinch valves are re-initialized to predefined states. The pressure and vacuum levels are set to zero, and the low air pressure switch is read to determine if the input air pressure is less than 70 psi. This warm start step is performed every time the mode of machine operation is changed as symbolized by the vector 346 from other steps in the flow diagram of FIG. 10 wherein the mode select switches 60 in FIG. 1 are read to determine the desired mode of operation.

The step 346 is then performed to determine the desired mode. There are several routines each of which controls the machine in one of its modes. Each routine has a group of steps therein which check the state of the mode select switches and determines whether there has been a change. If there has been a change, then the new mode code is written to a variable in RAM. The step 346 reads this mode code, whereupon it is compared to the codes for the various modes and a conclusion is drawn as to the desired mode. A step 348 makes this comparison and causes a branch to the starting address of the proper routine to control that mode.

Figure 10A:
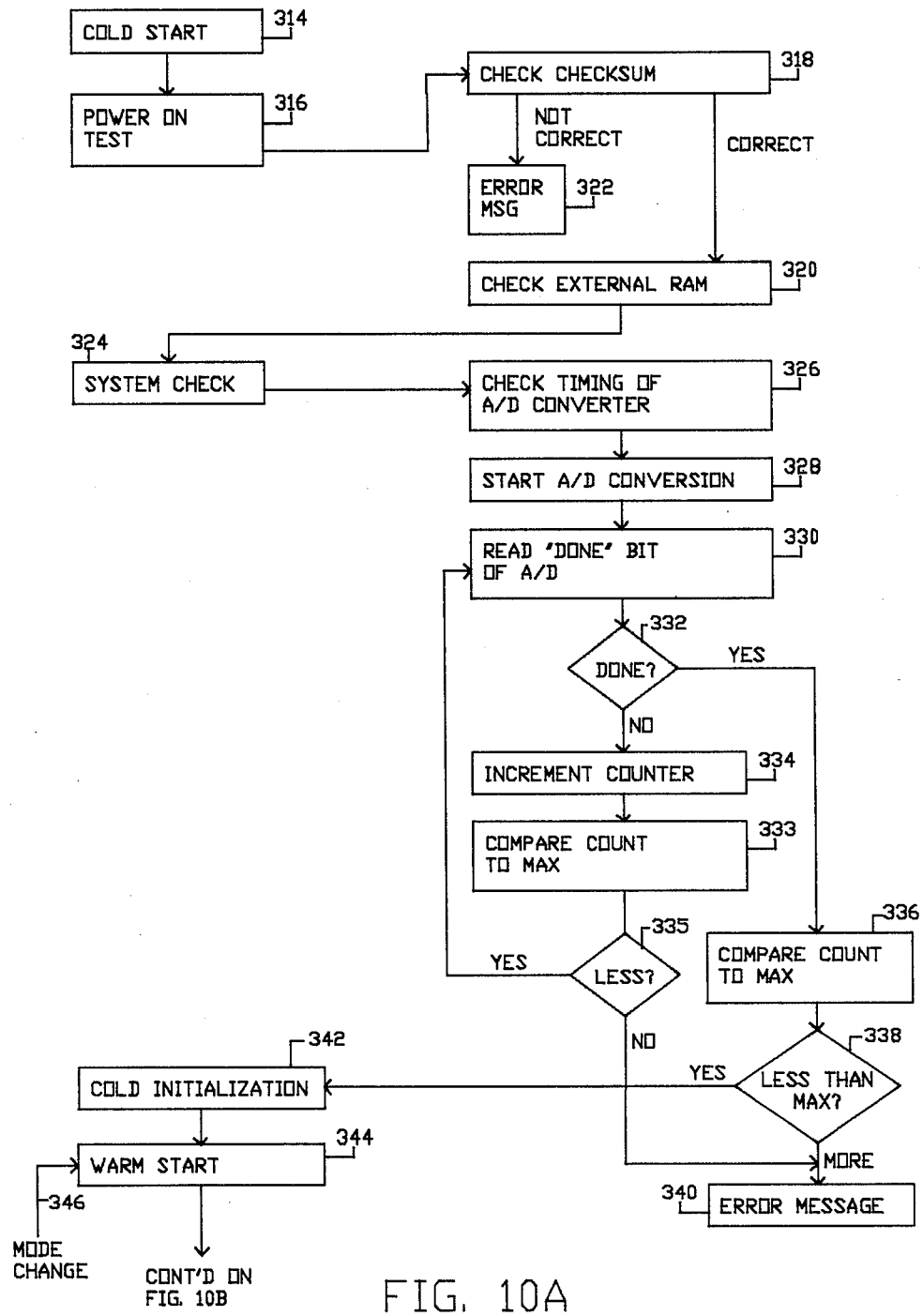
FIGS. 10A-I is a flow chart of the various processes the system performs in the various modes of operation and the processes performed by the control circuitry in getting into and controlling the various modes and changes between modes.
Figure 10B:
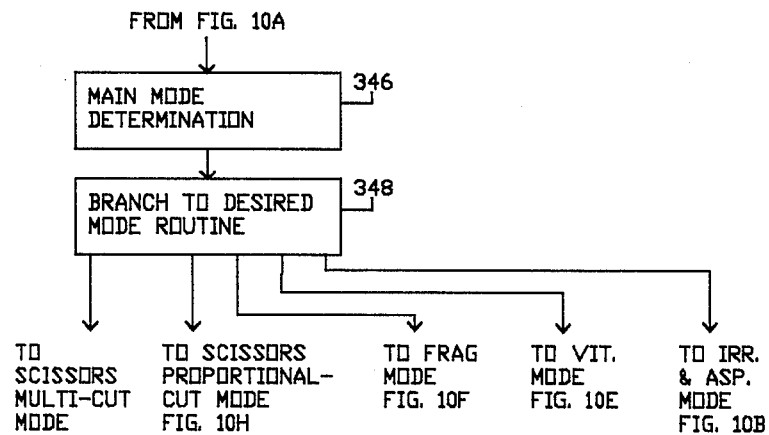
Figure 10B:
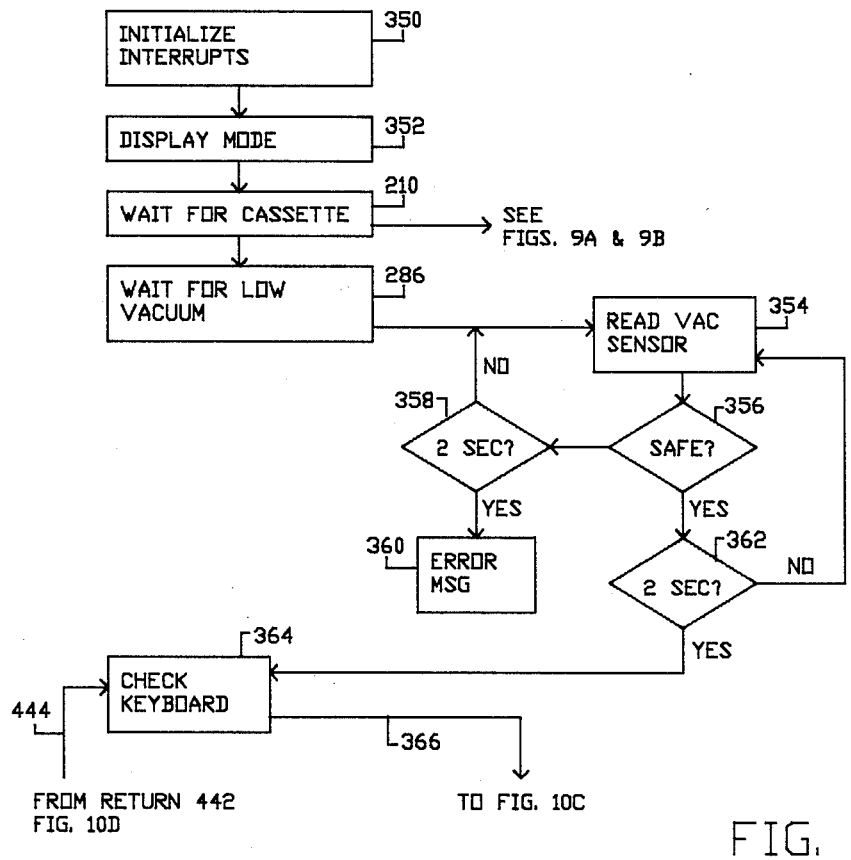

If the mode selected is the irrigation and aspiration mode, the first step performed is step 350 on FIG. 10B. This mode supplies irrigation fluid through a port on the front panel and a surgical tube which can be pinched off by the action of the irrigation pinch piston 89 in FIG. 1. This pinch piston is under the control of a solenoid operated valve 352 shown in FIG. 2 controlled by the microprocessor 30 through the control bus 206 from the RAM and I/O ports 74. The mode also supplies vacuum to the hand tool to aspirate the irrigation fluid and any foreign bodies or fragments of tissue in the region of interest. The step 350 initializes the interrupts needed for this mode. This process consists of setting some internal timers in the microprocessor to generate interrupt 1 and interrupt 3 at the desired intervals. In the I/A mode, interrupt 1 control the vacuum generation system and interrupt 3 control the irrigation flow, reflux and vacuum venting.

Next the name of the mode is displayed on the alphanumeric display in step 352, and a step 210 waits for the cassette to be pushed in the front slot. When the presence of the cassette is detected, the process of FIGS. 9A and 9B is performed. After completion of this process, this step 286 is performed to vent the vacuum from the cassette test to atmosphere and wait for the pressure to drop to atmospheric pressure. This step involves continuous polling of the vacuum sensor 49 in step 354 and a test for zero or safe vacuum level in a step 356. If the vacuum has not fallen to a safe level another test for a 2 second timeout is performed in step 358 is performed. If no timeout has occurred, processing returns to step 354. If timeout has occurred, processing proceeds to step 360 to display an error message. If the test to step 356 showed a safe level, a test for a two second timeout is performed in step 362. If no timeout has occurred, step 354 is performed again. If timeout has occurred, a step 364 is performed to check the keyboard for a change of mode.

Figure 10C:
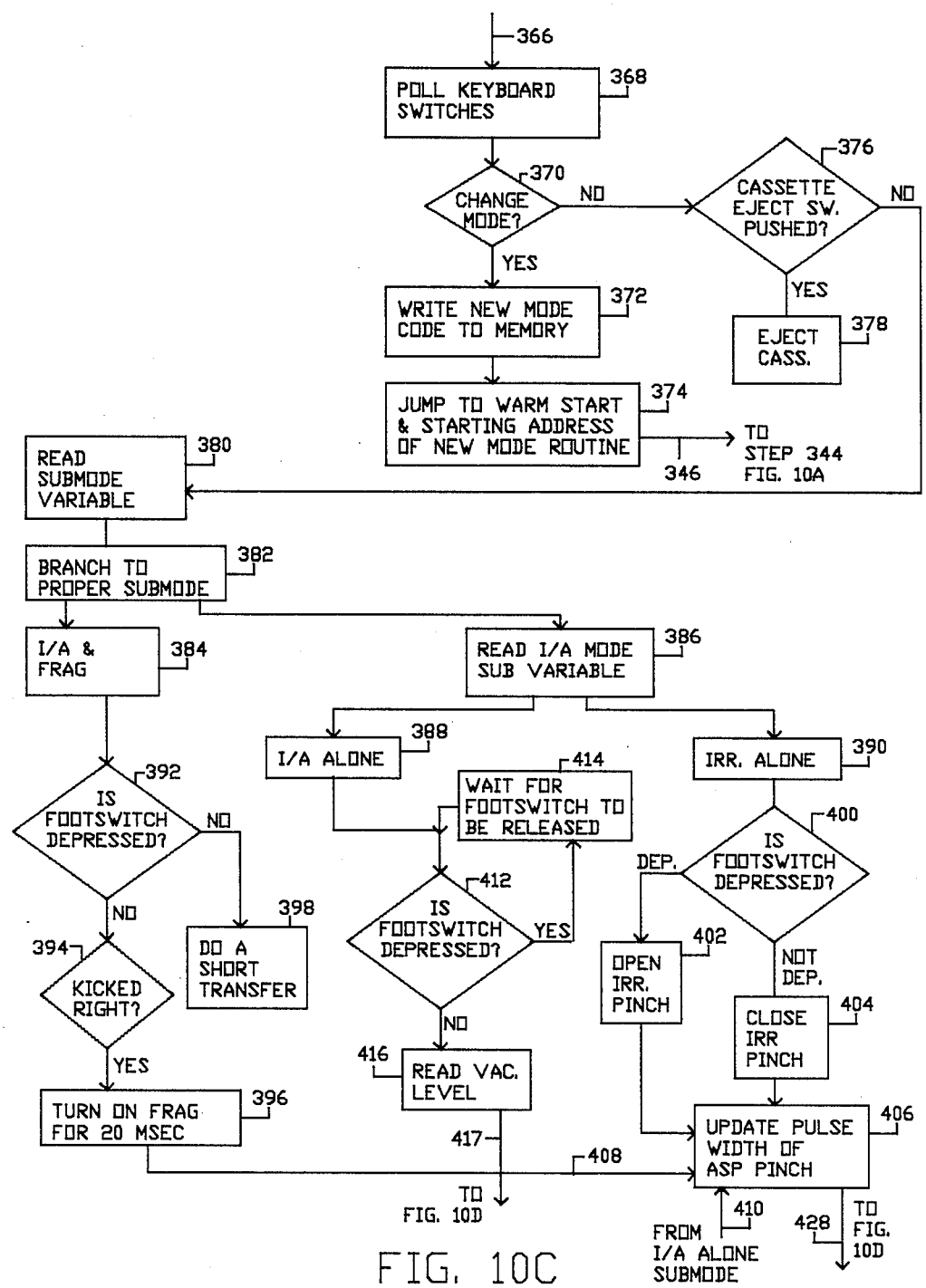

Step 364 is the first step in the main loop for the I/A mode, and is comprised of the steps indicated by the vector 366 shown in FIG. 10C. Upon completion of the main I/A loop, step 364 is performed again, as indicated by the vector 368 from the return statement at the end of the I/A main loop. The first substep 368 in the step of the 364 is to read the keyboard switches 368. The results are compared to the current mode code stored in memory in a step 370 to determine if the mode is changed. If it has, step 372 writes the new mode code to memory, and the new mode code is compared to the mode codes until the new mode is determined whereupon a jump to the starting address of the new mode is made in a step 374. If no change in mode has occurred, the cassette eject switch 62 is polled and tested to see if it has been pushed in a step 376. If it has, the cassette is ejected in a step 378 in the manner shown in FIG. 9B, steps 300–302. If it has not been pushed, step 380 is performed to read the sub-mode variable.

The I/A mode has three submodes: irrigation only with no aspiration; irrigation and aspiration with fragmentation; and irrigation and aspiration alone. The particular submode is stored by the step 364 when the keyboard is read and the mode code is written. Step 382 vectors processing to the proper submode routine starting address. If the I/A and frag buttons were pushed simultaneously the submode code written by the change mode subroutine is I/A and Frag submode, and the branch is to step 384, but if the I/A button was pushed alone, the branch is to the step 386 where the I/A sub-sub mode code is read to determine if the Irrigation Only sub-sub mode is desired or the I/A mode alone is desired. Just which sub-sub code is written by the change mode subroutine depends upon whether the I/A button was pushed once or twice. One push vectors processing to a step 390, and two pushes vectors to a step 388.

The first steps 392 and 394 in the I/A Frag sub mode are to test whether the footswitch is not depressed and kicked right indicating that the fragmenter is to be turned on by writing a proper signal to and addressing the I/O port 74 so as to send an "on" signal out the bus 80 in FIG. 1. This results if the result of the test 392 is no and the result of the test 394 is yes and is symbolized by the step 396. The microprocessor 30 times the amount of time the fragmentation tool has been on, and writes an "off" command to the tool after 20 milliseconds have passed. If the answer to the test 392 is no, a short transfer of liquid from the small bottle to the large bottle is performed. This is done by closing the pinch valve 256, opening the pinch valve 234, and opening the valve 250 to cause the venturi 248 to generate subatmospheric pressure in the line 244. This process, symbolized by the step 398, sucks some of the liquid from the small bottle 228 to the large bottle 232, but the transfer valving conditions are not maintained long enough to do a complete transfer.

If the vector is to step 390, the first step is to test the footswitch in step 400. If it is depressed, the step 402 opens the irrigation pinch valve 89 to allow irrigation flow out the socket on the front panel to the handtool. If the footswitch is not depressed, then step 404 closes the irrigation pinch 89 to block flow. Processing is vectored to the step 406 after either steps 404 or 402 is performed.

Step 406 updates the pulse width of the aspiration pinch to the proper flow rate for the particular sub-mode. Generally the job of control of the vacuum *level* is performed by interrupt 1. There is, in modes using vacuum, a simultaneous control of the *flow rate* of materials aspirated by the vacuum line 184 provided by the microprocessor 30 through modulation of the pulse width of periodic "pinch off pulses" sent to the aspiration pinch valve 258 and pinch piston 260. That is, the flow rate in the vacuum line 184 is controlled by the microprocessor 30 by control of the duty cycle of the pinched off state of the solenoid operated aspiration pinch valve 256. The microprocessor periodically pinches off the line 184 by addressing the valve 256 and causing it to pinch off the line, and later readdressing the same valve and causing it to open. When more flow rate is desired, the total pinched off time is reduced by reducing the "pulse width" of the pinch off time. In the Irrigation Only mode, zero flow is used, but this is controlled by a test in the interrupt 1 service routine testing the mode code to see if the machine is operating in Irrigation Only mode. This test is in the vacuum branch of the interrupt 1 service routine which is performed only in modes where vacuum is used. If the test answer is yes, the software sets the vacuum level at zero and ignores the potentiometer setting in the footswitch position sensor, so no aspiration flow results in Irrigation Only mode. In this instance, the test of step 400 is performed by a second microswitch in the footswitch which senses whether the footswitch is or is not depressed but is insensitive to the relative amount of depression compared to full scale. The step 406 is still performed, but it is ineffectual in that there is no vacuum force causing a flow to be modulated in the Irrigation Only mode. However, the code symbolized by the step 406 is needed for the other sub modes, so vectoring to the step 406 occurs from the other modes as well as symbolized by the vectors 408 and 410.

If processing was vectored to step 388, the first step is to determine if the footswitch is depressed in a step 412. When the footswitch is not depressed, the desired vacuum level number given to the D/A converter 42 on the line 59 indicates a zero desired vacuum level. This causes the solenoid operated valve 85 to cut off air flow through the venturi 65 thereby causing the vacuum line 63 to be vented to atmosphere as long as the valve 274 is open. If the footswitch is depressed, then a step 414 waits for it to be released by branching back to the step 412. If the footswitch is released, then the vacuum level is read in step 416 by reading the sensor 49 to test it for zero vacuum level, i.e., atmospheric pressure, in a step 418 as indicated by the vector 417. If the vacuum level is zero, the system is safe for a short transfer, and processing is vectored to a step 420 to close the aspiration pinch valve 256, open the transfer pinch valve 234 and apply a transfer vacuum to the vacuum line 244 as described previously and symbolized by the step 422. If the vacuum level is not zero, a test for timeout in a step 424 is performed to determine if too much time has elapsed from release of the footswitch, i.e., if the vacuum level has not fallen to zero within a certain time from release of the footswitch, an error has occurred and an error message must be displayed as symbolized by the step 426. If the vacuum level has not fallen to zero, and a timeout has not occurred, processing is vectored back to step 418.

After the short transfer of step 422, processing is vectored back to the step 406 where the flow rate is set for the particular mode the machine is currently operating in. The flow rate in all the I/A modes except the Irrigation Only mode is determined by reading the cut rate control 50 on the front panel. The number from the A/D converter 44 is then converted to a duty cycle for the aspiration pinch valve 256 to control the flow rate in accordance with the setting of the cut rate control. The step 430 reads the small bottle water sensor consisting of the probes 262 and 264 to determine if the cassette is full. If this test indicates the cassette is full, a complete transfer is performed in step 432. This step opens closes the pinch valves in the same manner as the short transfers described above, but maintains this transfer condition for 5 seconds. Simultaneously a "transfer" message is displayed. If the test of step 430 indicates a "not full" condition, another back up test is performed in step 434 to read the in line water sensor 63 to determine if the cassette is full and the probes 262 and 264 have failed to detect this fact due to corrosion or for some other reason. If this test indicates the cassette is full, a complete transfer is performed for eight seconds as indicated in step 436. Simultaneously a "check contact" message is displayed.

If the cassette is not full, then the cassette handling routine embodied in step 296 in FIG. 9B is performed to determine if the cassette is to be ejected.

Next a step 438 to update the maximum vacuum level desired is performed to insure that if the operator has changed the setting of the maximum vacuum control on the front panel, this will be noticed and the proper action taken. The step 440 reads the maximum vacuum level control on the front panel, while the step 442 displays this maximum desired vacuum level on the front panel display. The step 444 reads the actual vacuum level indicated by the sensor 49 and displays this value on the front panel display adjacent to the maximum vacuum level display area.

A step 440 performs an interrupt safety check as one of the final steps in the main loop of the I/A main mode routine. This step reads the interrupt safety variables and will set the machine to stop if the memory is damaged. The interrupt safety variable check consists of a check of the mode code to determine if it is out of range, a check of the A/D timing and a check of the vacuum venting timeout variable to insure it is a valid number. A loop return step 442 then vectors processing back to the step 364 to start the loop over again unless the mode check step indicates a mode switch is desired in which case the step 374 vectors processing to the warm start step 344 on FIG. 10A.

Figure 10D:
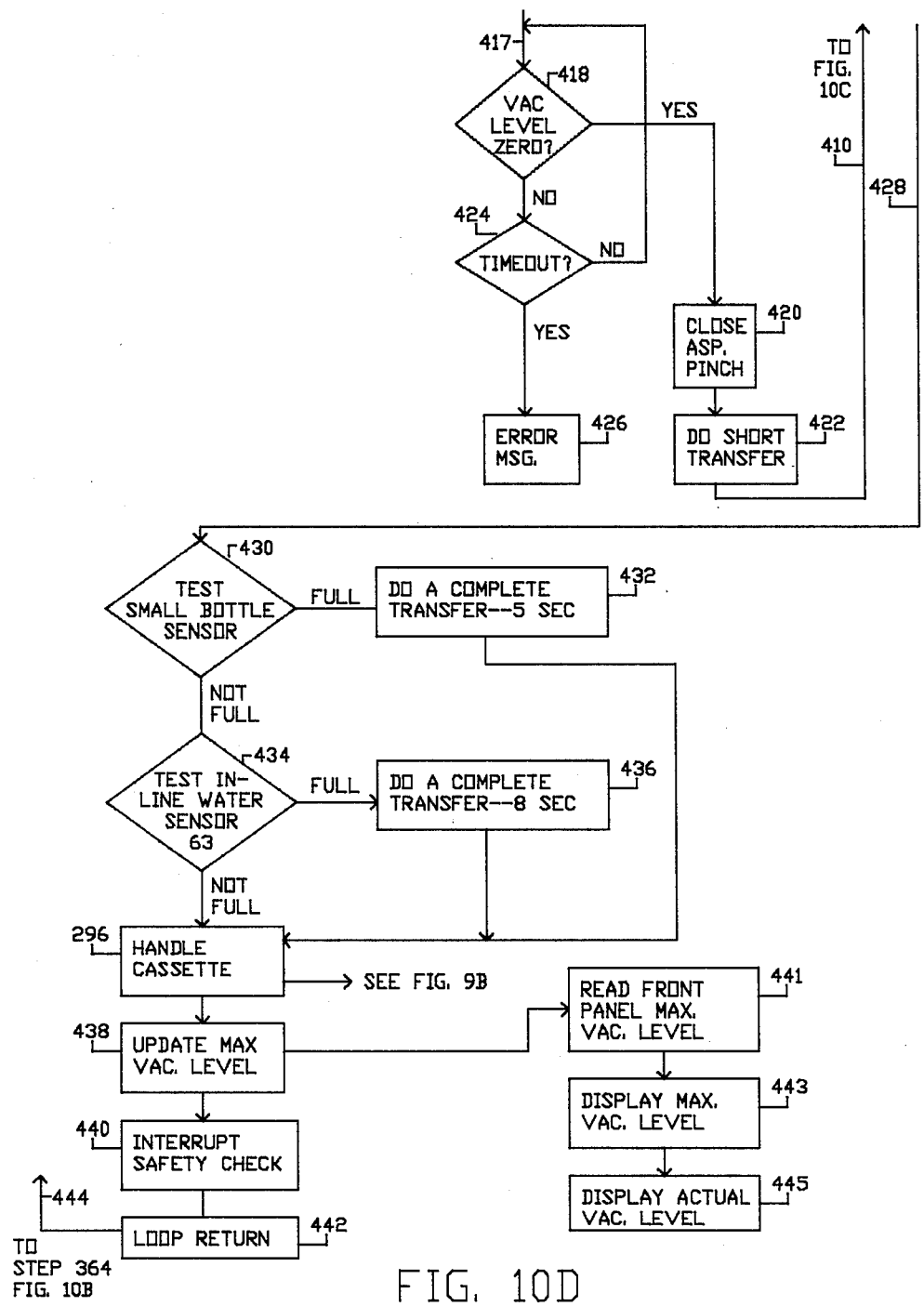
Figure 10E:
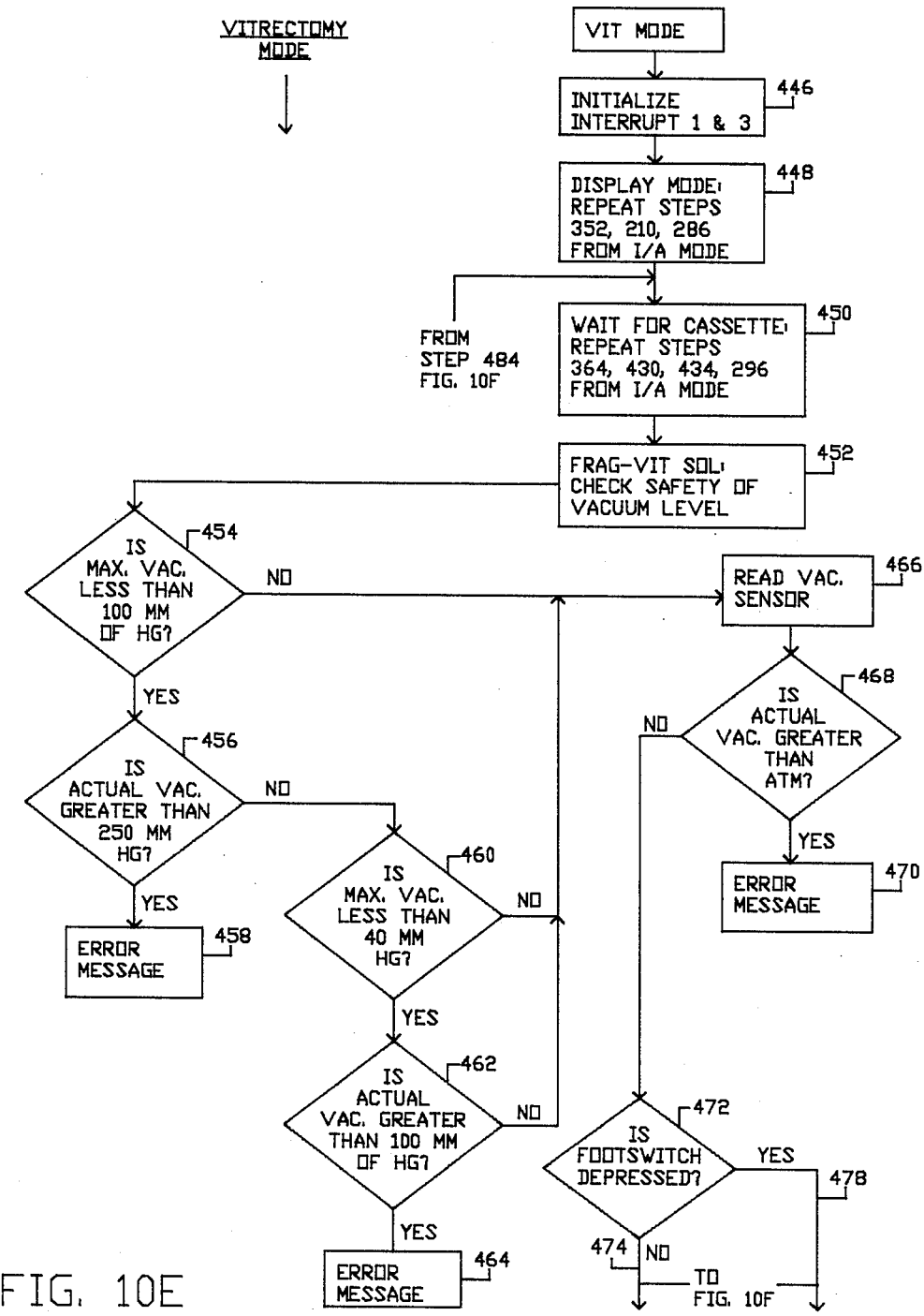

Referring to FIG. 10E there is shown a flow chart of the Vitrectomy Mode process control. The first step 446 is to initialize the interrupts to set the timers to the desired time between interrupts, and to set the time between updates of the displays and the frequency of updates of the cut rate bar graph display. Also, the interrupts are initialized to branch to the particular portion of the code in the service routine which pertains to that particular mode. This step is the same as the step 350 in the I/A mode. Next, in a step 448, the steps 352, 210 and 286 and all their substeps from the I/A mode are repeated to display the name of the mode, wait for cassette insertion, test the vacuum integrity of the cassette and vent the vacuum after the test. Next, the step 450 is performed to repeat the steps 364, 430, 434 and 296 from the I/A Mode and all their substeps to check for a change of mode by reading the keyboard, read the water sensor 68 and the water sensor in the top of the small bottle and perform any liquid transfers if necessary, and to poll the cassette eject switch 62 to determine if the operator desires to eject the cassette.

In the Vitrectomy mode the cut rate of the probe is controlled by the interrupt 3 service routine and the vacuum level is controlled by the interrupt 1 service routine. The main loop of the vitrectomy routine, which starts with the step 450, provides auxiliary support to these functions controlled by the interrupts. The first of these auxiliary functions is to monitor the safety of the vacuum system to insure that it is within acceptable limits. The first test in step 454 is to read the setting of the maximum vacuum control 46 and compare it to a constant of 100 millimeters of mercury (mm of Hg). If the answer is yes, the test of step 456 is performed to read the vacuum sensor 49 indicating actual vacuum level to determine if it is higher than 250 mm of Hg. If the answer is yes, an error message is displayed in step 458. If the answer is no to the test of step 456, the test of step 460 is preformed to determine is the maximum vacuum level is less than 40 mm of Hg. If the answer to this test is yes, then the test of 462 is performed to determine if the actual vacuum level is greater than 100 mm of Hg. If it is, then an error message is displayed in step 464. If the answer to any of the tests 454, 460 or 462 is no, then the vacuum sensor 49 is read in a step 466. The actual vacuum level is then compared to atmospheric pressure in step to determine if the actual vacuum level is actually positive pressure greater than atmospheric pressure which would indicate something is wrong. If the answer is yes, an error message is displayed in step 470. If the answer is no, then the test of step 472 is performed to determine if the footswitch is depressed. If the answer is that the footswitch is not depressed, then processing is vectored by the vector 474 to a step 476 to do a short transfer in the manner described above. After the short transfer is performed, the maximum vacuum level is updated in a step 477 by repeating the steps 440, 442 and 444 from FIG. 10D. Then processing is vectored to a step 480 to be described below.

If the footswitch is depressed, processing is vectored by the vector 478 to the step 480 to update the cut rate. This process involves reading the cut rate control 50 in a step 482 and updating the cut rate bar graph display in a step 484. Finally, in step 485, the interrupt safety check of step 440. FIG. 10D is repeated. Processing is then returned to the step 450 in FIG. 10E to repeat the main loop of this Vitrectomy Mode. All throughout this Vitrectomy mode, vacuum control and probe cutting speed control is exercised by interrupts 1 and 3.

Figure 10F:
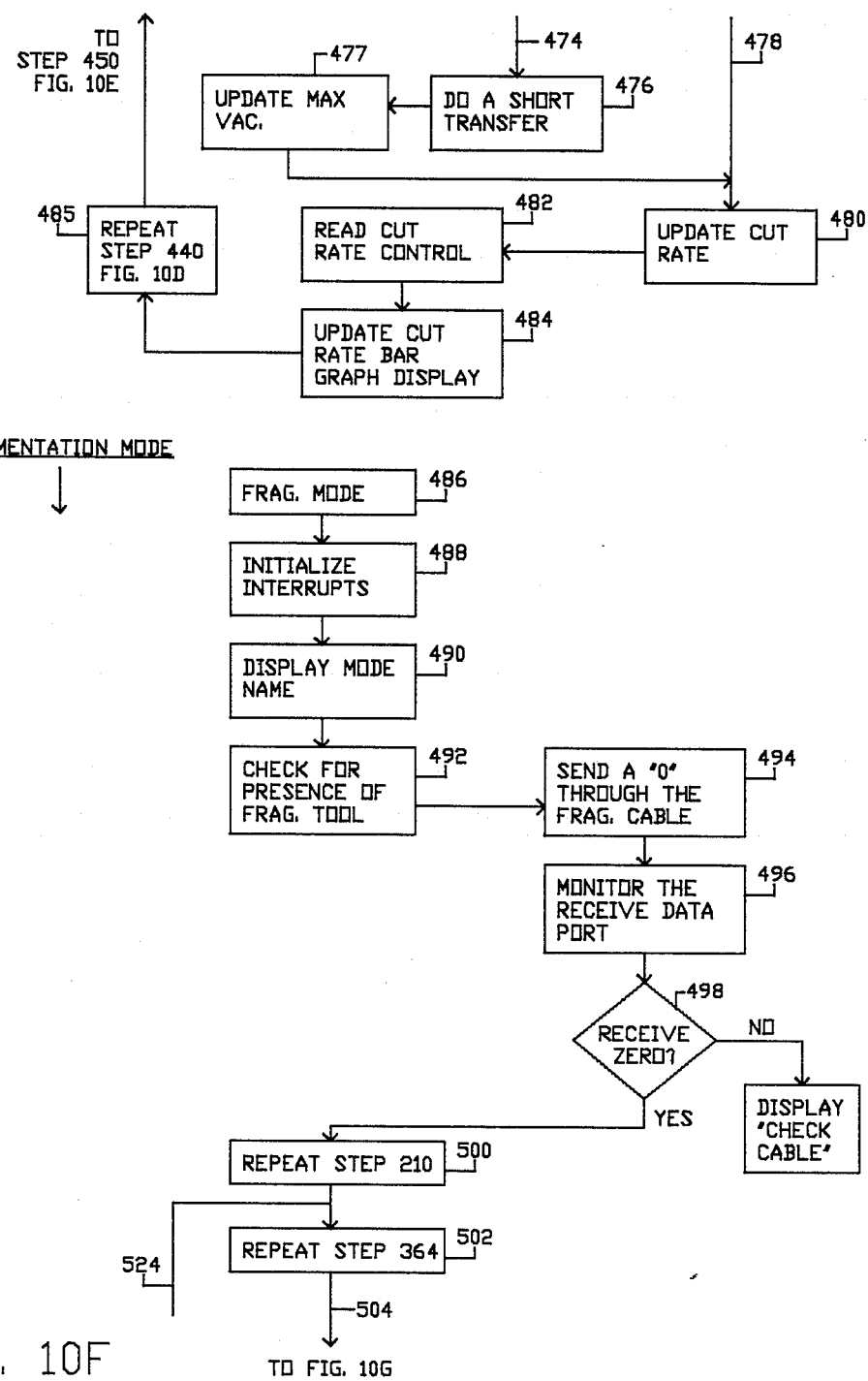
Figure 10G:
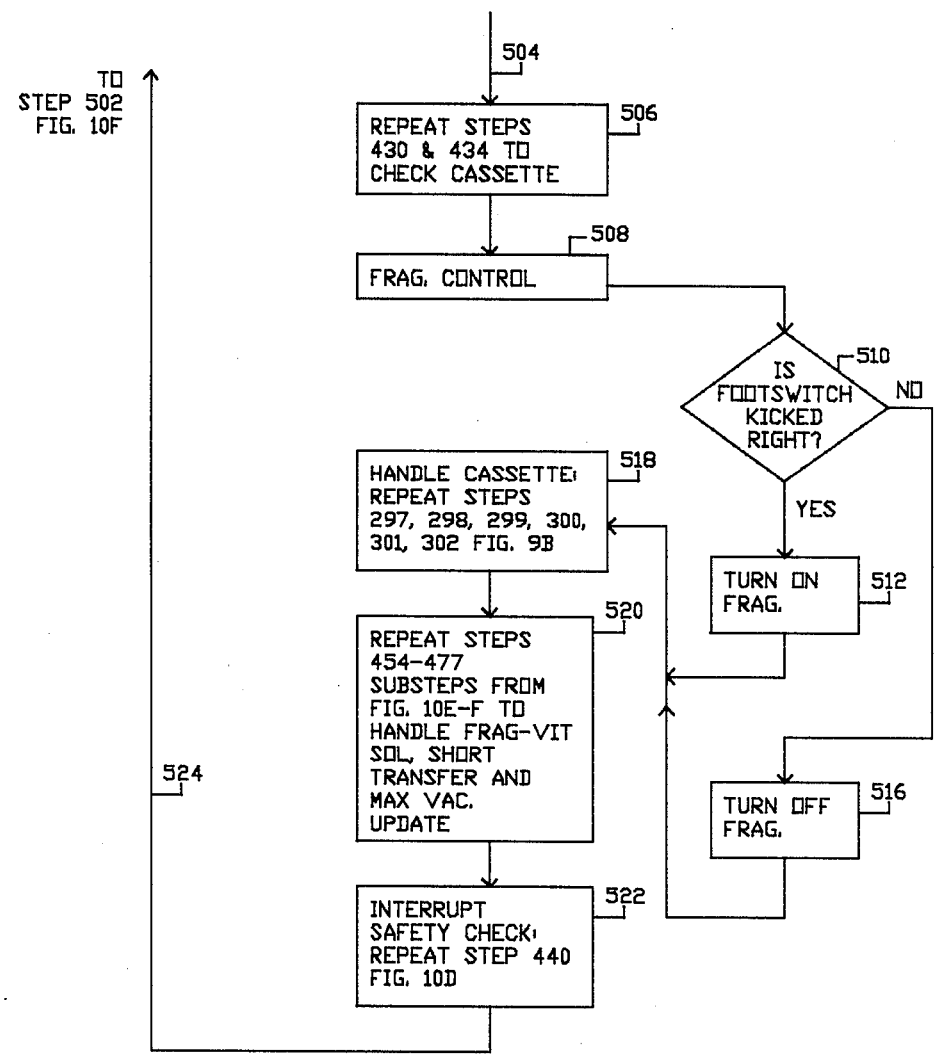

If the mode code is Frag Mode, then processing is vectored to step 486 on FIG. 10F. The first step in this mode routine is to initialize interrupt 1 by setting its timer to the proper interval and setting the interrupt mode variable to vector processing in the interrupt service routine to the proper code to handle this mode. Next, in step 490, the mode name is displayed, and in step 492 the fragmentation tool's presence is checked. The step 492 is comprised of the substep 494 to transmit a logic zero through the frag cable through the transmit data serial port on the microprocessor. The receive data port on the microprocessor is monitored in the step 496 for return of the zero transmitted in the step 494. The step 498 tests for receipt of the zero returned from the frag tool, and displays an error message if the zero is not returned, and vectors processing to the next step in the Frag Mode if the zero is returned.

Next, the step 500 repeats the step 210 and its substeps to wait for the cassette to be placed in the receptacle on the front panel. The step 502 then repeats the step 364 and its substeps to check the keyboard for a mode change. Processing is then vectored to a step 506 which checks the small bottle in the cassette for fullness and initiates liquid transfers if it is full by repeating steps 430 and 434 and their substeps.

The step 508 controls the fragmentation tool by turning on and turning off the tool depending upon the state of the footswitch 48. The first substep in the process of step 508 is to read the microswitch on the footswitch which senses left or right placement of the footswitch. This test is performed in step 510, and a step 512 turns on the frag handtool if the answer to the test of 510 is yes. After performing the step 512 processing is vectored to a step 518 to handle the cassette which step will be described below.

If the test of step 510 indicates that the footswitch is not kicked right, processing is vectored to a step 516 which turns off the frag tool and vectors processing to the step 518 which repeats the cassette handling steps of FIG. 9B to determine if the cassette eject button has been pushed and whether it is safe to eject the cassette. Next, in step 520 the vacuum levels are checked for errors, a short transfer from the small bottle to the large bottle is performed if the footswitch is not depressed, and the maximum vacuum is updated by repeating steps 454-477 of FIGS. 10E-F described above. Finally, the interrupt safety check is performed in step 522 by repeating step 440 from FIG. 10D. The main loop is repeated by the vector 524 which returns processing to step 502. FIG. 10F. All throughout the Fragmentation mode, interrupt 1 is exercising control over the vacuum level.

Figure 10H:
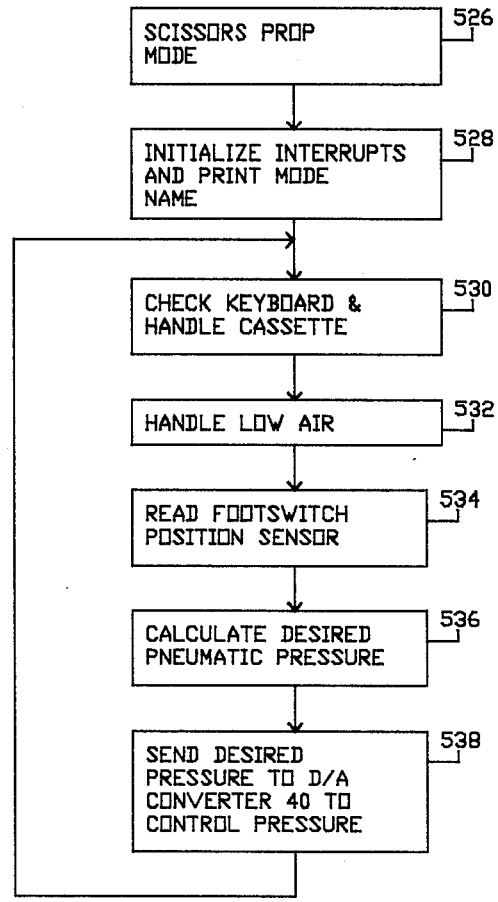

If the branch in step 348 was to the Scissors Proportional Cut Mode, then processing is vectored to step 526 on FIG. 10H. In this mode, pneumatic pressure is applied to a pneumatically driven scissors handpiece. The amount of pressure applied is proportional to the position of the footswitch. The maximum pressure that can be applied is 20 psi in the preferred embodiment. The first step 528 is to initialize the interrupts and to print the mode name on the front panel display. The only interrupt used is interrupt 1, and it only updates the software timers which control how often the displays are updated since no vacuum is used in this mode at all. Next, in step 530, the keyboard is checked for a mode change, and the front panel cassette eject switch is checked to determine if the cassette is to be ejected and whether it would be safe for such an action all as described above with respect to previous modes. This step also checks to determine is a cassette is near by reading the proximity switch 64, and if it is the proper commands are issued to grab the cassette as described above, but the vacuum check steps described above are omitted. In step 532, the input pneumatic air pressure is checked, by reading the input air pressure sensor 70 in FIG. 2 to insure that there is adequate air pressure. The step involves addressing the sensor, reading its output, testing the result and branching to an error display if the pressure is inadequate.

The main step in this mode is step 534 which reads the footswitch position sensor to determine the desired amount of cutting pressure. The position sensor is read through the A/D converter as previously described. A step 536 calculates the desired pneumatic pressure by multiplying constant of 20 psi times the fraction of the total footswitch position sensor displacement relative to full scale. The result is sent to the D/A converter 40 where it is converted to an analog "desired pressure" signal on the line 123. This signal control the linear valve 149 to cause the desired pneumatic pressure to be output to the scissors handpiece.

Figure 10I:
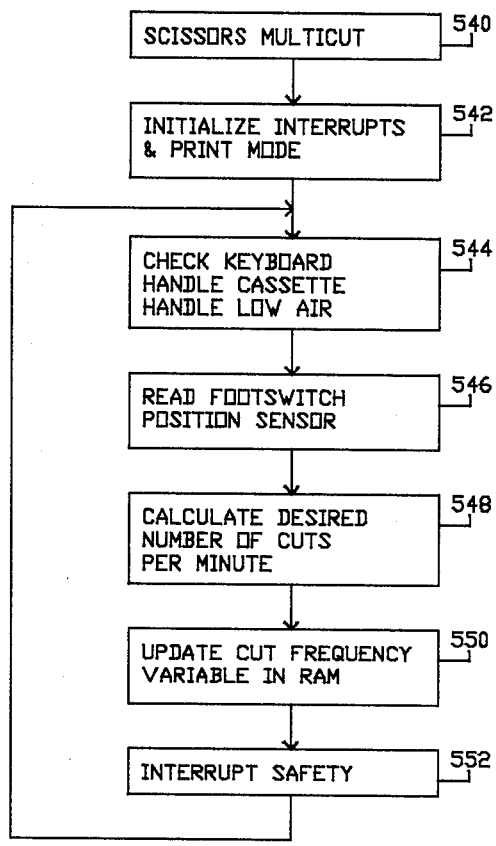

If the step 348 in FIG. 10B results in a branch to the Scissors Multicut Mode, then the step 540 in FIG. 10I is reached. In this mode, the pneumatic scissors handpiece is driven with a triangular pneumatic waveform having a constant amplitude, and having a frequency controlled by the footswitch position sensor. Interrupt 3 is not used in this mode, and interrupt 1 is used to control the linear valve 149 to cause the pneumatic pressure to be updated 100 times per second to implement the triangular pneumatic waveform. The first step 542 is to initialize the interrupts 1 and 3 such that interrupt occurs 100 times per second, and interrupt 3 does not occur at all. This step is the same as step 528 in FIG. 10H. Next, a step 544 is performed which is the same as steps 530 and 532 in FIG. 10H to determine if the cassette eject switch has been pushed and to determine if it is safe to eject the cassette, to check the keyboard for changes in mode and to make sure that there is adequate air pressure to handle the needs for the scissors handpiece. The cassette proximity switch is read also, and the cassette is drawn in if it is near as was described above for the Scissors Proportional Cut Mode. No vacuum is needed in this mode.

The main step in the Scissors Multicut Mode is step 546 wherein the footswitch position sensor is read in order to calculate the frequency of the triangular pneumatic waveform. The calculation of the desired number of cuts per minute is performed in the step 548 wherein a constant of 60 cuts per minute is multiplied by the fraction of the total possible displacement of the footswitch position sensor found when the position sensor was read. Once the desired frequency is calculated, a number representative of that frequency is updated in RAM in step 550. This cut frequency variable is read upon every occurrence of interrupt 1 and determines the step size as will be apparent from the discussion of interrupt 1 given below. After updating the cut frequency variable, the step 522 performs the interrupt safety check step described above in connection with discussion of the other modes. Then processing returns to the step 544 for another pass through the main loop.

Referring to FIG. 11, there is shown a flow chart of the service routines of interrupts 1 and 3. Interrupt 1 is detailed starting in FIG. 11A with a step 554 which an interrupt 1 timeout and vectoring to the interrupt 1 service routine. A step 556 follows which is an update of the sofware timers that time the frequency of updates of the displays and the cut rate bar graph. This update involves reading a variable from RAM which is set when a particular mode is entered to indicate the desired update rate for each display during the particular mode.

Each interrupt service routine contains code which is peculiar to only some modes. Not all code in each service routine is performed for any particular mode. To determine which portion of the service routine for the current mode, a step 558 is performed. This step checks an interrupt mode variable in RAM which is set by the mode change routine each time a new mode is entered. This variable indicates which portion of the service routine of each interrupt is relevant to the particular mode in which the machine is currently operating. After the interrupt mode variable is checked, a stop 560 causes branching to the relevant portion of the service routine.

If a mode involving vacuum control is the current mode, branching to a step 562 occurs. This step updates a buzzer which provides audible feedback to the surgeon which, by its frequency, indicates the current level of actual vacuum.

Next, a step 564 tests the current mode code to determine if the Irrigation Only Mode has been selected. This mode does not involve vacuum, so if the answer is yes, a step 566 is performed which sets the vacuum level to zero and ignores the footswitch position sensor position. The microswitch in the footswitch position sensor which indicates whether the footswitch is depressed, but does not indicate how far is then read in a step 567. The result is stored in RAM for testing by the test 400 in FIG. 10C for control of the irrigation pinch valve. If the answer is no, then the step 568 is performed to read the footswitch position. This number is stored in RAM pending a calculation. Next a the maximum vacuum control 46 is read, and the result is stored in memory in a step 570.

The microprocessor then calculates the desired level of vacuum for modes in which the footswitch position controls the desired vacuum level in a step 572. In the Irrigation And Aspiration Mode, the calculation is performed as in the step 574 where a constant of 550 millimeters of mercury is multiplied by the fraction of total scale found for the maximum vacuum control in step 570, the result then being multiplied by the fraction of total scale of the footswitch position sensor found in step 568. If the Vitrectomy Mode or Frag Mode is the current operating state, then the calculation is performed as in the step 576. This calculation is a multiplication of a constant of 400 millimeters of Mercury times the fraction of total scale found for the maximum vacuum control in step 570, the result then being multiplied by the fraction of total scale of the footswitch position sensor found in step 568. Next a step 577 is performed to read the actual vacuum from the sensor 49 and update an actual vacuum variable in RAM. The last vacuum control step 576 is to send the result of the calculation of step 572 to the D/A converter 42 in FIG. 1 to cause the vacuum control linear valve to generate the desired vacuum level. The service routine then ends, and processing resumes where it left off when the interrupt occurred as symbolized by step 578.

If the result of the step 560 is a branch to the scissors mode, the vector 580 causes a step 582 which is a test for whether the multicut or proportional cut mode is desired. If the multicut mode is desired, a step 584 is performed to read the cut frequency variable in RAM determine the frequency desired for the pneumatic triangular waveform as set by the step 550 in FIG. 10I.

After the desired frequency is determined, a step 586 is performed to calculate the step size and the new pressure level. The triangular pneumatic waveform is generated by incrementing or decrementing the desired pressure level signal sent to the D/A 40 100 times per second by a variable step size. The size of the step determines the frequency of the triangular waveform as follows. A maximum pressure level of 20 psi is predefined, and when incrementation causes the new pressure level to equal or exceed this pressure ceiling, then the microprocessor reverses the trend and begins decrementing the current pressure level by steps until zero pressure is reached whereupon incrementation is started again. The desired frequency is obtained by changing the step size such that these limits are reached sooner or later. The step 586 represents a step of comparing the desired frequency to the current frequency and either increasing the step size or decreasing the step size depending upon the result. Once the new step size is determine, the step value is added to or subtracted from the current pressure to derive the new pressure. Whether the step is added or subtracted depends upon the current direction, i.e., whether the waveform is on the positive or negative slope leg, and upon whether the new pressure is outside the 0 psi and 20 psi limits. After determining the new pressure, the updated value is sent to the D/A 40 to properly adjust the linear valve 149 in step 588, and step 590 cause return from the service routine to the main loop of the mode routine.

If the test of step 582 indicates the proportional cut mode is the current mode, the interrupt 1 service routine has no major function since the job of reading the footswitch and controlling the linear valve is left to the main loop of the mode routine. In this case, a step 592 turns off the vacuum and updates the software timers controlling the display update frequency for this mode. Thereafter the step 590 is performed to return to the main loop.

Figure 11A:
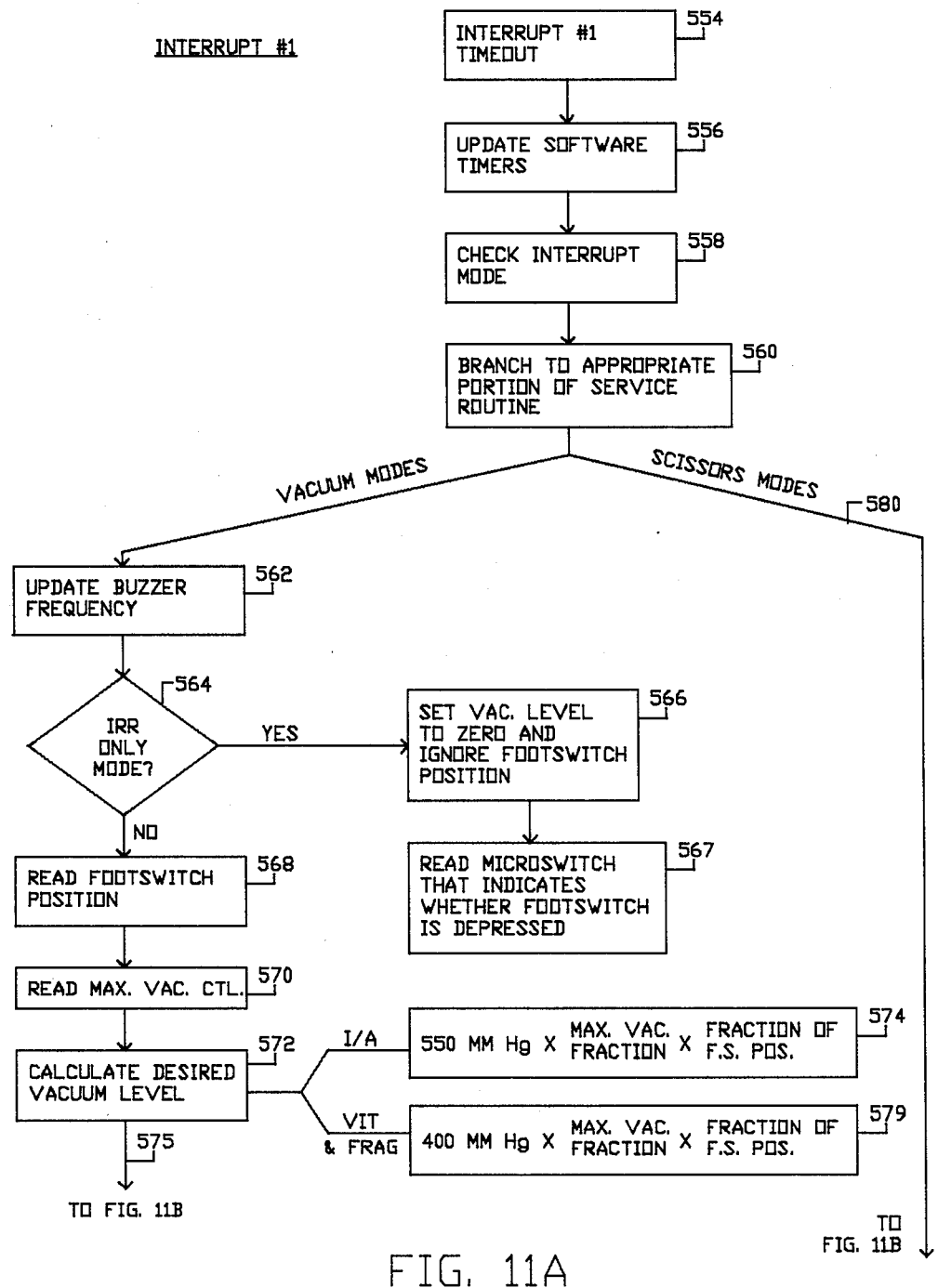
FIGS. 11A-D is a flow chart of the two main control interrupts which are used in controlling the modes.
Figure 11B:
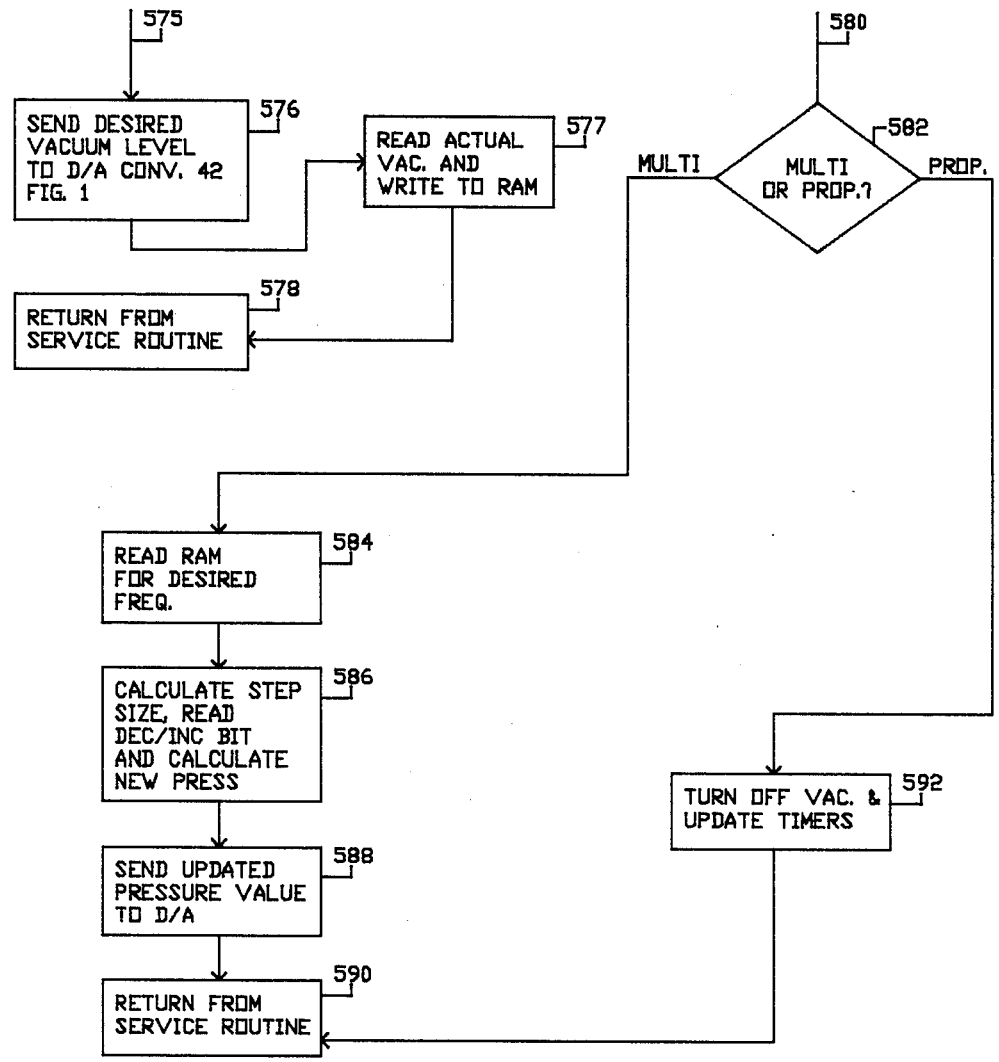
Figure 11C:
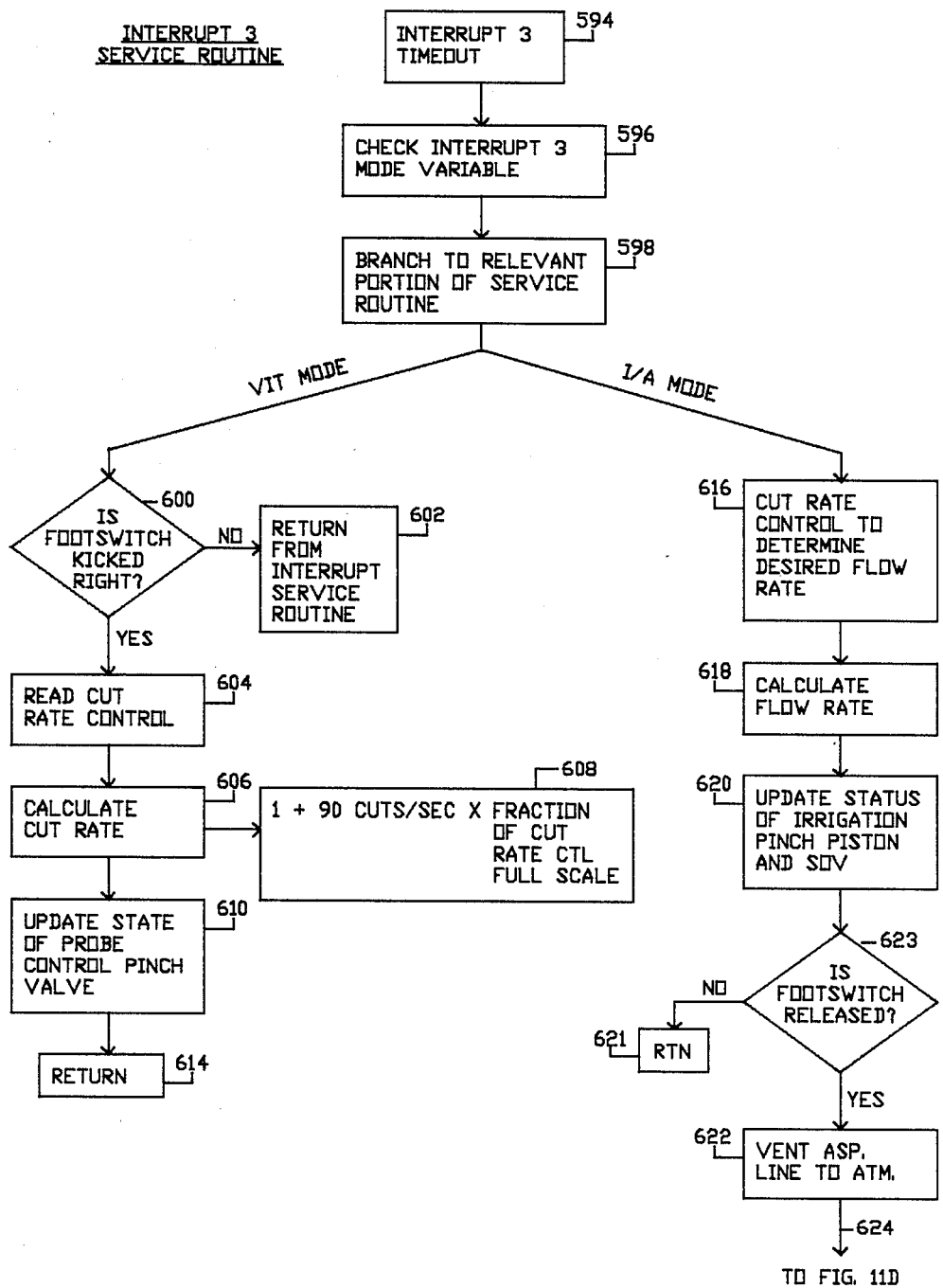
Figure 11D:
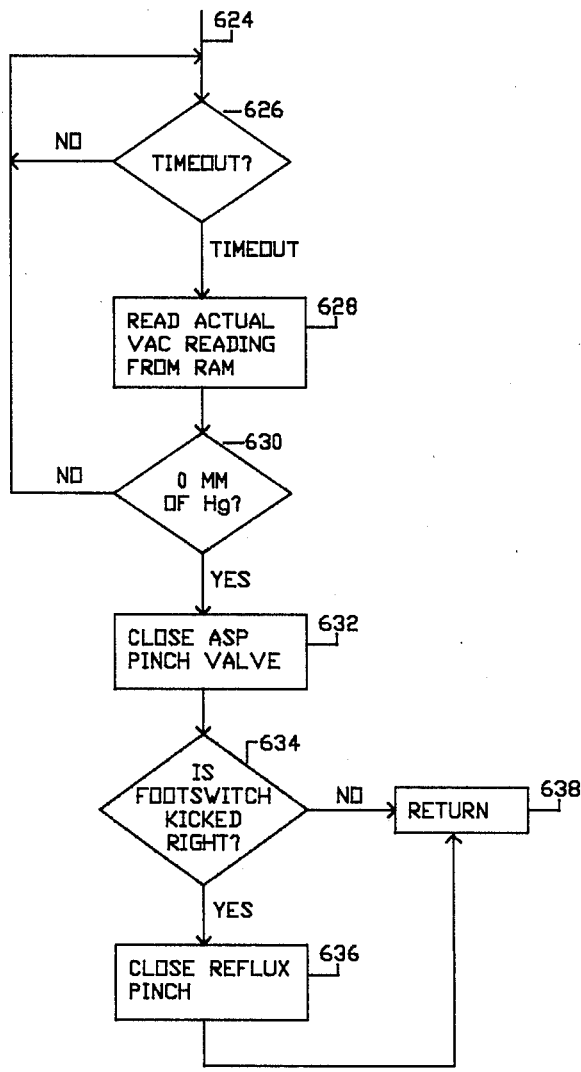

Referring to FIG. 11C there is shown the beginning of the interrupt 3 service routine. The step 594 represents the occurrence of an interrupt 3 timeout by the software timer which generates the interrupt 3 interrupt request. A step 596 is then performed which checks the interrupt 3 mode variable to determine the relevant code in the interrupt 3 service routine which pertains to the particular mode in which the machine is operating. After the relevant portion of the service routine is determined, that code is branched to in the step 598. If the Vit Mode is selected, interrupt 3 performs control of the vitrectomy probe cut rate by reading the cut rate control 50 on the front panel and calculating the desired cut rate. The first step in this process is a step 600 which tests the footswitch to determine if it is kicked right indicating that the surgeon wishes the vitrectomy probe to begin cutting at the rate set by the cut rate control on the front panel. If the footswitch is not kicked to the right, no cutting is desired at that time, and branching to a step 602 occurs which causes a return from the interrupt 3 service routine to the main loop of the Vit Mode at whatever step was next to be performed when the interrupt occurred.

If the footswitch is kicked right, a step 604 is performed to read the cut rate control 50. This is done as described earlier herein. Basically all the analog potentiometers are read by sending a constant current through one end of the potentiometer to the wiper and reading the voltage across the potentiometer to the wiper. Next, a step 606 is performed to calculate the cut rate. This is done as illustrated in the step 608 where the equation for the calculation is given. The minimum cut rate is one cut per second for the cut rate control fraction of 0% of full scale. The maximum cut rate is 10 cuts per second for a 100% setting of the cut rate control. In between these two extremes, the cut rate is one plus the quantity equal to the percentage of full scale read from the cut rate control times a constant of 9 cuts per second. Finally, the state of a probe control solenoid operated valve 612 in FIG. 2 is updated in a step 610. This valve couples the pneumatic pressure line 143 to the vit cutter probe, and can be opened and closed via the control bus 206 and the RAM and I/O ports 74 in FIG. 1. The frequency of the vit cutter probe is controlled by controlling the pulse width of the pneumatic air pressure pulses which are generated by the microprocessor by opening and closing the the valve 612. Higher frequencies are implemented by making the pneumatic pulses shorter in duration. Thus, the microprocessor takes the result of the calculation in step 606 and calculates the pulse width needed to implement this frequency. It then examines data it maintains on the position of the valve 612 to determine how long it has been open or closed and compares this information to the desired pulse width. From this comparison, it makes the determination whether to open or close the valve 612, and sends the proper data to the RAM and I/O port for the valve 612 to open or close it. The last step is to return from the service routine in a step 614.

If the branch of step 598 is to the I/A Mode, the service routine for interrupt 3 controls the irrigation flow rate, aspiration line venting and the reflux function. The first step in this process is a step 616 which reads the cut rate control 50 to determine the desired irrigation flow rate. This control 50 has dual functions depending upon which mode the machine is in. Next the desired flow rate is calculated in a step 618. This step involves adding to a minimum flow rate of 10% the quantity equal to 100% of the flow rate times the fraction of the cut rate control full scale setting which was read in the step 616. The final step in controlling the flow rate is to update the status of the flow rate pinch valve and pinch piston 89 in FIGS. 1 and 2 through the RAM and I/O ports 74 and the control buses 84 and 206. The irrigation pinch piston is controlled by the microprocessor to pinch off the surgical tubing carrying the irrigation solution at a constant frequency of 2 pulses per second. The flow rate is controlled by modulating the pulse width based upon the result obtained in the step 618. The updating step of comparing the data on the current status of the irrigation pinch piston to the desired pulse width and sending the proper command to the solenoid operated valve 352 in FIG. 2 is symbolized by the step 620.

A step 620 is the first step in the vacuum venting control. Every time the footswitch is released, the aspiration line 184, the small bottle, and the aspiration line 63 must be vented to atmosphere. This is done by insuring that the solenoid operated valve 274 in FIG. 2 is open, and by closing the solenoid operated linear valve 85 to block pressurized air flow through the venturi 65. This vents the aspiration circuit mentioned above through the throat of the venturi. The first step in this process is the test 620 to determine if the footswitch is released. If it is not released, a return from the service routine to the main loop of the mode is performed in a step 621. If it is released, a step 622 is performed to vent the aspiration circuit named above by addressing the proper valves mentioned above and writing the proper data to the I/O port and to the D/A converter 42 to cause the valves to assume the proper states as detailed above. Processing is then vectored by the vector 624 to a test 626.

The test 626 is a test for a timeout by an internal interrupt timer which is set to zero count when the footswitch is released. If this timer has timed out, a step 628 is performed which reads the actual vacuum level variable in RAM which is updated in the interrupt 1 service routine each time interrupt 1 occurs. A test is then performed in step 630 which determines whether the actual vacuum level has fallen to 0 mm of Hg. If it has, then processing proceeds to a step 632 to begin reflux control. If it has not, processing is vectored back to the step 626 to wait for another timeout. The purpose of this loop is to wait for the actual vacuum level to drop to atmospheric pressure to insure that the vacuum system is safe for reflux if desired.

A reflux is performed every time the footswitch is released after the vacuum has been vented if the footswitch is kicked right. The first step in this process is step 632 to close the aspiration pinch valve 256 in FIG. 3 to prevent the hydraulic pressure to be applied by the reflux pinch process from propagating into the machine as well as toward the handtool. Next, in step 634, the footswitch microswitch is read to determine if the footswitch is kicked right. If it is, the reflux pinch valve 92 in FIG. 3 is addressed and closed to cause the reflux. Thereafter a return to the main loop of the mode is made via a step 638. If the footswitch is not kicked right, no reflux is desired, and a return from the service routine to the main loop of the mode is made in the step 638.

Although the invention has been described in terms of the embodiment described above, it will be apparent to those skilled in the art that numerous modifications can be made such as by changing the order of steps in the control process or eliminating steps or items of circuitry or mechanical implements. All such modifications, if they fall within the spirit of the invention are intended to be covered by the claims set out below.

Appendix A

```
000000: 02 1D 34 C3 EF 9D FF EE 9C FE 22 02 1C A8 A3 E0     ..4......"....
000010: 04 F0 70 06 12 1D 18 E0 04 F0 22 02 1C C3 FF FF    ..P......."....
000020: 4D 56 53 20 2D 20 58 49 49 20 20 56 20 31 2E 31    MVS - XII  V 1.1
000030: 43 6F 70 79 72 69 67 68 74 20 20 31 39 38 34 20    Copyright  1984
000040: 62 79 20 4D 49 44 20 4C 61 62 73 2C 49 6E 63 2E    by MID Labs,Inc.
000050: 52 65 70 72 6F 64 75 63 74 69 6F 6E 20 20 20 20    Reproduction
000060: 50 72 6F 68 69 62 69 74 65 64 20 20 62 79 20 20    Prohibited  by
000070: 4C 61 77 2E 2A 2A 2A 2A 2A 2A 2A 2A 2A 2A 2A 2A    Law.************
000080: 75 33 01 75 88 02 75 8D 00 75 A0 00 75 89 10 75    u3.u..u..u..u..u
```

```
000090: 88 00 D2 03 E5 18 84 FF 2A E5 43 44 80 F5 43 E5    ........*.CD..C
0000A0: 43 90 C4 04 F0 75 19 00 E5 19 D3 94 07 50 13 E5    C....u.......P..
0000B0: 19 90 C0 00 12 1D 28 74 20 F0 78 19 74 01 26 F6    ......(t .x.t.&.
0000C0: 50 E6 22 E5 43 54 FC F5 43 E5 43 90 C4 04 F0 75    P.".CT..C.C....u
0000D0: 24 02 85 18 32 75 88 40 75 A8 88 22 90 E1 02 E0    $...2u.@u.."....
0000E0: 44 01 90 E1 02 F0 E5 18 60 25 15 18 75 1A 01 75    D.......`%..u..u
0000F0: 19 00 AE 19 AF 1A 74 58 C3 9F 74 02 9E 40 05 78    ......tX..t..@.x
000100: 1A 74 01 26 F6 50 04 18 E4 36 F6 50 E5 80 D7 22    .t.&.P...6.P..."
000110: E5 43 54 FC F5 43 E5 43 90 C4 04 F0 E5 18 75 F0    .CT..C.C......u.
000120: 08 A4 FF AE F0 9F 18 75 19 00 E5 19 D3 94 07 50    .......u.......P
000130: 1B E5 18 25 19 90 19 E0 93 FE 75 19 90 C0 00 12    ...%......u.....
000140: 1D 28 EE F0 78 19 74 01 26 F6 50 DE 22 75 18 00    .(..x.t.&.P."u..
000150: E5 18 D3 94 07 50 13 E5 18 90 C0 00 12 1D 28 74    .....P........(t
000160: 20 F0 78 18 74 01 26 F6 50 E6 22 75 A8 00 E5 43     .x.t.&.P."u...C
000170: 44 80 F5 43 E5 43 90 C4 04 F0 90 F0 01 E4 F0 90    D..C.C..........
000180: F0 03 E4 F0 90 F0 02 E4 F0 D2 97 D2 96 90 E1 03    ................
000190: E0 54 FD 44 08 90 E1 03 F0 90 E1 03 E0 44 10 90    .T.D.........D..
0001A0: E1 03 F0 90 C4 05 E4 F0 90 E1 02 E0 44 01 90 E1    ............D...
0001B0: 02 F0 75 18 07 12 01 10 E5 1A 75 F0 0A 84 AF F0    ..u.......u.....
0001C0: 7E 00 EF 24 30 90 C0 07 F0 E5 1A 75 F0 0A 84 FF    ~..$0......u....
0001D0: 7E 00 EF 24 30 90 C0 06 F0 B0 FE 90 E1 01 E0 54    ~..$0..........T
0001E0: 02 70 2D 90 E0 07 E0 14 F0 90 C4 05 E4 F0 90 C4    .p-.............
0001F0: 05 E4 F0 90 E1 01 E0 54 02 70 06 75 1A 0D 12 01    .......T.p.u....
000200: 6B 90 E0 07 E0 C3 94 F0 50 06 75 1A 0F 12 01 6B    k.......P.u....k
000210: 22 75 1C 01 75 1B 00 AE 1B AF 1C 74 28 8E 00 15    "u..u......t(...
000220: 9F 40 12 30 92 01 22 78 1C 74 01 26 F6 50 04 18    .@.0.."x.t.&.P..
000230: E4 36 F6 50 E2 75 1A 0B 12 01 6B 22 75 89 01 75    .6.P.u....k"u..u
000240: 8A 02 75 8C F1 75 A8 82 75 B8 02 22 E5 36 C3 94    ..u..u..u.."6..
000250: 0A 50 01 22 75 36 00 30 93 06 E5 22 64 03 60 0E    .P."u6.0..."d.`.
000260: E5 22 C3 94 02 40 07 E5 22 D3 94 03 40 17 E5 31    ."...@.."...@..1
000270: FF 7E 00 0F BF 00 01 EE 74 1D 12 1D 0A 0E 8E 1E    .~......t.......
000280: 12 1A 81 80 03 12 1A 66 22 E5 2D D3 94 01 40 53    .......f".-...@S
000290: E5 2C D3 94 28 50 07 E5 2D D3 94 73 50 2D E5 2C    .,..(P..-..sP-.,
0002A0: D3 94 10 50 07 E5 2D D3 94 37 50 07 A2 94 B3 92    ...P..-..7P.....
0002B0: 97 80 16 D2 97 74 0A F5 18 12 00 DC E5 2D D3 94    .....t.......-..
0002C0: 37 40 06 75 1A 06 12 01 6B 80 16 D2 97 74 0A F5    7@.u....k....t..
0002D0: 18 12 00 DC E5 2D D3 94 73 40 06 75 1A 06 12 01    .....-..s@.u....
0002E0: 6B 80 20 D2 97 74 0A F5 18 12 00 DC E5 2D C3 94    k. ..t.......-..
0002F0: 02 50 10 90 E1 03 E0 44 20 90 E1 03 F0 75 1A 02    .P.....D ....u..
000300: 12 01 6B 22 30 94 03 02 03 9F 90 CC 00 E0 F4 54    ..k"0..........T
000310: 0F F5 25 90 CC 00 E0 F4 54 0F 65 60 03 75 25 25    ..%.....T.e`.u%%
000320: 00 E5 25 B4 01 0C 12 14 C9 E5 22 D3 94 01 40 02    ..%......."...@.
000330: 80 6E E5 25 70 19 E5 22 70 05 A2 93 B3 40 02 80    .n.%p.."p....@..
000340: 02 80 63 E5 22 B4 01 03 20 93 02 80 02 80 57 E5    ..c."... .....W.
000350: 22 C3 94 06 50 47 E5 25 54 0E F5 25 E5 25 60 3B    "...PG.%T..%.%`;
000360: E5 22 90 0C 78 F8 28 28 73 E5 25 64 04 60 02 80    ."..x.((s.%d.`..
000370: 35 80 28 E5 25 64 04 60 02 80 2B 80 1E E5 25 64    5.(.%d.`..+...%d
000380: 02 60 02 80 21 80 14 E5 25 64 08 60 02 80 17 80    .`..!...%d.`....
000390: 0A 80 13 E5 25 64 FF 60 02 80 0B 80 02 80 0D 22    ....%d.`......."
0003A0: 90 07 8B 12 1D 45 90 07 FA 12 1D 45 90 0C 47 12    .....E.....E..G.
0003B0: 1D 45 30 01 01 22 90 CC 00 E0 54 20 60 06 75 18    .E0.."....T `.u.
0003C0: 06 12 00 80 12 03 04 90 E1 03 E0 44 02 90 E1 03    ...........D....
0003D0: F0 90 CC 00 E0 FE 90 CC 00 E0 4E 54 20 60 0C 90    ..........NT `..
0003E0: E1 03 E0 44 04 90 E1 03 F0 80 D9 90 E1 03 E0 54    ...D...........T
0003F0: FD 90 E1 03 F0 74 0A F5 18 12 00 DC 90 CC 00 E0    .....t..........
000400: FE 90 CC 00 E0 4E 54 20 60 02 80 B8 90 E1 03 E0    .....NT `.......
000410: 54 FB 90 E1 03 F0 75 18 FF 12 00 80 90 CC 00 E0    T.....u.........
000420: 54 40 60 0D 75 18 01 12 00 80 74 82 F5 46 12 15    T@`.u.....t..F..
000430: 1C 12 16 A6 22 90 CC 00 E0 54 20 60 10 90 CC 00    ...."....T `....
000440: E0 54 20 60 08 90 CC 00 E0 54 20 70 02 80 26 E5    .T `.....T p..&.
000450: 22 D3 94 01 40 0A 22 94 05 12 14 C9 80 35 80 13    "...@."......5..
000460: 90 E1 03 E0 54 04 FF 7E 00 EF 60 01 22 20 94 03    ....T..~..`." ..
000470: 12 14 C9 80 1D 90 E1 03 E0 54 04 FF 7E 00 EF 60    .........T..~..`
000480: 11 74 0A F5 18 12 00 DC 90 E1 03 E0 54 FB 90 E1    .t..........T...
000490: 03 F0 22 90 07 8B 12 1D 45 90 CC 00 E0 54 80 60    .."....E....T.`
0004A0: 08 90 E0 02 E0 04 F0 80 05 90 E0 02 E4 F0 90 CC    ................
0004B0: 00 E0 54 40 60 08 90 E0 00 12 00 0E 80 07 90 E0    ..T@`...........
0004C0: 00 E4 F0 A3 F0 90 E0 00 E0 FE A3 E0 FF EF D3 94    ................
0004D0: B6 EE 94 03 40 2C 90 E0 00 E4 F0 A3 F0 75 A8 00    ....@,.......u..
0004E0: 75 88 00 90 E1 02 E0 44 01 90 E1 02 F0 75 18 01    u......D.....u..
0004F0: 12 00 90 74 82 F5 46 12 15 1C 75 A8 00 75 88 00    ...t..F...u..u..
```

```
000500: D3 22 90 E0 02 E0 D3 94 64 40 2A 90 E0 02 E4 F0      ."......d@*.....
000510: 75 A8 00 75 88 00 90 E1 02 E0 44 01 90 E1 02 F0      u..u......D.....
000520: 75 18 04 12 00 80 74 C8 F5 46 12 15 1C 75 A8 00      u.....t..F...u..
000530: 75 88 00 D3 22 C3 22 12 18 CE 30 00 01 22 E5 35      u..."."...0.."S
000540: C3 94 32 50 01 22 75 35 00 E5 43 44 01 F5 43 E5      ..2P."u5..CD..C.
000550: 2C 75 F0 04 84 FF 7E 00 9F 18 E5 43 90 C4 04 F0      ,u.........C....
000560: 74 20 74 C0 03 F0 74 30 90 C0 02 F0 74 20 90 C0      t t...t0....t...
000570: 04 F0 EF 75 F0 0A 84 AD F0 7C 00 ED 24 30 90 C0      ...u.....|..$0..
000580: 01 F0 E5 18 75 F0 0A 84 FF 7E 00 8F 18 E5 18 70      ....u..........p
000590: 08 74 20 90 C0 00 F0 80 08 E5 18 24 30 90 C0 00      .t ........$0...
0005A0: F0 20 94 05 75 18 00 80 14 E5 2C 24 0F C3 95 2D      . ..u....,$...-
0005B0: 40 05 85 2D 18 80 06 E5 2C 24 0F F5 18 E5 18 C3      @..-....,$......
0005C0: 94 0F 50 05 75 18 00 80 07 E5 18 C3 94 0F F5 18      ..P.u...........
0005D0: E5 18 04 75 F0 02 84 FF 7E 00 8F 18 EF 54 01 70      ...u.........T.p
0005E0: 08 74 30 90 C0 07 F0 80 08 74 35 90 C0 07 F0 15      .t0......t5.....
0005F0: 18 E5 18 75 F0 02 84 FF 7E 00 8F 18 EF 75 F0 0A      ...u.........u..
000600: 84 AD F0 7C 00 ED 24 30 90 C0 06 F0 E5 18 75 F0      ...|..$0......u.
000610: 0A 84 FF 7E 00 8F 18 E5 18 70 08 74 20 90 C0 05      .........p.t ...
000620: F0 80 09 E5 18 24 30 90 C0 05 F0 22 75 1D 01 E5      .....$0...."u...
000630: 1D D3 94 AA 50 49 74 01 F5 18 12 00 DC 90 E8 00      ....PIt.........
000640: E4 F0 12 02 11 90 E8 00 E0 C3 94 02 50 1E 74 0A      ............P.t.
000650: F5 18 12 00 DC 90 E8 00 E4 F0 12 02 11 90 E8 00      ................
000660: E0 C3 94 02 50 06 75 1A 02 12 01 6B 90 E8 00 E0      ....P.u....k....
000670: C3 94 19 50 02 80 05 78 1D 74 01 26 F6 50 B0 75      ...P...x.t.&.P.u
000680: 1A 03 12 01 6B 74 0A F5 18 12 00 DC 22 75 1B 00      ....kt......"u..
000690: 90 CC 00 E0 54 0F 64 0F 60 05 75 1B 00 80 02 05      ....T.d.`.u.....
0006A0: 1B 90 CC 00 E0 F4 54 0F B4 FF 05 E5 22 B4 05 02      ......T....."...
0006B0: 80 03 12 03 04 74 01 F5 18 12 00 DC E5 1B C3 94      .....t..........
0006C0: 12 50 02 80 CB C2 C2 0A C2 B1 A2 B0 50 02 80 13      .P..........P...
0006D0: A2 B0 50 02 80 0D A2 B0 50 02 80 07 75 18 FF 12      ..P.....P...u...
0006E0: 00 80 22 12 03 04 30 0A 02 80 DD D2 0A 75 18 00      .."...0......u..
0006F0: 12 00 80 80 D3 E5 38 C3 94 FA 50 02 05 38 90 E1      ......8...P..8..
000700: 01 E0 54 01 70 0F 90 E1 01 E0 54 01 70 07 E5 38      ..T.p.....T.p..8
000710: D3 94 F5 50 02 80 02 D2 09 90 E1 01 E0 54 01 60      ...P.........T.`
000720: 11 30 94 0E 30 09 08 90 E1 01 E0 54 01 60 03 20      .0..0......T.`. 
000730: 94 02 80 05 C2 09 75 38 00 E5 38 C3 94 3F 50 0C      ......u8..8..?P.
000740: 90 E1 02 E0 54 FE 90 E1 02 F0 80 0A 90 E1 02 E0      ....T...........
000750: 44 01 90 E1 02 F0 22 85 1C 18 12 01 10 12 06 BD      D.....".........
000760: 75 1D 01 E5 1D D3 94 10 50 12 74 0A F5 18 12 00      u.......P.t.....
000770: DC 12 03 04 78 1D 74 01 26 F6 50 E7 22 12 1C 46      ....x.t.&.P."..F
000780: 12 1B 13 12 13 99 75 22 03 80 00 75 A8 00 12 13      ......u"...u....
000790: 18 90 E1 03 E0 54 04 FF 7E 00 EF 60 02 C2 01 E5      .....T.....`....
0007A0: 22 C3 94 04 50 51 E5 22 90 1A 60 93 F5 43 E5 43      "...PQ."..`..C.C
0007B0: 90 C4 04 F0 75 42 3F E5 22 70 03 75 42 BF E5 22      ....uB?."p.uB.."
0007C0: B4 01 03 75 42 7F E5 22 64 04 60 05 E5 22 B4 05      ...uB.."d.`.."..
0007D0: 03 75 42 BF E5 42 90 C4 03 F0 E5 22 90 0C 8A F8      .uB..B....."....
0007E0: 28 28 73 02 08 6C 02 09 41 02 0A 2C 02 08 31 02      ((s..l..A..,..1.
0007F0: 0C 47 02 0C 47 80 03 02 0C 47 75 A9 00 75 88 00      .G..G....Gu..u..
000800: E5 25 70 0D 30 93 05 75 22 00 80 03 75 22 01 80      .%p.0..u"...u".
000810: 3C E5 25 B4 FF 0F E5 22 64 04 60 04 D2 07 80 02      <.%...."d.`.....
000820: B2 07 75 22 04 E5 25 B4 08 03 75 22 03 E5 25 B4      ..u"..%...u"..%.
000830: FF 03 75 22 05 E5 25 B4 04 09 30 93 05 75 22 00      ..u"..%...0..u".
000840: 80 03 75 22 01 E5 25 B4 02 03 75 22 02 E5 22 C3      ..u"..%...u".."
000850: 94 04 50 15 90 C4 05 E4 F0 90 E1 01 E0 54 02 70      ..P..........T.p
000860: 08 90 C4 05 E4 F0 12 01 DB 02 07 BB 75 A8 00 75      ............u..u
000870: 89 00 E5 25 60 06 75 1C 00 12 07 57 12 02 3C 75      ...%`.u....W..<u
000880: 2A 3E 75 28 00 75 23 00 75 98 10 90 F0 03 E4 F0      *>u(.u#.u.......
000890: 90 E1 03 E0 44 08 90 E1 03 F0 12 03 04 12 04 35      ....D..........5
0008A0: 12 18 CE AE 2A AF 28 7C 27 7D 00 12 00 03 7F 01      ....*.(|'}......
0008B0: 7A DC 5E 9F 06 8A 07 12 1D 0A 8E 31 12 02 4C 90      z.^........1..L.
0008C0: E8 03 E4 F0 12 02 11 90 E8 00 E0 F4 75 F0 96 A4      ............u...
0008D0: FF AE F0 EE F4 04 24 C7 F5 45 75 44 90 20 94 08      ......$..EuD. ..
0008E0: 75 23 01 75 27 00 75 26 00 80 3E AE 44 AF 45 74      u#.u'.u&..>.D.Et
0008F0: 80 12 1D 0A 7C 72 7D 00 8E 07 12 1C DE 74 01 8C      ....|r}......t..
000900: 06 8D 07 12 1C FC 8E 26 8F 27 AE 44 AF 45 74 7F      .......&.'.D.Et.
000910: 12 1D 0A 7C 72 7D 00 8E 07 12 1C DE 74 01 8C 06      ...|r}......t...
000920: 8D 07 12 1C FC 8E 28 8F 29 90 E0 07 E0 C3 94 20      ......(.)...... 
000930: 50 09 90 E0 07 E0 F5 1A 12 01 6B 12 01 DB 02 08      P.........k.....
000940: BB 75 A8 00 75 88 00 E5 25 60 06 75 1C 00 12 07      .u..u...%`.u....
000950: 57 12 02 3C 75 23 03 90 E0 10 E4 F0 A3 F0 75 88      W..<u#........u.
000960: 10 90 F0 03 E4 F0 90 E1 03 E0 44 08 90 E1 03 F0      ..........D.....
```

```
000970: 12 03 04 12 04 35 12 18 CE 90 E8 03 E4 F0 12 02
000980: 11 90 EB 00 E0 F4 F5 39 85 39 31 12 02 4C 30 94
000990: 41 90 E0 10 E4 F0 A3 F0 E5 39 75 F0 89 A4 FF AE
0009A0: F0 74 FF 8E 04 8F 05 FF 12 1C DE 74 27 2D FD 50
0009B0: 01 0C 8C 44 8D 45 ED D3 94 B0 EC 94 00 40 06 75
0009C0: 44 00 75 45 80 90 F0 01 E4 F0 E5 45 90 F0 02 F0
0009D0: 80 42 E5 39 D3 94 1E 40 08 90 E0 10 12 00 0E 80
0009E0: 12 90 E0 10 E0 FE A3 E0 FF EF 4E 60 06 90 E0 10
0009F0: 12 1C EE 90 E0 10 E0 FE A3 E0 FF EF D3 94 D0 EE
000A00: 94 07 40 06 75 1A 10 12 01 6B 90 F0 02 E4 F0 90
000A10: F0 01 E4 F0 90 E0 07 E0 C3 94 80 50 09 90 E0 07
000A20: E0 F5 1A 12 01 6B 12 01 DB 02 09 61 7A 75 A8 00
000A30: 88 00 E5 25 B4 02 06 75 1C 01 12 07 57 12 06 C6
000A40: 12 03 B2 75 A8 00 75 88 00 90 E1 03 E0 54 DF 90
000A50: E1 03 F0 90 E8 04 E4 F0 12 02 11 90 E8 00 E0 75
000A60: F0 F1 A4 FF AE F0 8E 2C E5 43 44 01 F5 43 E5 43
000A70: 90 C4 04 F0 75 3B 01 12 06 2C 75 35 2D 12 02 3C
000A80: 75 23 02 75 88 10 90 E0 00 E4 F0 A3 F0 90 E0 02
000A90: E4 F0 12 04 99 50 02 80 DB 30 94 1E 90 E1 03 E0
000AA0: 44 10 90 E1 03 F0 AE 40 AF 41 74 E8 D3 9F 74 FD
000AB0: 9E 40 05 78 40 12 1D 3D 80 30 AE 40 AF 41 74 2C
000AC0: D3 9F 74 01 9E 40 08 75 41 00 75 40 00 80 18 75
000AD0: 41 00 75 40 00 75 A8 00 75 88 00 90 E1 02 E0 44
000AE0: 01 90 E1 02 F0 12 17 CC 80 8A 30 94 08 90 E1 01
000AF0: E0 54 01 70 02 80 0C 90 E1 02 E0 54 FE 90 E1 02
000B00: F0 80 0A 90 E1 02 E0 44 01 90 E1 02 F0 12 03 04
000B10: 12 04 35 12 02 89 12 05 37 90 E0 07 E0 C3 94 80
000B20: 50 09 90 E0 07 E0 F5 1A 12 01 6B 12 01 DB 02 0A
000B30: 92 75 A8 00 75 88 00 E5 25 B4 08 06 75 1C 0E 12
000B40: 07 57 12 03 B2 75 A8 00 75 88 00 90 E1 03 E0 54
000B50: DF 90 E1 03 F0 90 E8 04 E4 F0 12 02 11 90 E8 00
000B60: E0 75 F0 F1 A4 FF AE F0 8E 2C 75 1D 00 E5 43 44
000B70: 01 F5 43 E5 43 90 C4 04 F0 75 3B 01 12 06 2C 75
000B80: 35 2D 75 89 11 75 8A 02 75 8C 80 75 88 08 75 8B
000B90: 02 75 8D D0 75 24 01 75 30 FF 75 23 02 75 A8 8A
000BA0: 75 88 50 75 2F 02 75 2E 00 90 E0 00 E4 F0 A3 F0
000BB0: 90 E0 02 E4 F0 30 94 1E 90 E1 03 E0 44 10 90 E1
000BC0: 03 F0 AE 40 AF 41 74 E8 D3 9F 74 FD 9E 40 05 78
000BD0: 40 12 1D 3D 80 42 75 30 FF AE 40 AF 41 74 2C D3
000BE0: 9F 74 01 9E 40 12 75 41 00 75 40 00 90 E1 03 E0
000BF0: 54 EF 90 E1 03 F0 90 20 75 41 00 75 40 00 75 A8
000C00: 00 75 88 00 D2 96 90 F0 01 E4 F0 90 F0 03 E4 F0
000C10: D2 97 12 17 CC 02 0B 79 12 03 04 12 04 99 50 03
000C20: 02 0B 79 12 04 35 12 02 89 12 05 37 12 02 4C 90
000C30: E0 07 E0 C3 94 80 50 09 90 E0 07 E0 F5 1A 12 01
000C40: 6B 12 01 DB 02 0B 85 74 FF 90 E1 03 F0 90 F0 03
000C50: E4 F0 90 F0 02 E4 F0 75 43 80 D2 97 D2 96 90 E1
000C60: 02 E0 44 01 90 E1 02 F0 75 18 07 12 01 10 74 41
000C70: 90 C0 06 F0 C2 90 80 FE 02 03 69 02 03 73 02 03
000C80: 7D 02 03 87 02 03 91 02 03 93 02 07 E3 02 07 E6
000C90: 02 07 E9 02 07 EC 02 07 EF 02 07 F2 75 4C 1E 75
000CA0: 4B 00 75 4B 02 75 4C 58 75 4C 44 75 4B 00 75 4C
000CB0: 37 75 4B 00 30 92 06 E5 22 64 02 60 02 80 26 90
000CC0: E8 00 E4 F0 75 4C 28 75 4B 00 75 4B 03 75 4C 21
000CD0: 75 4C 29 75 4B 00 75 4B 01 75 4C 93 30 92 06 74
000CE0: 0B 90 E0 07 F0 75 4C 01 75 4B 00 AE 4B AF 4C 74
000CF0: 28 BE 00 15 9F 40 12 30 92 01 22 78 4C 74 01 26
000D00: F6 50 04 18 E4 36 F6 50 E2 74 08 90 E0 07 F0 22
000D10: 75 8C DB 75 8A FF 05 35 05 36 05 34 E5 3B B5 52
000D20: 05 A2 03 B3 40 02 80 0C E5 43 44 80 F5 43 E5 43
000D30: 90 C4 04 F0 E5 3B 60 02 15 3B E5 3B 70 07 E5 22
000D40: D3 94 01 50 02 80 3D A2 94 23 40 07 E5 2D C3 94
000D50: 14 50 05 75 52 00 80 2C 74 AF C3 93 2D 75 F0 8C
000D60: A4 FF AE F0 EE 24 0F F5 52 F5 3B E5 2D D3 94 AF
000D70: 40 06 74 0C F5 52 F5 3B E5 43 54 7F F5 43 E5 43
000D80: 90 C4 04 F0 E5 3B C3 94 FA 50 02 05 3B E5 23 D3
000D90: 94 04 40 03 02 0F D3 E5 23 90 12 F4 F8 28 28 73
000DA0: 80 0B 80 3F 02 0E 51 02 0F BB 02 0E 7B AE 26 AF
000DB0: 27 EF D3 94 08 EE 94 07 40 03 02 0F D3 AE 2A AF
000DC0: 2B AC 26 AD 27 EF 2D FD EE 3C FC 8C 2A 8D 2B ED
000DD0: D3 94 00 EC 94 B2 40 09 75 2A 50 75 2B 00 75 23
```

```
000DE0: 01 80 33 AE 28 AF 29 EF D3 94 08 EE 94 07 40 03    ..3.(.).......@.
000DF0: 02 0F D3 AE 2A AF 2B AC 2B AD 29 12 00 03 8E 2A    ....*.+.+.)....*
000E00: 8F 2B 74 00 D3 9F 74 3E 9E 40 09 75 2A 3E 75 2B    .+t...t>.@.u*>u+
000E10: 00 75 23 00 80 00 E5 22 60 03 02 0F D3 90 F0 03    .u#...."`.......
000E20: E4 F0 90 E1 03 E0 44 C8 90 E1 03 F0 30 94 11 E5    ......D.....0...
000E30: 2B C4 54 0F 90 F0 01 F0 E5 2A 90 F0 02 F0 80 10    +.T......*......
000E40: 75 2A 27 75 2B 00 90 F0 01 E4 F0 90 F0 02 E4 F0    u*'u+...........
000E50: 22 E5 22 64 02 60 05 E5 22 B4 03 02 80 03 02 0F    "."d.`..".......
000E60: D3 90 E8 04 E4 F0 12 0C 9C 90 E8 00 E0 75 F0 A1    .............u..
000E70: A4 FF AE F0 EE 54 FC F5 2C 80 3A E5 22 64 04 60    .....T..,.:."d.`
000E80: 05 E5 22 B4 05 02 80 03 02 0F D3 90 E8 04 E4 F0    .."............. 
000E90: 12 0C 9C 90 E8 00 E0 75 F0 05 84 FF 7E 00 EF 24    .......u....~..$
000EA0: 33 F5 3A 90 E8 00 E0 75 F0 DD A4 FF AE F0 EE 54    3.:....u.......T
000EB0: FC F5 2C 80 00 90 E8 03 E4 F0 12 0C 9C 90 E8 00    ..,.............
000EC0: E0 F4 F5 39 90 E8 05 E4 F0 E5 22 64 04 60 05 E5    ...9......"d.`..
000ED0: 22 B4 05 02 80 2F E5 39 D3 94 1B 40 09 E5 39 C3    "..../.9...@..9.
000EE0: 94 1C F5 39 80 03 75 39 00 E5 39 75 F0 12 A4 FF    ...9..u9..9u....
000EF0: AE F0 74 04 12 1C FC EF 85 2C F0 A4 FF AE F0 85    ..t......,......
000F00: 4D 8F 4E 80 2D E5 39 D3 94 39 40 09 E5 39 C3 94    M.N.-.9..9@..9..
000F10: 3A F5 4F 80 03 75 4F 00 E5 4F 75 F0 53 A4 FF AE    :.O..uO..Ou.S...
000F20: F0 74 06 12 1C FC EF 85 2C F0 A4 FF AE F0 8E 4D    .t......,......M
000F30: 8F 4E 12 0C 9C 90 E8 00 E0 F5 4F 90 E8 00 E4 F0    .N........O.....
000F40: 12 0C 9C 90 E8 00 E0 F5 2D E5 22 C3 94 02 40 07    ........-."...@.
000F50: E5 22 D3 94 05 40 02 80 7A 30 94 1B E5 2D D3 94    ."...@..z0...-..
000F60: 01 40 14 E5 4E 45 4D 60 0E E5 22 64 04 60 05 E5    .@..NEM`.."d.`..
000F70: 22 B4 05 05 30 07 02 80 13 E5 4E C4 54 0F 90 F0    "...0.....N.T...
000F80: 01 F0 E5 4D 24 0F 90 F0 03 F0 80 0A 90 F0 01 E4    ...M$...........
000F90: F0 90 F0 03 E4 F0 90 E8 05 E4 F0 12 0C 9C 90 E8    ................
000FA0: 00 E0 C3 95 4F C3 94 03 40 0D 90 E8 00 E0 F4 04    ....O...@.......
000FB0: 25 4F C3 94 03 50 03 85 4F 31 22 E5 22 64 01 60    %O...P..O1"."d.`
000FC0: 02 80 10 90 F0 03 E4 F0 90 E1 03 E0 44 C8 90 E1    ............D...
000FD0: 03 F0 22 90 0C 47 12 1D 45 75 51 00 E5 51 D3 94    ..".G..EuQ..Q..
000FE0: 07 50 1B E5 50 90 19 58 93 FE E5 51 90 C0 00 12    .P..P..X...Q....
000FF0: 1D 2B EE F0 05 50 78 51 74 01 26 F6 50 DE 22 E5    .+...PxQt.&.P.".
001000: 24 90 13 03 F8 28 28 73 80 11 02 10 CB 02 12 3F    $....((s.......?
001010: 02 12 81 02 12 DA 80 6C 02 10 F5 75 8B 02 75 8D    .......l...u..u.
001020: CA E5 31 D3 94 F5 40 05 75 8D CF 80 12 E5 31 D3    ..1...@.u.....1.
001030: 94 E5 40 05 75 8D CE 80 16 E5 31 D3 94 D0 40 05    ..@.u.....1...@.
001040: 75 8D CC 80 0A E5 31 D3 94 B4 40 03 75 8D CB E5    u.....1...@.u...
001050: 22 64 03 60 03 02 12 EE C2 96 75 24 01 7E A6 7F    "d.`......u$.~..
001060: 38 E5 31 75 F0 02 84 FD 7C 00 ED 24 0C 8E 14 8F    8.1u....|..$....
001070: 15 FF 12 1C DE 74 FF 62 14 62 15 8C 2E 8D 2F E5    .....t.b.b..../.
001080: 2E F5 30 22 75 8B 02 75 8D 70 E5 22 64 04 60 05    ..0"u..u.p."d.`.
001090: E5 22 B4 05 02 80 03 02 12 EE D2 06 A2 94 83 92    ."..............
0010A0: 97 75 24 06 7E C2 7F 10 E5 31 75 F0 08 84 FD 7C    .u$.~....1u....|
0010B0: 00 ED 24 0F 8E 14 8F 15 FF 12 1C DE 74 FF 62 14    ..$.........t.b.
0010C0: 62 15 8C 2E 8D 2F E5 2E F5 30 22 D2 96 E5 22 64    b..../...0"..."d
0010D0: 03 60 03 02 12 EE A2 93 82 94 40 01 22 05 30 E5    .`........@.".0.
0010E0: 30 60 07 75 8B 02 75 8D 00 22 75 24 00 75 8B 02    0`.u..u.."u$.u..
0010F0: E5 2F F5 8D 22 E5 22 64 04 60 05 E5 22 B4 05 02    ./.."."d.`.."...
001100: 80 03 02 12 EE 30 07 03 D2 97 22 75 8D DB 75 8B    .....0...."u..u.
001110: FF E5 2D C3 94 2F 50 02 C2 0C E5 3E C3 94 03 50    ..-../P....>...P
001120: 07 E5 39 C3 94 28 50 02 80 16 C2 0C 90 E1 03 E0    ..9..(P.........
001130: 44 C1 90 E1 03 F0 75 3C 04 75 3E 03 C2 97 D2 08    D.....u<.u>.....
001140: E5 39 C3 94 37 40 17 20 0C 02 C2 97 90 E1 03 E0    .9..7@. ........
001150: 44 C1 90 E1 03 F0 75 3D 28 75 3E 04 D2 06 E5 3E    D.....u=(u>....>
001160: 84 04 07 E5 2D D3 94 3F 50 02 80 D2 D2 0C E5 39    ....-..?P......9
001170: D3 94 1E 50 07 E5 3E C3 94 04 40 02 80 0B D2 97    ...P..>...@.....
001180: 75 3E 01 E5 3C 60 02 15 3C E5 3E B4 01 06 E5 2D    u>..<`..<.>....-
001190: 64 04 60 02 80 1E E5 3C 70 0E 90 E1 01 E0 F5 90    d.`....<p.......
0011A0: E1 01 E0 5E 54 01 70 02 80 0A 90 E1 03 E0 54 3E    ...^T.p.......T>
0011B0: 90 E1 03 F0 E5 3E B4 04 07 E5 39 D3 94 1E 40 02    .....>....9...@.
0011C0: 80 1C E5 2D C3 94 13 50 07 D2 97 75 3E 03 E0 0E    ...-...P...u>...
0011D0: C2 97 15 3D E5 3D 70 06 74 07 90 E0 07 F0 30 94    ...=.=p.t.....0.
0011E0: 08 E5 3E B4 04 03 20 0C 07 75 8B 02 75 8D 2C 22    ..>... ..u..u.,"
0011F0: E5 30 04 75 F0 33 84 AF F0 33 84 AF F0 7E 00 8F    .0.u.3...3...~..
001200: 30 E5 31 75 F0 B1 A4 FD AC F0 EC 75 F0 04 84 FD    0.1u.......u....
001210: 7C 00 ED 24 02 F5 3F E5 3F D3 94 2D 50 07 E5 31    |..$..?.?..-P..1
001220: D3 94 FA 40 03 75 3F 33 E5 30 70 06 C2 97 D2 08    ...@.u?3.0p.....
001230: 80 10 30 08 07 E5 30 C3 95 3F 50 02 80 04 C2 09    ..0...0..?P.....
001240: D2 97 22 15 33 E5 33 70 3B E5 32 C3 94 05 50 04    ..".3.3p;.2...P.
                                                          E5 32 70 0E
                                                          .2p.
```

```
001250: 30 03 06 E5 32 64 05 60 05 E5 32 B4 07 0E C2 03     0...2d.`..2.....
001260: E5 43 54 7F F5 43 E5 43 90 C4 04 F0 E5 32 75 F0     .CT..C.C.....2u.
001270: 10 A4 FF AE F0 8F 50 12 0F D9 75 33 0A 75 24 03     ......P...u3.u$.
001280: 22 15 33 E5 32 B4 01 2A E5 33 C3 94 06 50 07 E5     ".3.2.*.3...P..
001290: 33 D3 94 04 50 02 80 0E E5 43 44 80 F5 43 E5 43     3...P....CD..C.C
0012A0: 90 C4 04 F0 80 0C E5 43 54 7F F5 43 E5 43 90 C4     .......CT..C.C..
0012B0: 04 F0 E5 33 70 23 E5 43 44 80 F5 43 E5 43 90 C4     ...3p#.CD..C.C..
0012C0: 04 F0 E5 32 75 F0 10 A4 FF AE F0 EF 24 08 F5 50     ...2u.......$..P
0012D0: 12 0F D9 75 33 0A 75 24 04 22 15 33 E5 33 70 0D     ...u3.u$.".3.3p.
0012E0: 74 80 F5 50 12 0F D9 75 33 04 75 24 02 22 90 0C     t..P...u3.u$.".
0012F0: 47 12 1D 45 02 0D A0 02 0D A2 02 0D A4 02 0D A7     G..E............
001300: 02 0D AA 02 10 08 02 10 0A 02 10 0D 02 10 10 02     ................
001310: 10 13 02 10 16 02 10 18 75 A8 00 75 88 00 75 B8     ........u..u..u.
001320: 00 75 89 00 74 5F 90 E1 02 F0 90 F0 01 E4 F0 90     .u..t_..........
001330: F0 02 E4 F0 90 F0 03 E4 F0 D2 96 90 E1 02 E0 44     ...............D
001340: 01 90 E1 02 F0 74 FF 90 E0 07 F0 75 27 00 75 26     .....t.....u'.u&
001350: 00 75 29 00 75 28 00 75 2B 00 75 2A 00 C2 00 75     .u).u(.u+.u*...u
001360: 34 00 90 E1 03 E0 54 CF 44 0B 90 E1 03 F0 12 1A     4.....T.D.......
001370: 66 90 CC 00 E0 54 10 60 0F 75 18 03 12 00 80 75     f....T.`.u.....u
001380: 18 FA 12 00 DC 75 A8 00 12 01 4D 90 E0 02 E4 F0     .....u....M.....
001390: 75 41 00 75 40 00 C2 04 22 75 43 80 E5 43 90 C4     uA.u@..."uC..C..
0013A0: 04 F0 74 4E 90 E1 00 F0 74 AF 90 E1 02 F0 74 FF     ..tN....t.....t.
0013B0: 90 E1 03 F0 D2 97 D2 96 90 F0 01 E4 F0 90 F0 02     ................
0013C0: E4 F0 90 F0 03 E4 F0 90 E1 03 E0 54 DF 90 E1 03     ...........T....
0013D0: F0 75 37 00 C2 01 C2 02 75 19 28 12 00 DC 75 42     .u7.....u.(...uB
0013E0: 00 12 1A 66 90 E8 00 E4 F0 12 02 11 90 CC 00 E0     ...f............
0013F0: 54 10 60 06 75 18 03 12 00 80 90 CC 00 E0 54 10     T.`.u.........T.
001400: 60 0A 90 CC 00 E0 54 0F 64 0F 60 02 80 02 80 EA     `.....T.d.`.....
001410: 75 18 0A 12 00 DC C2 0B 30 94 09 75 18 07 12 00     u.......0..u....
001420: 80 D2 0B 75 48 00 75 47 01 75 46 00 AE 46 AF 47     ...uH.uG.uF..F.G
001430: 74 20 C3 9F 74 03 9E 40 27 30 94 05 75 48 00 80     t ..t..@'0..uH..
001440: 02 48 75 18 01 12 00 DC E5 48 D3 94 14 40 02       .Hu......H...@.
001450: 80 14 78 47 74 01 26 F6 50 04 18 E4 36 F6 50 CC     ..xGt.&.P...6.P.
001460: 75 1A 11 12 01 6B 75 A8 00 75 B8 00 E5 43 44 80     u....ku.u...CD.
001470: F5 43 E5 43 90 C4 04 F0 30 0B 0C 75 18 08 12 01     .C.C....0..u....
001480: 10 75 18 64 12 00 DC 90 E8 00 E0 D3 94 13 50 09     .u.d..........P.
001490: 90 E8 00 E0 C3 94 0B 50 2C 75 19 32 12 00 DC 90     .......P,u.2....
0014A0: E8 00 E4 F0 12 02 11 90 E8 00 E0 F5 2D 90 E8 00     ............-...
0014B0: E0 D3 94 13 50 09 90 E8 00 E0 C3 94 08 50 06 75     ....P........P.u
0014C0: 1A 05 12 01 6B 12 01 4D 22 90 E1 02 E0 44 01 90     ....k..M"....D..
0014D0: E1 02 F0 90 E1 03 E0 54 01 FF 7E 00 EF 70 10 90     .......T..~..p..
0014E0: E1 03 E0 44 01 90 E1 03 F0 75 18 14 12 00 DC 90     ...D.....u......
0014F0: E1 03 E0 44 04 90 E1 03 F0 75 18 15 12 00 DC 90     ...D.....u......
001500: E1 03 E0 54 FE 90 E1 03 F0 75 18 3C 12 00 DC 90     ...T.....u.<....
001510: E1 03 E0 44 01 90 E1 03 F0 C2 01 22 D2 96 90 E1     ...D......."....
001520: 03 E0 54 F7 90 E1 03 F0 D2 97 90 F0 03 E4 F0 90     ..T.............
001530: F0 01 E4 F0 75 18 14 12 00 DC 75 41 00 75 40 00     ....u.....uA.u@.
001540: 90 E1 03 E0 54 FD 90 E1 03 F0 C2 0B 75 4A 01 75     ....T.......uJ.u
001550: 49 00 AE 49 AF 4A E5 46 BE 00 03 9F 50 03 02 16     I..I.J.F....P...
001560: 37 75 48 01 75 47 00 AE 47 AF 48 74 08 C3 9F 74     7uH.uG..G.Ht...t
001570: 07 9E 40 0E 78 48 74 01 26 F6 50 04 18 E4 36 F6     ..@.xHt.&.P...6.
001580: 50 E5 90 E1 01 E0 FE 90 E1 01 E0 5E 54 01 60 02     P..........^T.`.
001590: D2 0B 90 E8 05 E4 F0 12 02 11 90 E8 00 E0 F5 31     ...............1
0015A0: 90 E8 00 E4 F0 12 02 11 90 E8 00 E0 C3 94 02 50     ...............P
0015B0: 27 75 18 14 12 00 DC 90 E8 00 E4 F0 12 02 11 90     'u..............
0015C0: E8 00 E0 C3 94 02 50 10 90 E1 03 E0 54 DF 90 E1     ......P.....T...
0015D0: 03 F0 75 1A 02 12 01 6B E5 36 24 02 F5 36 12 02     ..u....k.6$..6..
0015E0: 4C E5 22 B4 04 03 20 08 02 80 16 AE 49 AF 4A 74     L."... .....I.Jt
0015F0: 07 BE 00 03 9F 50 0A 90 E1 03 E0 54 FE 90 E1 03     .....P.....T....
001600: F0 AE 49 AF 4A 74 25 BE 00 03 9F 50 19 20 94 0C     ..I.Jt%....P. ..
001610: 90 E1 03 E0 54 EF 90 E1 03 F0 80 0A 90 E1 03 E0     ....T...........
001620: 44 10 90 E1 03 F0 78 4A 74 01 26 F6 50 04 18 E4     D.....xJt.&.P...
001630: 36 F6 40 03 02 15 52 90 E1 03 E0 44 02 44 08 90     6.@...R....D.D..
001640: E1 03 F0 75 18 FF 12 00 80 90 CC 00 E0 54 40 60     ...u.........T@`
001650: 08 75 18 02 12 00 80 12 03 04 80 FB 22 90 E1 03     .u.........."...
001660: E0 44 10 90 E1 03 F0 75 18 09 12 01 10 D2 02 75     .D.....u.......u
001670: 18 64 12 00 DC 75 46 01 E5 46 D3 94 3C 50 19 75     .d...uF..F..<P.u
001680: 18 0A 12 00 DC 12 03 04 A2 94 82 94 50 02 80 08     ............P...
001690: 78 46 74 01 26 F6 50 E0 90 E1 03 E0 54 EF 90 E1     xFt.&.P.....T...
0016A0: 03 F0 12 01 4D 22 D2 0B 75 18 05 12 01 10 75 18     ....M"..u.....u.
0016B0: 0A 12 00 DC D2 97 75 18 0C 12 00 DC 90 E1 03 E0     ......u.........
```

```
0016C0: 44 20 54 FD 90 E1 03 F0 75 18 0C 12 00 DC 90 E1     D T.....u.......
0016D0: 03 E0 54 F7 90 E1 03 F0 75 47 00 75 46 00 E5 47     ..T.....uG.uF..G
0016E0: C3 94 C8 50 07 E5 46 C3 94 48 40 02 80 2F 05 47     ...P..F..H@../.G
0016F0: 90 E8 00 E4 F0 75 18 01 12 00 DC 12 02 11 90 E8     .....u..........
001700: 00 E0 F5 46 E5 46 C3 94 02 50 10 90 E1 03 E0 54     ...F.F...P.....T
001710: DF 90 E1 03 F0 75 1A 02 12 01 6B 80 C1 90 E1 03     .....u....k.....
001720: E0 44 02 90 E1 03 F0 75 18 0C 12 00 DC 90 E1 03     .D.....u........
001730: E0 44 08 90 E1 03 F0 90 CC 00 E0 54 20 60 06 12     .D.........T `..
001740: 14 C9 02 17 C6 75 18 64 12 00 DC 90 E8 00 E4 F0     .....u.d........
001750: 12 02 11 E5 46 C3 94 02 40 09 90 E8 00 E0 C3 94     ....F...@.......
001760: 02 50 10 90 E1 03 E0 54 DF 90 E1 03 F0 75 1A 02     .P.....T.....u..
001770: 12 01 6B E5 46 C3 94 48 40 0E 90 E8 00 E0 FE E5     ..k.F..H@.......
001780: 46 C3 94 19 C3 9E 40 02 80 12 75 18 02 12 01 10     F.....@...u.....
001790: 75 18 32 12 00 DC D2 01 12 01 4D 22 30 08 05 C2     u.2.......M"0...
0017A0: 08 02 16 BC 75 18 05 12 00 80 90 CC 00 E0 54 20     ....u.........T 
0017B0: 60 08 90 CC 00 E0 54 20 70 02 80 05 12 14 C9 80     `.....T p.......
0017C0: 05 12 03 04 80 E4 90 07 88 12 1D 45 90 E0 10 E4     ...........E....
0017D0: F0 A3 F0 D2 96 D2 97 90 F0 03 E4 F0 90 F0 01 E4     ................
0017E0: F0 C2 0B 90 E1 03 E0 54 F7 90 E1 03 F0 75 2D 0F     .......T.....u-.
0017F0: A2 05 40 06 E5 43 44 80 F5 43 E5 43 90 C4 04 F0     ..@..CD..C.C....
001800: C2 04 75 18 0A 12 00 DC 90 E1 03 E0 54 FD 90 E1     ..u........T....
001810: 03 F0 75 47 01 75 46 00 AE 46 AF 47 74 2C C3 9F     ..uG.uF..F.Gt,..
001820: 74 01 9E 50 03 02 18 C1 74 01 52 07 7E 00 EF 4E     t..P....t.R.~..N
001830: 70 06 75 18 01 12 00 DC 90 E1 01 E0 FE 90 E1 01     p.u.............
001840: E0 5E 54 01 60 02 D2 0B 30 94 02 80 74 90 E8 03     .^T.`...0...t...
001850: E4 F0 12 02 11 90 E8 00 E0 C3 94 E1 50 06 90 E0     ............P...
001860: 10 12 00 0E 90 E0 10 E0 FE A3 E0 FF 74 78 8E 00     ............tx..
001870: 03 9F 50 06 75 1A 10 12 01 68 AE 46 AF 47 74 19     ..P.u....h.F.Gt.
001880: 8E 00 03 9F 50 03 20 02 80 0F E5 22 B4 04 0A     ....P. ...."...
001890: 90 E1 03 E0 54 FE 90 E1 03 F0 AE 46 AF 47 74 7D     ....T......F.Gt}
0018A0: 8E 00 03 9F 50 0A 90 E1 03 E0 54 EF 90 E1 03 F0     ....P.....T.....
0018B0: 78 47 74 01 26 F6 50 04 18 E4 36 F6 40 03 02 18     xGt.&.P...6.@...
0018C0: 18 90 E1 03 E0 44 02 44 08 90 E1 03 F0 22 90 CC     .....D.D....."..
0018D0: 00 E0 54 10 70 33 C2 05 75 37 00 20 94 06 E5 43     ..T.p3..u7. ...C
0018E0: 44 80 F5 43 E5 43 90 C4 04 F0 C2 00 75 34 D7 E5     D..C.C......u4..
0018F0: 22 C3 94 02 50 11 E5 35 C3 94 32 50 01 22 75 35     "...P..5..2P."u5
001900: 00 75 18 00 12 01 10 80 4E E5 34 D3 94 DC 40 47     .u......N.4...@G
001910: 75 34 00 B2 00 30 00 21 E5 37 C3 94 05 50 10 E5     u4...0.!.7...P..
001920: 43 54 7F F5 43 E5 43 90 C4 04 F0 D2 05 05 37 75     CT..C.C.......7u
001930: 34 8C 75 18 04 12 01 10 22 E5 43 44 80 F5 43 E5     4.u....."CD..C.C
001940: 43 90 C4 04 F0 C2 05 75 35 FA E5 22 C3 94 02 50     C......u5.."...P
001950: 06 75 18 00 12 01 10 22 20 43 48 45 43 48 20 20     .u....." CHECK  
001960: 20 43 41 42 4C 45 20 20 54 52 41 4E 53 46 45 52      CABLE   TRANSFER
001970: 54 52 41 4E 53 46 45 52 20 43 48 45 43 48 20 20     TRANSFER CHECK  
001980: 43 41 53 53 45 54 54 45 4C 4F 57 20 41 49 52 20     CASSETTELOW AIR 
001990: 50 52 45 53 53 55 52 45 20 43 48 45 43 48 20 20     PRESSURE CHECK  
0019A0: 43 4F 4E 54 41 43 54 53 20 56 41 43 55 55 4D 20     CONTACTS VACUUM 
0019B0: 20 20 4C 45 41 48 20 20 20 49 4E 53 45 52 54 20       LEAK   INSERT 
0019C0: 43 41 53 53 45 54 54 45 52 45 4C 45 41 53 45 20     CASSETTERELEASE 
0019D0: 20 46 4F 4F 54 53 57 20 20 20 20 20 20 20 20 20      FOOTSW         
0019E0: 53 43 49 53 53 4F 52 53 20 20 46 52 41 47 20 20     SCISSORS  FRAG  
0019F0: 20 20 20 4F 48 20 20 20 54 52 41 4E 53 46 45 52        OK   TRANSFER
001A00: 4C 4F 57 20 20 41 49 52 43 48 45 43 48 49 4E 47     LOW  AIRCHECKING
001A10: 20 45 52 52 4F 52 20 20 45 52 52 4F 52 20 20 20      ERROR  ERROR   
001A20: 4D 56 53 20 56 31 2E 31 49 52 52 20 4F 50 45 4E     MVS V1.1IRR OPEN
001A30: 49 2F 41 20 46 52 41 47 20 4D 55 4C 54 49 20 20     I/A FRAG MULTI  
001A40: 20 20 50 52 4F 50 20 20 20 49 2F 41 20 20 20 20       PROP   I/A    
001A50: 20 20 56 49 54 20 20 20 49 52 52 20 4F 4E 4C 59       VIT   IRR ONLY
001A60: 88 88 84 80 80 80 74 FF 90 C4 00 F0 74 FF 90 C4     ......t.....t...
001A70: 01 F0 74 FF 90 C4 02 F0 E5 42 44 3F 90 C4 03 F0     ..t......BD?....
001A80: 22 E5 1E D3 94 1E 50 07 E5 1E C3 94 01 50 07 74     ".....P......P.t
001A90: AA 90 C4 00 F0 22 75 1F 00 E5 1E D3 94 08 40 16     ....."u.......@.
001AA0: E5 1F 90 C4 00 12 1D 2B 74 00 F0 05 1F E5 1E C3     .......+t.......
001AB0: 94 08 F5 1E 80 E3 E5 1F C3 94 03 50 13 E5 1E 90     ...........P....
001AC0: 1D 22 93 FE E5 1F 90 C4 00 12 1D 2B EE F0 80 19     ."........+....
001AD0: E5 1E 90 1D 22 93 54 3F FE E5 42 54 C0 4E FE E5     ...."..T?..BT.N..
001AE0: 1F 90 C4 00 12 1D 2B EE F0 05 1F E5 1F C3 94 04     ......+.........
001AF0: 50 20 E5 1F B4 03 0C E5 42 54 C0 4F 90 C4 04     P ......BT.O...
001B00: F0 80 08 E5 1F 90 C4 00 12 1D 2B 74 FF F0 05 1F     ..........+t....
001B10: 80 D9 22 90 E8 00 E4 F0 75 1F 14 75 1E 00 75 1E     .."....u..u..u.
001B20: 1F 75 1F 55 75 1F 14 75 1E 00 75 1E 1F 75 1F 55     .u.Uu..u..u..u.U
```

```
001B30: 30 92 06 75 1A 0B 12 01 68 75 1F 01 75 1E 00 AE     0..u....ku..u...
001B40: 1E AF 1F 74 28 BE 00 16 9F 40 13 30 92 02 80 14     ...t(....a.0....
001B50: 78 1F 74 01 26 F6 50 04 18 E4 36 F6 50 E1 75 1A     x.t.&.P...6.P.u.
001B60: 0B 12 01 6B 22 BC 00 0F BE 00 0B ED EF F0 84 FF     ...k"...........
001B70: AD F0 22 E4 FE FF 22 BE 00 0D EF 60 FE 54 F0 60     .."...."...`.T.`
001B80: 6F 20 E7 03 02 1C 1B EA C0 E0 EB C0 E0 78 01 7A     o............x.z
001B90: 00 75 F0 01 EE 20 E7 10 EF 25 E0 FF EE 33 FE 0A     .u.......%...3..
001BA0: C5 F0 23 C5 F0 30 E7 F0 EA 54 07 F9 F0 09 6A 7A 00  ..#..0...T....jz.
001BB0: 7B 00 60 01 08 C3 EC 9E 40 16 70 04 ED 9F 40 10     {.`.....@.p...@.
001BC0: ED 9F FD EC 9E FC E5 F0 CA 4A CA 03 F5 F0 80 05     .........J......
001BD0: E5 F0 03 F5 F0 C3 EE 13 FE EF 13 FF D9 D7 79 08     ..............y.
001BE0: CA CB CA D8 D0 EA FE EB FF D0 E0 F9 D0 E0 FA 22     ..............."
001BF0: EC 8F F0 84 FC ED 54 F0 45 F0 C4 8F F0 84 FE ED     ......T.E.......
001C00: C4 54 F0 45 F0 C4 8F F0 84 FD EE C4 FE 54 F0 2D     .T.E.........T.-
001C10: FF EE 54 0F 3C FE AD F0 7C 00 22 79 00 79 00 8F     ..T.<...|."y.y..
001C20: F0 EC 7E 08 20 E7 0D C3 CD 33 CD 33 C9 33 C9 C8     ..~. ....3.3.3..
001C30: 33 C8 DE F0 84 49 F9 E5 F0 8F F0 BE 00 E6 FD 7C     3....I.........|
001C40: 00 E9 FF E8 FE 22 90 00 00 78 00 79 00 E4 93 28     ....."...x.y...(
001C50: F8 E9 34 00 F9 A3 74 1F B5 83 F2 74 FE B5 82 ED     ..4...t....t....
001C60: E4 93 69 70 18 74 01 93 68 70 15 75 A0 E0 78 00     ..ip.t..hp.u..x.
001C70: E8 F4 F2 08 70 FA B2 28 B4 FF 0E 08 B8 00 F7 22     ....p..(......."
001C80: C2 B1 F2 1C 9B C2 5A 80 FE 12 1C 98 A3 B4 94 E5     ......Z.........
001C90: 83 84 FF F8 75 83 00 B2 B1 80 F1 75 18 07 12 01     ....u......u....
001CA0: 10 90 C0 06 74 42 F0 22 C0 E0 C0 F0 C0 83 C0 82     ....tB."........
001CB0: C0 D0 75 D0 08 12 0D 10 D0 D0 D0 82 D0 83 D0 F0     ..u.............
001CC0: D0 E0 32 C0 E0 C0 F0 C0 83 C0 82 C0 D0 75 D0 10     ..2..........u..
001CD0: 12 0F FF D0 D0 D0 82 D0 83 D0 F0 D0 E0 32 EE C0     .............2..
001CE0: E0 7E 00 12 1B 65 EF FD EE FC D0 E0 FE 22 A3 E0     .~...e......."..
001CF0: 14 F0 B4 FF 06 12 1D 18 E0 14 F0 22 04 80 07 C3     ..........."....
001D00: CE 13 CE CF 13 CF D5 E0 F6 22 F8 8F F0 A4 FF E5     ........."......
001D10: F0 CE 88 F0 A4 2E FE 22 05 82 D5 82 02 15 83 15     ......."........
001D20: 82 22 FF FE FC F8 F0 E0 C0 80 00 25 82 F5 82 50     ."........%....P
001D30: 02 05 83 22 75 81 53 75 D0 00 02 07 7D 08 06 B6     ..."u.Su....}...
001D40: 00 02 18 06 22 75 81 53 E4 73 FF FF FF FF FF FF     ...."u.S.s......
001D50: FF FF FF FF FF FF FF FF FF FF FF FF FF FF FF FF     ................
001D60: FF FF FF FF FF FF FF FF FF FF FF FF FF FF FF FF     ................
001D70: FF FF FF FF FF FF FF FF FF FF FF FF FF FF FF FF     ................
001D80: FF FF FF FF FF FF FF FF FF FF FF FF FF FF FF FF     ................
001D90: FF FF FF FF FF FF FF FF FF FF FF FF FF FF FF FF     ................
001DA0: FF FF FF FF FF FF FF FF FF FF FF FF FF FF FF FF     ................
001DB0: FF FF FF FF FF FF FF FF FF FF FF FF FF FF FF FF     ................
001DC0: FF FF FF FF FF FF FF FF FF FF FF FF FF FF FF FF     ................
001DD0: FF FF FF FF FF FF FF FF FF FF FF FF FF FF FF FF     ................
001DE0: FF FF FF FF FF FF FF FF FF FF FF FF FF FF FF FF     ................
001DF0: FF FF FF FF FF FF FF FF FF FF FF FF FF FF FF FF     ................
001E00: FF FF FF FF FF FF FF FF FF FF FF FF FF FF FF FF     ................
001E10: FF FF FF FF FF FF FF FF FF FF FF FF FF FF FF FF     ................
001E20: FF FF FF FF FF FF FF FF FF FF FF FF FF FF FF FF     ................
001E30: FF FF FF FF FF FF FF FF FF FF FF FF FF FF FF FF     ................
001E40: FF FF FF FF FF FF FF FF FF FF FF FF FF FF FF FF     ................
001E50: FF FF FF FF FF FF FF FF FF FF FF FF FF FF FF FF     ................
001E60: FF FF FF FF FF FF FF FF FF FF FF FF FF FF FF FF     ................
001E70: FF FF FF FF FF FF FF FF FF FF FF FF FF FF FF FF     ................
001E80: FF FF FF FF FF FF FF FF FF FF FF FF FF FF FF FF     ................
001E90: FF FF FF FF FF FF FF FF FF FF FF FF FF FF FF FF     ................
001EA0: FF FF FF FF FF FF FF FF FF FF FF FF FF FF FF FF     ................
001EB0: FF FF FF FF FF FF FF FF FF FF FF FF FF FF FF FF     ................
001EC0: FF FF FF FF FF FF FF FF FF FF FF FF FF FF FF FF     ................
001ED0: FF FF FF FF FF FF FF FF FF FF FF FF FF FF FF FF     ................
001EE0: FF FF FF FF FF FF FF FF FF FF FF FF FF FF FF FF     ................
001EF0: FF FF FF FF FF FF FF FF FF FF FF FF FF FF FF FF     ................
001F00: FF FF FF FF FF FF FF FF FF FF FF FF FF FF FF FF     ................
001F10: FF FF FF FF FF FF FF FF FF FF FF FF FF FF FF FF     ................
001F20: FF FF FF FF FF FF FF FF FF FF FF FF FF FF FF FF     ................
001F30: FF FF FF FF FF FF FF FF FF FF FF FF FF FF FF FF     ................
001F40: FF FF FF FF FF FF FF FF FF FF FF FF FF FF FF FF     ................
001F50: FF FF FF FF FF FF FF FF FF FF FF FF FF FF FF FF     ................
001F60: FF FF FF FF FF FF FF FF FF FF FF FF FF FF FF FF     ................
001F70: FF FF FF FF FF FF FF FF FF FF FF FF FF FF FF FF     ................
001F80: FF FF FF FF FF FF FF FF FF FF FF FF FF FF FF FF     ................
001F90: FF FF FF FF FF FF FF FF FF FF FF FF FF FF FF FF     ................
```

```
001FA0: FF FF FF FF FF FF FF FF FF FF FF FF FF FF FF FF    ................
001FB0: FF FF FF FF FF FF FF FF FF FF FF FF FF FF FF FF    ................
001FC0: FF FF FF FF FF FF FF FF FF FF FF FF FF FF FF FF    ................
001FD0: FF FF FF FF FF FF FF FF FF FF FF FF FF FF FF FF    ................
001FE0: FF FF FF FF FF FF FF FF FF FF FF FF FF FF FF FF    ................
001FF0: FF FF FF FF FF FF FF FF FF FF FF FF FF FF BE A1    ................
```

Appendix B

```
000000: 02 1D 5A C3 EF 9D FF EE 9C FE 22 02 1C CE A3 E0    ..Z......."....
000010: 04 F0 70 06 12 1D 3E E0 04 F0 22 02 1C E9 FF FF    ..p...>..."....
000020: 4D 56 53 20 2D 20 58 49 56 20 20 56 20 31 2E 31    MVS - XIV  V 1.1
000030: 43 6F 70 79 72 69 67 68 74 20 20 31 39 38 34 20    Copyright  1984
000040: 62 79 20 4D 49 44 20 4C 61 62 73 2C 49 6E 63 2E    by MID Labs,Inc.
000050: 52 65 70 72 6F 64 75 63 74 69 6F 6E 20 20 20 20    Reproduction
000060: 50 72 6F 68 69 62 69 74 65 64 20 20 62 79 20 20    Prohibited  by
000070: 4C 61 77 2E 2A 2A 2A 2A 2A 2A 2A 2A 2A 2A 2A 2A    Law.************
000080: 75 33 01 75 88 02 75 8D 00 75 AB 00 75 89 10 75    u3.u..u..u..u..u
000090: 88 00 D2 03 E5 18 B4 FF 2A E5 43 44 80 F5 43 E5    ........*.CD..C
0000A0: 43 90 C4 04 F0 75 19 00 E5 19 D3 94 07 50 13 E5    C....u.......P..
0000B0: 19 90 C0 00 12 1D 51 74 20 F0 78 19 74 01 26 F6    ......Qt .x.t.&.
0000C0: 50 E6 22 E5 43 54 FC F5 43 E5 43 90 C4 04 F0 75    P.".CT..C.C....u
0000D0: 24 02 85 18 32 75 88 40 75 AB 88 22 90 E1 02 E0    $...2u.@u..."....
0000E0: 44 01 90 E1 02 F0 E5 18 60 25 15 19 75 1A 01 75    D.......`%..u..u
0000F0: 19 00 AE 19 AF 1A 74 58 C3 9F 74 02 9E 40 0E 78    ......tX..t..@.x
000100: 1A 74 01 26 F6 50 04 18 E4 36 F6 50 E5 80 D7 22    .t.&.P...6.P..."
000110: E5 43 54 FC F5 43 E5 43 90 C4 04 F0 E5 18 75 F0    .CT..C.C......u.
000120: 08 A4 FF AE F0 8F 18 75 19 00 E5 19 D3 94 07 50    .......u.......P
000130: 1B E5 18 25 19 90 1A 06 93 FE E5 19 90 C0 00 12    ...%............
000140: 1D 51 EE F0 78 19 74 01 26 F6 50 DE 22 75 18 00    .Q..x.t.&.P."u..
000150: E5 18 D3 94 07 50 13 E5 18 90 C0 00 12 1D 51 74    .....P........Qt
000160: 20 F0 78 18 74 01 26 F6 50 E6 22 75 A8 00 E5 43     .x.t.&.P."u...C
000170: 44 80 F5 43 E5 43 90 C4 04 F0 90 F0 01 E4 F0 90    D..C.C..........
000180: F0 03 E4 F0 90 F0 02 E4 F0 D2 97 D2 96 90 E1 03    ................
000190: E0 54 FD 44 08 90 E1 03 F0 90 E1 03 E0 44 10 90    .T.D.........D..
0001A0: E1 03 F0 90 C4 05 E4 F0 90 E1 02 E0 44 01 90 E1    ............D...
0001B0: 02 F0 75 18 07 12 01 10 E5 1A 75 F0 0A 84 AF F0    ..u.......u.....
0001C0: 7E 00 EF 24 30 90 C0 07 F0 E5 1A 75 F0 0A 84 FF    ~..$0......u....
0001D0: 7E 00 EF 24 30 90 C0 06 F0 80 FE 90 E1 01 E0 54    ~..$0..........T
0001E0: 02 70 2D 90 E0 07 E0 14 F0 90 C4 05 E4 F0 90 C4    .p-............
0001F0: 05 E4 F0 90 E1 01 E0 54 02 70 06 75 1A 0D 12 01    .......T.p.u....
000200: 6B 90 E0 07 E0 C3 94 F0 50 06 75 1A 0F 12 01 6B    k.......P.u....k
000210: 22 75 1C 01 75 1B 00 AE 1B AF 1C 74 28 8E 00 1E    "u..u......t(...
000220: 9F 40 12 30 92 01 22 78 1C 74 01 26 F6 50 04 18    .@.0.."x.t.&.P..
000230: E4 36 F6 50 E2 75 1A 0B 12 01 6B 22 75 89 01 75    .6.P.u....k"u..u
000240: 8A 02 75 8C F1 75 A8 82 75 B8 02 22 E5 36 C3 94    ..u..u..u.."6..
000250: 0A 50 01 22 75 36 00 30 93 06 E5 22 64 03 60 0E    .P."u6.0..."d.`.
000260: E5 22 C3 94 02 40 07 E5 22 D3 94 03 40 17 E5 31    ."...@.."...@..1
000270: FF 7E 00 0F BF 00 01 0E 74 1D 12 1D 30 0E 8E 1E    .~......t...0...
000280: 12 1A A7 80 03 12 1A 8C 22 E5 2D D3 94 01 40 53    ........".-...@S
000290: E5 2C D3 94 28 50 07 E5 2D D3 94 73 50 2D E5 2C    .,..(P..-..sP-.,
0002A0: D3 94 10 50 07 E5 2D D3 94 37 50 07 A2 94 83 92    ...P..-..7P.....
0002B0: 97 80 16 D2 97 74 0A F5 18 12 00 DC E5 2D D3 94    .....t.......-..
0002C0: 37 40 06 75 1A 06 12 01 6B 80 16 D2 97 74 0A F5    7@.u....k....t..
0002D0: 18 12 00 DC E5 2D D3 94 73 40 06 75 1A 06 12 01    .....-..s@.u....
0002E0: 6B 80 20 D2 97 74 0A F5 18 12 00 DC E5 2D C3 94    k. ..t.......-..
0002F0: 02 50 10 90 E1 03 E0 44 20 90 E1 03 F0 75 1A 02    .P.....D ....u..
000300: 12 01 6B 22 30 94 03 02 03 93 90 CC 00 E0 F4 54    ..k"0..........T
000310: 0F F5 25 90 CC 00 E0 F4 54 0F 65 25 60 03 75 25    ..%.....T.e%`.u%
000320: 00 E5 25 B4 01 0D 12 15 0E E5 22 D3 94 01 40 03    ..%......."...@.
000330: 02 03 B4 E5 25 64 08 60 05 E5 25 B4 0C 18 90 C4    ....%d.`..%.....
000340: 06 E4 F0 90 C4 06 E4 F0 90 C4 06 E4 F0 90 E1 01    ................
000350: E0 54 02 60 01 22 E5 25 70 19 E5 22 70 05 A2 93    .T.`.".%p..".p...
000360: B3 40 02 80 02 80 53 E5 22 B4 01 03 20 93 02 80    .@....S.".....
000370: 02 80 47 E5 22 C3 94 06 50 37 E5 25 54 0E F5 25    ..G."...P7.%T..%
000380: E5 25 60 28 E5 22 90 0C BD F8 28 28 73 80 28 80    .%`(."....((s.(.
000390: 29 E5 25 64 04 60 02 80 21 80 14 E5 25 64 02 60    ).%d.`..!...%d.`
0003A0: 02 80 17 80 0A 80 13 E5 25 64 0C 60 02 80 0B 80    ........%d.`....
0003B0: 02 80 0D 22 90 07 A1 12 1D 68 90 07 FE 12 1D 68    ..."....k
0003C0: 90 0C 8C 12 1D 6B 30 01 01 22 90 CC 00 E0 54 20    .....k0.."....T
0003D0: 60 06 75 18 06 12 00 B0 12 03 04 90 E1 03 E0 44    `.u............D
0003E0: 02 90 E1 03 F0 90 CC 00 E0 FE 90 CC 00 E0 4E 54    ..............NT
```

```
0003F0: 20 60 0C 90 E1 03 50 44 04 90 E1 03 F0 90 D9 90
000400: E1 03 E0 54 FD 90 E1 03 F0 74 0A F5 18 12 00 DC
000410: 90 CC 00 E0 FE 90 CC 00 E0 4E 54 20 60 02 80 B8
000420: 90 E1 03 E0 54 FB 90 E1 03 F0 75 18 FF 12 00 80
000430: 90 CC 00 E0 54 40 60 0D 75 18 01 12 00 80 74 82
000440: F5 45 12 15 61 12 16 EB 22 90 CC 00 E0 54 20 60
000450: 10 90 CC 00 E0 54 20 60 08 90 CC 00 E0 54 20 70
000460: 02 80 26 E5 22 D3 94 01 40 0A 20 94 05 12 15 0E
000470: 80 35 80 13 90 E1 03 E0 54 04 FF 7E 00 EF 60 01
000480: 22 20 94 03 12 15 0E 80 1D 90 E1 03 E0 54 04 FF
000490: 7E 00 EF 60 11 74 0A F5 18 12 00 DC 90 E1 03 E0
0004A0: 54 FB 90 E1 03 F0 22 90 07 A1 12 1D 6B 90 CC 00
0004B0: E0 54 80 60 08 90 E0 02 E0 04 F0 80 05 90 E0 02
0004C0: E4 F0 90 CC 00 E0 54 40 60 08 90 E0 00 12 00 0E
0004D0: 80 07 90 E0 00 E4 F0 A3 F0 90 E0 00 E0 FE A3 E0
0004E0: FF EF D3 94 86 EE 94 03 40 2C 90 E0 00 E4 F0 A3
0004F0: F0 75 A8 00 75 88 00 90 E1 02 50 44 01 90 E1 02
000500: F0 75 18 01 12 00 80 74 82 F5 45 12 15 61 75 A8
000510: 00 75 88 00 D3 22 90 E0 02 E0 D3 94 64 40 2A 90
000520: E0 02 E4 F0 75 A8 00 75 88 00 90 E1 02 E0 44 01
000530: 90 E1 02 F0 75 18 04 12 00 80 74 C8 F5 45 12 15
000540: 61 75 A8 00 75 88 00 D3 22 C3 22 12 19 19 30 00
000550: 01 22 E5 35 C3 94 32 50 01 22 75 35 00 E5 43 44
000560: 01 F5 43 E5 2C 75 F0 04 84 FF 7E 00 9F 18 E5 43
000570: 90 C4 04 F0 74 20 90 C0 03 F0 74 30 90 C0 02 F0
000580: 74 20 90 C0 04 F0 EF 75 F0 0A 84 AD F0 7C 00 ED
000590: 24 30 90 C0 01 F0 E5 18 75 F0 0A 84 FF 7E 00 8F
0005A0: 18 E5 18 70 08 74 20 90 C0 00 F0 80 08 E5 18 24
0005B0: 30 90 C0 00 F0 20 94 05 75 18 00 80 14 E5 2C 24
0005C0: 0F C3 95 2D 40 05 85 2D 18 80 06 E5 2C 24 0F F5
0005D0: 18 E5 18 C3 94 0F 50 05 75 18 00 80 07 E5 18 C3
0005E0: 94 0F F5 18 E5 18 04 75 F0 02 84 FF 7E 00 8F 18
0005F0: EF 54 01 70 08 74 30 90 C0 07 F0 80 08 74 35 90
000600: C0 07 F0 15 18 E5 18 75 F0 02 84 FF 7E 00 8F 18
000610: EF 75 F0 0A 84 AD F0 7C 00 ED 24 30 90 C0 06 F0
000620: E5 18 75 F0 0A 84 FF 7E 00 8F 18 E5 18 70 08 74
000630: 20 90 C0 05 F0 80 08 E5 18 24 30 90 C0 05 F0 22
000640: 75 1D 01 E5 1D D3 94 AA 50 49 74 01 F5 18 12 00
000650: DC 90 E8 00 E4 F0 12 02 11 90 E8 00 E0 C3 94 02
000660: 50 1E 74 0A F5 18 12 00 DC 90 E8 00 54 F0 12 02
000670: 11 90 E8 00 E0 C3 94 02 50 06 75 1A 02 12 01 6B
000680: 90 E8 00 E0 C3 94 19 50 02 80 0E 78 1D 74 01 26
000690: F6 50 B0 75 1A 03 12 01 6B 74 0A F5 18 12 00 DC
0006A0: 22 75 18 00 90 CC 00 E0 54 0F 64 0F 60 05 75 18
0006B0: 00 80 02 05 18 90 CC 00 E0 F4 54 0F B4 0C 05 E5
0006C0: 22 B4 05 02 80 03 12 03 04 74 01 F5 18 12 00 DC
0006D0: E5 1B C3 94 12 50 02 80 CB 22 C2 0A C2 B1 A2 B0
0006E0: 50 02 80 13 A2 B0 50 02 80 0D A2 B0 50 02 80 07
0006F0: 75 18 FF 12 00 80 22 12 03 04 30 0A 02 80 DD D2
000700: 0A 75 18 00 12 00 80 80 D3 E5 38 C3 94 FA 50 02
000710: 05 38 90 E1 01 E0 54 01 70 0F 90 E1 01 E0 54 01
000720: 70 07 E5 38 D3 94 F5 50 02 80 02 D2 09 90 E1 01
000730: E0 54 01 60 11 30 94 0E 30 09 0B 90 E1 01 E0 54
000740: 01 60 03 20 94 02 80 05 C2 09 75 38 00 E5 38 C3
000750: 94 3F 50 0C 90 E1 02 E0 54 FE 90 E1 02 F0 80 0A
000760: 90 E1 02 E0 44 01 90 E1 02 F0 22 85 1C 18 12 01
000770: 10 12 06 A1 75 1D 01 E5 1D D3 94 10 50 12 74 0A
000780: F5 18 12 00 DC 12 03 04 78 1D 74 01 26 F6 50 E7
000790: 22 12 1C 6C 12 1B 39 12 13 DE 75 22 04 D2 07 80
0007A0: 00 75 A8 00 12 13 5D 90 E1 03 E0 54 04 FF 7E 00
0007B0: EF 60 02 C2 01 E5 22 C3 94 06 50 3F E5 22 90 1A
0007C0: 86 93 F5 43 E5 43 90 C4 04 F0 75 42 3F E5 22 64
0007D0: 04 60 05 E5 22 B4 05 03 75 42 BF E5 42 90 C4 03
0007E0: F0 E5 22 90 0C CF F8 28 28 73 E0 74 80 72 80 70
0007F0: 02 09 66 02 0A 7D 02 0A 7D 80 03 02 0C 8C 75 A8
000800: 00 75 88 00 E5 25 70 0D 30 93 05 75 22 00 80 03
000810: 75 22 01 80 2C E5 25 B4 09 0F E5 22 64 04 60 04
000820: D2 07 80 02 B2 07 75 22 04 E5 25 B4 02 03 75 22
000830: 03 E5 25 B4 0C 03 75 22 05 E5 25 B4 04 03 75 22
000840: 02 E5 22 C3 94 04 50 15 90 C4 05 E4 F0 90 E1 01
000850: E0 54 02 70 09 90 C4 05 E4 F0 12 01 DB 02 07 A1
```

```
000860: 75 A8 00 75 88 00 E5 25 B4 04 07 74 01 F5 1C 12
000870: 07 6B 12 06 DA 12 03 C6 75 A8 00 75 88 00 90 E1
000880: 03 E0 54 DF 90 E1 03 F0 90 E8 04 E4 F0 12 02 11
000890: 90 E8 00 E0 75 F0 F1 A4 FF AE F0 8E 2C E5 43 44
0008A0: 01 F5 43 E5 43 90 C4 04 F0 75 3B 01 12 06 40 75
0008B0: 35 2D 12 02 3C 75 23 02 75 88 10 90 E0 00 E4 F0
0008C0: A3 F0 90 E0 02 E4 F0 12 04 AD 50 02 80 DB 30 94
0008D0: 1E 90 E1 03 E0 44 10 90 E1 03 F0 AE 40 AF 41 74
0008E0: E8 D3 9F 74 FD 9E 40 05 78 40 12 1D 63 80 30 AE
0008F0: 40 AF 41 74 2C D3 9F 74 01 9E 40 08 75 41 00 75
000900: 40 00 80 1B 75 41 00 75 40 00 75 A8 00 75 88 00
000910: 90 E1 02 E0 44 01 90 E1 02 F0 12 18 17 80 8A 30
000920: 94 08 90 E1 01 E0 54 01 70 02 80 0C 90 E1 02 E0
000930: 54 FE 90 E1 02 F0 80 0A 90 E1 02 E0 44 01 90 E1
000940: 02 F0 12 03 04 12 04 49 12 02 89 12 05 4B 90 E0
000950: 07 E0 C3 94 80 50 09 90 E0 07 E0 F5 1A 12 01 6B
000960: 12 01 DB 02 09 C7 75 A8 00 75 88 00 E5 25 B4 02
000970: 07 74 05 F5 1C 12 07 6B 12 03 C6 75 A8 00 75 88
000980: 00 90 E1 03 E0 54 DF 90 E1 03 F0 90 E8 04 E4 F0
000990: 12 02 11 90 E8 00 E0 75 F0 F1 A4 FF AE F0 8E 2C
0009A0: 75 31 00 E5 43 44 01 F5 43 E5 43 90 C4 04 F0 75
0009B0: 3B 01 12 06 40 75 35 2D 75 89 11 75 8A 02 75 8C
0009C0: B0 75 88 08 75 8B 02 75 8D D0 75 24 01 75 30 FF
0009D0: 75 23 02 75 A8 8A 75 88 50 75 2F 02 75 2E 00 90
0009E0: E0 00 E4 F0 A3 F0 90 E0 02 E4 F0 30 94 1E 90 E1
0009F0: 03 E0 44 10 90 E1 03 F0 AE 40 AF 41 74 E8 D3 9F
000A00: 74 FD 9E 40 05 78 40 12 1D 63 80 42 75 30 FF AE
000A10: 40 AF 41 74 2C D3 9F 74 01 9E 40 12 75 41 00 75
000A20: 40 00 90 E1 03 E0 54 EF 90 E1 03 F0 80 20 75 41
000A30: 00 75 40 00 75 A8 00 75 88 00 D2 96 90 F0 01 E4
000A40: F0 90 F0 03 E4 F0 D2 97 12 18 17 02 09 AF 12 03
000A50: 04 12 04 AD 50 03 02 09 AF 12 04 49 12 02 89 12
000A60: 05 4B 12 02 4C 90 E0 07 E0 C3 94 80 50 09 90 E0
000A70: 07 E0 F5 1A 12 01 6B 12 01 DB 02 09 EB 75 A8 00
000A80: 75 88 00 E5 22 B4 05 16 E5 25 64 01 60 07 74 0A
000A90: F5 1C 12 07 6B C2 07 12 06 DA D2 B1 80 18 E5 25
000AA0: B4 08 13 30 07 09 74 0F F5 1C 12 07 6B 80 07 74
000AB0: 0D F5 1C 12 07 6B 12 03 C6 75 A8 00 75 88 00 90
000AC0: E1 03 E0 54 DF 90 E1 03 F0 75 2C F0 75 31 00 75
000AD0: 3A 00 E5 43 44 01 F5 43 E5 43 90 C4 04 F0 30 07
000AE0: 06 75 18 0F 12 01 10 C2 09 75 38 FF 12 06 40 75
000AF0: 35 2D 75 89 11 75 8A 02 75 8C B0 75 88 08 75 8B
000B00: 02 75 8D D0 75 23 04 75 30 00 75 24 06 75 A8 8A
000B10: 90 E0 00 E4 F0 A3 F0 90 E0 02 E4 F0 75 44 00 C2
000B20: 04 75 3B 01 C2 09 75 3E 00 75 39 00 75 3A 64 C2
000B30: 06 D2 97 75 88 50 30 07 37 E5 43 44 90 F5 43 E5
000B40: 43 90 C4 04 F0 90 E1 02 E0 44 01 90 E1 02 F0 D2
000B50: 97 A2 94 72 94 50 0C 90 E1 03 E0 44 10 90 E1 03
000B60: F0 80 0A 90 E1 03 E0 54 EF 90 E1 03 F0 02 0C 04
000B70: 30 94 1C 90 E0 20 74 17 F0 A3 74 70 F0 75 41 00
000B80: 75 40 00 90 E1 03 E0 44 10 90 E1 03 F0 80 77 90
000B90: E1 02 E0 44 01 90 E1 02 F0 A2 97 40 06 90 E0 20
000BA0: 12 1D 14 90 E0 20 E0 FE A3 E0 FF EF 4E 70 06 75
000BB0: 1A 04 12 01 6B E5 2D C3 94 13 50 07 A2 97 B3 72
000BC0: 06 40 02 80 25 75 A8 00 75 88 00 A2 05 40 06 E5
000BD0: 43 44 80 F5 43 E5 43 90 C4 04 F0 74 14 F5 1B 12
000BE0: 00 DC D2 97 12 18 17 02 0A DE 78 40 12 1D 63 AE
000BF0: 40 AF 41 EF D3 94 D0 EE 94 07 40 0A 90 E1 03 E0
000C00: 54 EF 90 E1 03 F0 12 03 04 12 04 AD 50 03 02 0A
000C10: DE 12 04 49 20 07 40 12 05 4B 90 E1 03 E0 54 01
000C20: FF 7E 00 EF 70 04 E5 35 60 02 80 06 74 88 90 C0
000C30: 04 F0 E5 2D C3 94 02 50 07 74 0A F5 19 12 00 DC
000C40: E5 2D C3 94 02 50 10 90 E1 03 E0 44 20 90 E1 03
000C50: F0 75 1A 02 12 01 6B 12 02 4C 22 B4 05 05 A2 22
000C60: 07 B3 40 02 80 03 12 07 09 90 E0 07 E0 C3 94 80
000C70: 50 09 90 E0 07 E0 F5 1A 12 01 6B 90 E1 01 E0 54
000C80: 02 60 06 75 1A 0E 12 01 6B 02 0B 36 74 FF 90 E1
000C90: 03 F0 90 F0 03 E4 F0 90 F0 02 E4 F0 75 43 80 D2
000CA0: 97 D2 96 90 E1 02 E0 44 01 90 E1 02 F0 75 18 07
000CB0: 12 01 10 74 41 90 C0 06 F0 C2 90 80 FE 02 03 8D
000CC0: 02 03 8F 02 03 91 02 03 9B 02 03 A5 02 03 A7 02
```

```
000CD0: 07 EA 02 07 EC 02 07 EE 02 07 F0 02 07 F3 02 07
000CE0: F6 75 4B 1E 75 4A 00 75 4A 02 75 4B 58 75 4B 44
000CF0: 75 4A 00 75 4B 37 75 4A 00 30 92 06 E5 22 64 02
000D00: 60 02 80 26 90 E8 00 E4 F0 75 4B 28 75 4A 00 75
000D10: 4A 03 75 4B 21 75 4B 29 75 4A 00 75 4A 01 75 4B
000D20: 93 30 92 06 74 0B 90 E0 07 F0 75 4B 01 75 4A 00
000D30: AE 4A AF 4B 74 28 BE 00 15 9F 40 12 30 92 01 22
000D40: 78 4B 74 01 26 F6 50 04 1B E4 36 F6 50 E2 74 0B
000D50: 90 E0 07 F0 22 75 8C D3 75 8A FF 05 35 05 36 05
000D60: 34 E5 3B 85 51 05 A2 05 B3 40 02 80 0C E5 43 44
000D70: 80 F5 43 E5 43 90 C4 04 F0 E5 3B 60 02 15 3B E5
000D80: 3B 70 07 E5 22 D3 94 01 50 02 80 3D A2 94 B3 40
000D90: 07 E5 2D C3 94 14 50 05 75 51 00 80 2C 74 AF C3
000DA0: 95 2D 75 F0 8C A4 FF AE F0 EE 24 0F F5 51 F5 3B
000DB0: E5 2D D3 94 AF 40 06 74 0C F5 51 F5 3B E5 43 54
000DC0: 7F F5 43 E5 43 90 C4 04 F0 E5 3B C3 94 FA 50 02
000DD0: 05 3B E5 23 D3 94 04 40 03 02 10 1B E5 23 90 13
000DE0: 39 F8 28 28 73 80 0B 80 3F 02 0E 96 02 10 00 02
000DF0: 0E C0 AE 26 AF 27 EF D3 94 08 EE 94 07 40 03 02
000E00: 10 1B AE 2A AF 2B AC 26 AD 27 EF 2D FD EE 3C FC
000E10: 8C 2A 8D 2B ED D3 94 00 EC 94 B0 40 09 75 2A B0
000E20: 75 2B 00 75 23 01 80 33 AE 28 AF 29 EF D3 94 0B
000E30: EE 94 07 40 03 02 10 1B AE 2A AF 2B AC 28 AD 29
000E40: 12 00 03 8E 2A 8F 2B 74 00 D3 9F 74 3E 9E 40 09
000E50: 75 2A 3E 75 2B 00 75 23 00 80 00 E5 22 60 03 02
000E60: 10 1B 90 F0 03 E4 F0 90 E1 03 E0 44 C8 90 E1 03
000E70: F0 30 94 11 E5 2B C4 54 0F 90 F0 01 F0 E5 2A 90
000E80: F0 02 F0 80 10 75 2A 27 75 2B 00 90 F0 01 E4 F0
000E90: 90 F0 02 E4 F0 22 E5 22 64 02 60 05 E5 22 B4 03
000EA0: 02 80 03 02 10 1B 90 E8 04 E4 F0 12 0C E1 90 E8
000EB0: 00 E0 75 F0 A1 A4 FF AE F0 EE 54 FC F5 2C 80 3A
000EC0: E5 22 64 04 60 05 E5 22 B4 05 02 80 03 02 10 1B
000ED0: 90 E8 04 E4 F0 12 0C E1 90 E8 00 E0 75 F0 05 B4
000EE0: FF 7E 00 EF 24 33 F5 3A 90 E8 00 E0 75 F0 DD A4
000EF0: FF AE F0 EE 54 FC F5 2C 80 00 90 E8 03 E4 F0 12
000F00: 0C E1 90 E9 00 E0 F4 F5 39 90 E8 05 E4 F0 E5 22
000F10: 64 04 60 05 E5 22 B4 05 02 80 2F E5 39 D3 94 1B
000F20: 40 09 E5 39 C3 94 1C F5 39 80 03 75 39 00 E5 39
000F30: 75 F0 12 A4 FF AE F0 74 04 12 1D 22 EF 85 2C F0
000F40: A4 FF AE F0 8E 4C 8F 4D 80 2D E5 39 D3 94 39 40
000F50: 09 E5 39 C3 94 3A F5 39 80 03 75 4E 00 E5 4E 75
000F60: F0 53 A4 FF AE F0 74 06 12 1D 22 EF 85 2C F0 A4
000F70: FF AE F0 8E 4C 8F 4D 12 0C E1 90 E8 00 E0 F5 4E
000F80: 90 E8 00 E4 F0 12 0C E1 90 E8 00 E0 F5 2D E5 22
000F90: C3 94 02 40 07 E5 22 D3 94 05 40 02 80 7A 30 94
000FA0: 1B E5 2D D3 94 01 40 14 E5 4D 45 4C 60 0E E5 22
000FB0: 64 04 60 05 E5 22 B4 05 05 30 07 02 80 13 E5 4D
000FC0: C4 54 0F 90 F0 01 F0 E5 4C 24 0F 90 F0 03 F0 80
000FD0: 0A 90 F0 01 E4 F0 90 F0 03 E4 F0 90 E9 05 E4 F0
000FE0: 12 0C E1 90 E8 00 E0 C3 95 4E C3 94 03 40 0D 90
000FF0: E8 00 E0 F4 04 25 4E C3 94 03 50 03 85 4E 31 22
001000: E5 22 64 01 60 02 80 10 90 F0 03 E4 F0 90 E1 03
001010: E0 44 C8 90 E1 03 F0 22 90 0C 8C 12 1D 68 75 50
001020: 00 E5 50 D3 94 07 50 1B E5 4F 90 19 7E 93 FE E5
001030: 50 90 C0 00 12 1D 51 EE F0 05 4F 78 50 74 01 26
001040: F6 50 DE 22 E5 24 90 13 48 F8 28 28 73 B0 11 02
001050: 11 1D 02 12 84 02 12 C6 02 13 1F 80 6C 02 11 3A
001060: 75 8B 02 75 8D CA E5 31 D3 94 F5 40 05 75 8D CF
001070: 80 22 E5 31 D3 94 E5 40 05 75 8D CE 90 16 E5 31
001080: D3 94 D0 40 05 75 8D CC 80 0A E5 31 D3 94 B4 40
001090: 03 75 8D CB E5 22 64 03 60 03 02 13 33 C2 96 75
0010A0: 24 01 7E A6 7F 3B E5 31 75 F0 02 84 FD 7C 00 ED
0010B0: 24 0C 8E 14 8F 15 FF 12 1D 04 74 FF 62 14 62 15
0010C0: 8C 2E 8D 2F E5 2E F5 30 22 75 8B 02 75 8D 70 E5
0010D0: 22 64 04 60 05 E5 22 B4 05 02 80 03 02 13 33 D2
0010E0: 06 A2 94 B3 92 97 75 24 06 7E C2 7F 10 E5 31 75
0010F0: F0 08 84 FD 7C 00 ED 24 0F 8E 14 8F 15 FF 12 1D
001100: 04 74 FF 62 14 62 15 8C 2E 8D 2F E5 2E F5 30 22
001110: D2 96 E5 22 64 03 60 03 02 13 33 A2 93 82 94 40
001120: 01 22 05 30 E5 30 60 07 75 8B 02 75 8D 00 22 75
001130: 24 00 75 8B 02 E5 2F F5 8D 22 E5 22 64 04 60 05
```

```
001140: E5 22 B4 05 02 80 03 02 13 33 30 07 03 D2 97 22    ."........30...."
001150: 75 8D DB 75 88 FF E5 2D C3 94 2F 50 02 C2 0C E5    u..u...-../P....
001160: 3E C3 94 03 50 07 E5 39 C3 94 28 50 02 80 16 C2    >...P..9..(P....
001170: 0C 90 E1 03 E0 44 C1 90 E1 03 F0 75 3C 04 75 3E    .....D.....u<.u>
001180: 03 C2 97 D2 08 E5 39 C3 94 37 40 17 20 0C 02 C2    ......9..7@. ...
001190: 97 90 E1 03 E0 44 C1 90 E1 03 F0 75 3D 28 75 3E    .....D.....u=(u>
0011A0: 04 D2 06 E5 3E B4 04 07 E5 2D D3 94 3F 50 02 80    ....>....-..?P..
0011B0: 02 D2 0C E5 39 D3 94 1E 50 07 E5 3E C3 94 04 40    ....9...P..>...@
0011C0: 02 80 0B D2 97 75 3E 01 E5 3C 60 02 15 3C E5 3E    .....u>..<`..<.>
0011D0: B4 01 06 E5 22 64 04 60 02 80 1E E5 3C 70 0E 90    ...."d.`....<p..
0011E0: E1 01 E0 FE 90 E1 01 E0 5E 54 01 70 02 80 0A 90    ........^T.p....
0011F0: E1 03 E0 54 3E 90 E1 03 F0 E5 3E B4 04 07 E5 39    ...T>.....>....9
001200: D3 94 1E 40 02 80 1C E5 2D C3 94 13 50 07 D2 97    ...@....-...P...
001210: 75 3E 03 80 0E C2 97 15 3D E5 3D F0 06 74 07 90    u>......=.=..t..
001220: E0 07 F0 30 94 08 E5 3E B4 04 03 20 0C 07 75 8B    ...0...>... ..u.
001230: 02 75 8D 2C 22 E5 30 04 75 F0 33 94 AF F0 7E 00    .u.,".0.u.3...~.
001240: 8F 30 E5 31 75 F0 B1 A4 FD AC F0 EC 75 F0 04 E4    .0.1u.......u...
001250: FD 7C 00 ED 24 02 F5 3F E5 3F D3 94 2D 50 07 E5    .|..$.?.?..-P..
001260: 31 D3 94 FA 40 03 75 3F 33 E5 30 70 06 C2 97 D2    1...@.u?3.0p....
001270: 08 80 10 30 08 07 E5 30 C3 95 3F 50 02 80 04 C2    ...0...0..?P....
001280: 08 D2 97 22 15 33 E5 33 70 3B E5 32 C3 94 05 50    ...".3.3p;.2...P
001290: 04 E5 32 70 0E 30 03 06 E5 32 64 05 60 05 E5 32    ..2p.0...2d.`..2
0012A0: 84 07 0E C2 03 E5 43 54 7F F5 43 E5 43 90 C4 04    ......CT..C.C...
0012B0: F0 E5 32 75 F0 10 A4 FF AE F0 8F 4F 12 10 1E 75    ..2u.......O...u
0012C0: 33 0A 75 24 03 22 15 33 E5 32 84 01 2A E5 33 C3    3.u$.".3.2..*.3.
0012D0: 94 06 50 07 E5 33 D3 94 04 50 02 80 0E E5 43 44    ..P..3...P....CD
0012E0: 80 F5 43 E5 43 90 C4 04 F0 80 0C E5 43 54 7F F5    ..C.C.......CT..
0012F0: 43 E5 43 90 C4 04 F0 E5 33 70 23 E5 43 44 80 F5    C.C.....3p#.CD..
001300: 43 E5 43 90 C4 04 F0 E5 32 75 F0 10 A4 FF AE F0    C.C.....2u......
001310: 8F 24 08 F5 4F 12 10 1E 75 33 0A 75 24 04 22 15    .$..O...u3.u$.".
001320: 33 E5 33 70 0D 74 80 F5 4F 12 10 1E 75 33 04 75    3.3p.t..O...u3.u
001330: 24 02 22 90 0C 8C 12 1D 6B 02 0D E5 02 0D E7 02    $.".....k.......
001340: 0D EF 02 0D EC 02 0D 4D 02 10 4F 02 10               .......M..O..
001350: 52 02 10 55 02 10 59 02 10 5B 02 10 5D 75 A8 00    R..U..Y..[..]u..
001360: 75 88 00 75 88 00 75 89 00 74 5F 90 E1 02 F0 90    u..u..u..t_.....
001370: F0 01 E4 F0 90 F0 02 E4 F0 90 F0 03 E4 F0 D2 96    ................
001380: 90 E1 02 E0 44 01 90 E1 02 F0 74 FF 90 E0 07 F0    ....D.....t.....
001390: 75 27 00 75 26 00 75 29 00 75 28 00 75 2B 00 75    u'.u&.u).u(.u+.u
0013A0: 2A 00 C2 00 75 34 00 90 E1 03 E0 54 CF 44 0B 90    *...u4.....T.D..
0013B0: E1 03 F0 12 1A 8C 90 CC 00 E0 54 10 60 0F 75 18    ..........T.`.u.
0013C0: 03 12 00 80 75 18 FA 12 00 DC 75 A8 00 12 01 4D    ....u.....u....M
0013D0: 90 E0 02 E4 F0 75 41 00 75 40 00 C2 04 22 75 43    .....uA.u@..."uC
0013E0: 80 E5 43 90 C4 04 F0 74 4E 90 E1 00 F0 74 4F 90    ..C....tN....tO.
0013F0: E1 02 F0 74 FF 90 E1 03 F0 D2 97 D2 96 90 F0 01    ...t............
001400: E4 F0 90 F0 02 E4 F0 90 F0 03 E4 F0 90 E1 03 E0    ................
001410: 54 DF 90 E1 03 F0 75 37 00 C2 01 C2 02 75 18 28    T.....u7.....u.(
001420: 12 00 DC 75 42 00 12 1A 8C 90 E8 00 E4 F0 12 02    ...uB...........
001430: 11 90 CC 00 E0 54 10 60 06 75 18 03 12 00 80 90    .....T.`.u......
001440: CC 00 E0 54 10 60 0A 90 CC 00 E0 54 0F 64 0F 60    ...T.`.....T.d.`
001450: 02 80 02 80 EA 75 18 0A 12 00 DC C2 0B 30 94 0B    .....u.......0..
001460: 75 18 07 12 00 80 D2 0B 75 47 00 75 46 01 75 45    u.......uG.uF.uE
001470: 00 AE 45 AF 46 74 20 C3 9F 74 03 9E 40 27 30 94    ..E.Ft .t..@'0..
001480: 05 75 47 00 80 02 05 47 75 18 01 12 00 DC E5 47    .uG....Gu......G
001490: D3 94 14 40 02 80 14 78 46 74 01 26 F6 50 04 18    ...@...xFt.&.P..
0014A0: E4 36 F6 50 CC 75 1A 11 12 01 6B 75 A8 00 75 88    .6.P.u....ku..u.
0014B0: 00 E5 43 44 80 F5 43 E5 43 90 C4 04 F0 30 0B 0C    ..CD..C.C....0..
0014C0: 75 18 08 12 01 10 75 18 64 12 00 DC 90 E8 00 E0    u.....u.d.......
0014D0: D3 94 13 50 09 90 E8 00 E0 C3 94 0B 50 2C 75 19    ...P........P,u.
0014E0: 32 12 00 DC 90 E8 00 E4 F0 12 02 11 90 E8 00 E0    2...............
0014F0: F5 2D 90 E8 00 E0 D3 94 13 50 09 90 E8 00 E0 C3    .-.......P......
001500: 94 0B 50 06 75 1A 05 12 01 6B 12 01 4D 22 90 E1    ..P.u....k..M"..
001510: 02 E0 44 01 90 E1 02 F0 90 E1 03 E0 54 01 FF 7E    ..D.........T..~
001520: 00 EF 70 10 90 E1 03 E0 44 01 90 E1 03 F0 75 18    ..p.....D.....u.
001530: 14 12 00 DC 90 E1 03 E0 44 04 90 E1 03 F0 75 19    ........D.....u.
001540: 1E 12 00 DC 90 E1 03 E0 54 FE 90 E1 03 F0 75 1C    ........T.....u.
001550: 3C 12 00 DC 90 E1 03 E0 44 01 90 E1 03 F0 C2 01    <.......D.......
001560: 22 D2 96 90 E1 03 E0 54 F7 90 E1 03 F0 D2 97 90    "......T........
001570: F0 03 E4 F0 90 F0 01 E4 F0 75 18 14 12 00 DC 75    .........u.....u
001580: 41 00 75 40 00 90 E1 03 E0 54 FD 90 E1 03 F0 C2    A.u@.....T......
001590: 0B 75 49 01 75 48 00 AE 48 AF 49 E5 45 BE 00 03    .uI.uH..H.I.E...
0015A0: 9F 50 03 02 16 7C 75 47 01 75 46 00 AE 46 AF 47    .P...|uG.uF..F.G
```

```
001580: 74 08 C3 9F 74 07 9E 40 0E 78 47 74 01 26 F6 50     t..t..@.xGt.&.P
0015C0: 04 18 E4 36 F6 50 E5 90 E1 01 E0 FE 90 E1 01 E0     ...6.P..........
0015D0: 5E 54 01 60 02 D2 08 90 E8 05 E4 F0 12 02 11 90     ^T.`............
0015E0: E8 00 E0 F5 31 90 E8 00 E4 F0 12 02 11 90 E8 00     ....1...........
0015F0: E0 C3 94 02 50 27 75 18 14 12 00 DC 90 E8 00 E4     ....P'u.........
001600: F0 12 02 11 90 E8 00 E0 C3 94 02 50 10 90 E1 03     ...........P....
001610: E0 54 DF 90 E1 03 F0 75 1A 02 12 01 6B E5 36 24     .T.....u....k.6$
001620: 02 F5 36 12 02 4C E5 22 B4 04 03 20 0B 02 80 14     ..6..L."........
001630: AE 48 AF 49 74 07 8E 00 03 9F 50 0A 90 E1 03 E0     .H.It.....P.....
001640: 54 FE 90 E1 03 F0 AE 48 AF 49 74 25 BE 00 03 9F     T......H.It%....
001650: 50 19 20 94 0C E0 54 EF 90 E1 03 F0 80     P. ...T........
001660: 0A 90 E1 03 E0 44 10 90 E1 03 F0 78 49 74 01 26     .....D.....xIt.&
001670: F6 50 04 18 E4 36 F6 40 03 02 15 97 90 E1 03 E0     .P...6.@........
001680: 44 02 44 08 90 E1 03 F0 75 18 FF 12 00 80 90 CC     D.D.....u.......
001690: 00 E0 54 40 60 0B 75 18 02 12 00 80 12 03 04 80     ..T@`.u.........
0016A0: F8 22 90 E1 03 E0 44 10 90 E1 03 F0 75 18 09 12     ."....D.....u...
0016B0: 01 10 D2 02 75 18 64 12 00 DC 75 45 01 E5 45 D3     ....u.d...uE..E.
0016C0: 94 3C 50 19 75 18 0A 12 00 DC 12 03 04 A2 94 82     .<P.u...........
0016D0: 94 50 02 80 08 78 45 74 01 26 F6 50 E0 90 E1 03     .P...xEt.&.P....
0016E0: E0 54 EF 90 E1 03 F0 12 01 4D 22 D2 08 75 18 05     .T.......M"..u..
0016F0: 12 01 10 75 18 0A 12 00 DC D2 97 75 18 0C 12 00     ...u.......u....
001700: DC 90 E1 03 E0 44 20 54 FD 90 E1 03 F0 75 18 0C     .....D T.....u..
001710: 12 00 DC 90 E1 03 E0 54 F7 90 E1 03 F0 75 47 00     .......T.....uG.
001720: 75 46 00 E5 47 C3 94 C8 50 07 E5 46 C3 94 48 40     uF..G...P..F..K@
001730: 02 80 2F 05 47 90 E8 00 E4 F0 75 18 01 12 00 DC     ../.G.....u.....
001740: 12 02 11 90 E8 00 E0 F5 46 E5 46 C3 94 02 50 10     ........F.F...P.
001750: 90 E1 03 E0 54 DF 90 E1 03 F0 75 1A 02 12 01 6B     ....T.....u....k
001760: 80 C1 90 E1 03 E0 44 02 90 E1 03 F0 75 18 0C 12     ......D.....u...
001770: 00 DC 90 E1 03 E0 44 08 90 E1 03 F0 90 CC 00 E0     ......D.........
001780: 54 20 60 06 12 15 0E 02 18 11 75 18 64 12 00 DC     T `.......u.d...
001790: 90 E8 00 E4 F0 12 02 11 E5 46 C3 94 02 40 09 90     .........F...@..
0017A0: E8 00 E0 C3 94 02 50 10 90 E1 03 E0 54 DF 90 E1     ......P.....T...
0017B0: 03 F0 75 1A 02 12 01 6B E5 46 C3 94 4B 40 0E 90     ..u....k.F..K@..
0017C0: E8 00 E0 FE E5 46 C3 94 19 C3 9E 40 02 80 18 75     .....F.....@...u
0017D0: 18 02 12 01 10 75 18 32 12 00 DC D2 01 20 02 03     .....u.2..... ..
0017E0: 12 16 A2 12 01 4D 22 30 0B 05 C2 08 02 17 01 75     .....M"0.......u
0017F0: 18 05 12 00 80 90 CC 00 E0 54 20 60 08 90 CC 00     .........T `....
001800: E0 54 20 70 02 80 05 12 15 0E 80 05 12 03 04 80     .T p............
001810: E4 90 07 A1 12 1D 6B 90 E0 10 E4 F0 A3 F0 D2 96     ......k.........
001820: D2 97 90 F0 03 E4 F0 90 F0 01 E4 F0 C2 08 90 E1     ................
001830: 03 E0 54 F7 90 E1 03 F0 75 2D 0F A2 05 40 06 E5     ..T.....u-...@..
001840: 43 44 80 F5 43 E5 43 90 C4 04 F0 C2 04 75 18 0A     CD..C.C......u..
001850: 12 00 DC 90 E1 03 E0 54 FD 90 E1 03 F0 75 46 01     .......T.....uF.
001860: 75 45 00 AE 45 AF 46 74 2C C3 9F 74 01 9E 50 03     uE..E.Ft,..t..P.
001870: 02 19 0C 74 01 52 07 7E 00 EF 4E 70 06 75 18 01     ...t.R.~..Np.u..
001880: 12 00 DC 90 E1 01 E0 FE 90 E1 01 E0 5E 54 01 60     ............^T.`
001890: 02 D2 08 30 94 02 80 74 90 E8 03 E4 F0 12 02 11     ...0...t........
0018A0: 90 E8 00 E0 C3 94 E1 50 06 90 E0 10 12 00 0E 90     .......P........
0018B0: E0 10 E0 F5 A3 E0 FF 74 79 BE 00 03 9F 50 06 75     .......ty....P.u
0018C0: 1A 10 12 01 6B AE 45 AF 46 74 19 BE 00 03 9F 50     ....k.E.Ft.....P
0018D0: 03 20 08 02 80 0F E5 22 B4 04 0A 90 E1 03 E0 54     . ....."......T
0018E0: FE 90 E1 03 F0 AE 45 AF 46 74 7D BE 00 03 9F 50     .....E.Ft)....P
0018F0: 0A 90 E1 03 E0 54 EF 90 E1 03 F0 78 46 74 01 26     .....T.....xFt.&
001900: F6 50 04 18 E4 36 F6 40 03 02 18 63 90 E1 03 E0     .P...6.@...c...
001910: 44 02 44 08 90 E1 03 F0 22 90 CC 00 E0 54 10 70     D.D....."....T.p
001920: 1B C2 05 75 37 00 20 94 06 E5 43 44 80 F5 43 E5     ...u7. ...CD..C.
001930: 43 90 C4 04 F0 C2 00 75 34 D7 80 41 E5 34 D3 94     C......u4..A.4..
001940: DC 40 3A 75 34 00 B2 00 30 00 21 E5 37 C3 94 05     .@:u4...0.!.7...
001950: 50 10 E5 43 54 7F F5 43 E5 43 90 C4 04 F0 D2 05     P..CT..C.C......
001960: 05 37 75 34 8C 75 18 04 12 01 10 22 E5 43 44 80     .7u4.u....."..CD.
001970: F5 43 E5 43 90 C4 04 F0 C2 05 75 35 FA 22 20 43     .C.C......u5." C
001980: 48 45 43 4B 20 20 20 43 41 42 4C 45 20 20 54 52     HECK   CABLE  TR
001990: 41 4E 53 46 45 52 54 52 41 4E 53 46 45 52 20 43     ANSFERTRANSFER C
0019A0: 48 45 43 4B 20 20 43 41 53 53 45 54 54 45 4C 4F     HECK  CASSETTELO
0019B0: 57 20 41 49 52 20 50 52 45 53 53 55 52 45 20 43     W AIR PRESSURE C
0019C0: 48 45 43 4B 20 20 43 4F 4E 54 41 43 54 53 20 56     HECK  CONTACTS V
0019D0: 41 43 55 55 4D 20 20 20 4C 45 41 4B 20 20 20 49     ACUUM   LEAK   I
0019E0: 4E 53 45 52 54 20 43 41 53 53 45 54 54 45 52 45     NSERT CASSETTERE
0019F0: 4C 45 41 53 45 20 20 46 4F 4F 54 53 57 20 20 20     LEASE  FOOTSW   
001A00: 20 20 20 20 20 20 53 43 49 53 53 4F 52 53 20 20         SCISSORS  
001A10: 46 52 41 47 20 20 20 20 4F 4B 20 20 20 54 52     FRAG    OK   TR
```

```
001A20: 41 4E 53 46 45 52 4C 4F 57 20 20 41 49 52 43 48    ANSFERLOW  AIRCH
001A30: 45 43 4B 49 4E 47 20 45 52 52 4F 52 20 20 45 52    ECKING ERROR  ER
001A40: 52 4F 52 20 20 20 4D 56 53 20 56 31 2E 31 49 52    ROR   MVS V1.1IR
001A50: 52 20 4F 50 45 4E 49 2F 41 20 46 52 41 47 20 4D    R OPENI/A FRAG M
001A60: 55 4C 54 49 20 20 20 20 50 52 4F 50 20 20 20 20    ULTI    PROP
001A70: 49 2F 41 20 20 20 20 20 56 49 54 20 20 20 49 52    I/A     VIT   IR
001A80: 52 20 4F 4E 4C 59 88 E8 88 A4 90 98 74 FF 90 C4    R ONLY......t...
001A90: 00 F0 74 FF 90 C4 01 F0 74 FF 90 C4 02 F0 E5 42    ..t.....t......B
001AA0: 44 3F 90 C4 03 F0 22 E5 1E D3 94 1E 50 07 E5 1E    D?....".....P...
001AB0: C3 94 01 50 07 74 AA 90 C4 00 F0 22 75 1F 00 E5    ...P.t....."u...
001AC0: 1E D3 94 08 40 16 E5 1F 90 C4 00 12 1D 51 74 00    ....@........Qt.
001AD0: F0 05 1F E5 1E C3 94 08 F5 1E 80 E3 E5 1F C3 94    ................
001AE0: 03 50 13 E5 1E 90 1D 48 93 FE E5 1F 90 C4 00 12    .P.....H........
001AF0: 1D 51 EE F0 80 19 E5 1E 90 1D 48 93 54 3F FE E5    .Q........H.T?..
001B00: 42 54 C0 4E FE E5 1F 90 C4 00 12 1D 51 EE F0 05    BT.N........Q...
001B10: 1F E5 1F C3 94 04 50 20 E5 1F 84 03 0C E5 42 54    ......P ......BT
001B20: C0 44 3F 90 C4 03 F0 80 0B E5 1F 90 C4 00 12 1D    .D?.............
001B30: 51 74 FF F0 05 1F 80 D9 22 90 E8 20 E4 F0 75 1F    Qt......" .. ..u.
001B40: 14 75 1E 00 75 1E 1F 75 1F 55 75 1F 14 75 1E 00    .u..u..u.Uu..u..
001B50: 75 1E 1F 75 1F 55 30 92 06 75 1A 08 12 01 68 75    u..u.U0..u....hu
001B60: 1F 01 75 1E 00 AE 1E AF 1F 74 28 BE 00 16 9F 40    ..u......t(....@
001B70: 13 30 92 02 80 14 78 1F 74 01 26 F6 50 04 18 E4    .0....x.t.&.P...
001B80: 36 F6 50 E1 75 1A 0B 12 01 6B 22 BC 00 0F BE 00    6.P.u....k".....
001B90: 08 ED 8F F0 84 FF AD F0 22 E4 FE FF 22 BE 00 0D    ........"..."...
001BA0: EF 60 FE 54 F0 60 6F 20 E7 03 02 1C 41 EA C0 E0    .`.T.`o ....A...
001BB0: EB C0 E0 78 01 7A 00 75 F0 01 EE 20 E7 10 EF 25    ...x.z.u... ...%
001BC0: E0 FF EE 33 FE 0A C5 F0 23 C5 F0 30 E7 F0 EA 54    ...3....#..0...T
001BD0: 07 F9 09 6A 7A 00 7B 00 60 01 08 C3 EC 9E 40 16    ...jz.{.`.....@.
001BE0: 70 04 ED 9F 40 10 ED 9F FD EC 9E FC E5 F0 CA 4A    p...@..........J
001BF0: CA 03 F5 F0 90 05 E5 F0 03 F5 F0 C3 EE 13 FE EF    ................
001C00: 13 FF D9 D7 79 08 CA CB CA DB D0 EA FE EB FF D0    ....y...........
001C10: E0 FB D0 E0 FA 22 EC 8F F0 84 FC ED 54 F0 45 F0    ....."......T.E.
001C20: C4 8F F0 84 FE ED C4 54 F0 45 F0 C4 8F F0 84 FD    .......T.E......
001C30: EE C4 FE 54 F0 2D FF EE 54 0F 3C FE AD F0 7C 00    ...T.-..T.<...|.
001C40: 22 79 00 78 00 8F F0 EC 7E 08 20 E7 0D C3 CD 33    "y.x....~. ....3
001C50: CD 33 C9 33 C9 CB 33 CB DE F0 84 49 F9 E5 F0 8F    .3.3..3....I....
001C60: F0 BE 00 E6 FD 7C 00 E9 FF E8 FE 22 90 00 00 78    .....|....."...x
001C70: 00 79 00 E4 93 28 F8 E9 34 00 F9 A3 74 1F B5 83    .y...(..4...t...
001C80: F2 74 FE B5 82 ED E4 93 69 70 18 74 01 93 68 70    .t......ip.t..hp
001C90: 15 75 A0 E0 78 00 F4 F2 08 70 FA E2 28 84 FF    .u..x....p..(..
001CA0: 0E 08 B8 00 F7 22 C2 B1 12 1C C1 C2 5A 80 FE 12    ....."......Z...
001CB0: 1C C1 A3 84 84 E5 83 B4 FF F8 75 83 20 82 81 80    ..........u. ...
001CC0: F1 78 F8 07 12 01 10 90 C0 06 74 42 F0 22 C0 E0    .x........tB."..
001CD0: C0 F0 C0 83 C0 82 C0 D0 75 D0 08 12 0D 55 D0 D0    ........u....U..
001CE0: D0 82 D0 83 D0 F0 D0 E0 32 C0 E0 C0 F0 C0 83 C0    ........2.......
001CF0: 82 C0 D0 75 D0 10 12 10 44 D0 D0 D0 82 D0 83 D0    ...u....D.......
001D00: F0 D0 E0 32 EE C0 E0 7E 00 12 1B 88 EF FD EE FC    ...2...~........
001D10: D0 E0 FE 22 A3 E0 14 F0 B4 FF 06 12 1D 3E E0 14    ..."........>..
001D20: F0 22 04 80 07 C3 CE 13 CE CF 13 D5 E0 F6 22    ."............."
001D30: F8 8F F0 A4 FF E5 F0 CE 88 F0 A4 2E FE 22 05 82    ............."..
001D40: D5 82 02 15 83 15 82 22 FF FE FC F8 F0 E0 C0 80    ......."........
001D50: 00 25 82 F5 82 50 02 05 83 22 75 81 52 75 D0 00    .%...P..."u.Ru..
001D60: 02 07 91 08 06 B6 00 02 18 06 22 75 81 52 E4 73    .........."u.R.s
001D70: FF FF FF FF FF FF FF FF FF FF FF FF FF FF FF FF    ................
001D80: FF FF FF FF FF FF FF FF FF FF FF FF FF FF FF FF    ................
001D90: FF FF FF FF FF FF FF FF FF FF FF FF FF FF FF FF    ................
001DA0: FF FF FF FF FF FF FF FF FF FF FF FF FF FF FF FF    ................
001DB0: FF FF FF FF FF FF FF FF FF FF FF FF FF FF FF FF    ................
001DC0: FF FF FF FF FF FF FF FF FF FF FF FF FF FF FF FF    ................
001DD0: FF FF FF FF FF FF FF FF FF FF FF FF FF FF FF FF    ................
001DE0: FF FF FF FF FF FF FF FF FF FF FF FF FF FF FF FF    ................
001DF0: FF FF FF FF FF FF FF FF FF FF FF FF FF FF FF FF    ................
001E00: FF FF FF FF FF FF FF FF FF FF FF FF FF FF FF FF    ................
001E10: FF FF FF FF FF FF FF FF FF FF FF FF FF FF FF FF    ................
001E20: FF FF FF FF FF FF FF FF FF FF FF FF FF FF FF FF    ................
001E30: FF FF FF FF FF FF FF FF FF FF FF FF FF FF FF FF    ................
001E40: FF FF FF FF FF FF FF FF FF FF FF FF FF FF FF FF    ................
001E50: FF FF FF FF FF FF FF FF FF FF FF FF FF FF FF FF    ................
001E60: FF FF FF FF FF FF FF FF FF FF FF FF FF FF FF FF    ................
001E70: FF FF FF FF FF FF FF FF FF FF FF FF FF FF FF FF    ................
001E80: FF FF FF FF FF FF FF FF FF FF FF FF FF FF FF FF    ................
```

```
001E90: FF FF FF FF FF FF FF FF FF FF FF FF FF FF FF FF   ................
001EA0: FF FF FF FF FF FF FF FF FF FF FF FF FF FF FF FF   ................
001EB0: FF FF FF FF FF FF FF FF FF FF FF FF FF FF FF FF   ................
001EC0: FF FF FF FF FF FF FF FF FF FF FF FF FF FF FF FF   ................
001ED0: FF FF FF FF FF FF FF FF FF FF FF FF FF FF FF FF   ................
001EE0: FF FF FF FF FF FF FF FF FF FF FF FF FF FF FF FF   ................
001EF0: FF FF FF FF FF FF FF FF FF FF FF FF FF FF FF FF   ................
001F00: FF FF FF FF FF FF FF FF FF FF FF FF FF FF FF FF   ................
001F10: FF FF FF FF FF FF FF FF FF FF FF FF FF FF FF FF   ................
001F20: FF FF FF FF FF FF FF FF FF FF FF FF FF FF FF FF   ................
001F30: FF FF FF FF FF FF FF FF FF FF FF FF FF FF FF FF   ................
001F40: FF FF FF FF FF FF FF FF FF FF FF FF FF FF FF FF   ................
001F50: FF FF FF FF FF FF FF FF FF FF FF FF FF FF FF FF   ................
001F60: FF FF FF FF FF FF FF FF FF FF FF FF FF FF FF FF   ................
001F70: FF FF FF FF FF FF FF FF FF FF FF FF FF FF FF FF   ................
001F80: FF FF FF FF FF FF FF FF FF FF FF FF FF FF FF FF   ................
001F90: FF FF FF FF FF FF FF FF FF FF FF FF FF FF FF FF   ................
001FA0: FF FF FF FF FF FF FF FF FF FF FF FF FF FF FF FF   ................
001FB0: FF FF FF FF FF FF FF FF FF FF FF FF FF FF FF FF   ................
001FC0: FF FF FF FF FF FF FF FF FF FF FF FF FF FF FF FF   ................
001FD0: FF FF FF FF FF FF FF FF FF FF FF FF FF FF FF FF   ................
001FE0: FF FF FF FF FF FF FF FF FF FF FF FF FF FF FF FF   ................
001FF0: FF FF FF FF FF FF FF FF FF FF FF FF FF FF A0 92   ................
```

Appendix C

```
000000: 02 1F 60 C3 EF 9D FF EE 9C FE 22 02 1E D4 A3 E0   ...`......."....
000010: 04 F0 70 06 12 1F 44 E0 04 F0 22 02 1E EF FF FF   ..P...D..."....
000020: 4D 56 53 20 2D 20 58 58 20 20 20 56 20 31 2E 31   MVS - XX   V 1.1
000030: 43 6F 70 79 72 69 67 68 74 20 20 31 39 38 34 20   Copyright  1984
000040: 62 79 20 4D 49 44 20 4C 61 62 73 2C 49 6E 63 2E   by MID Labs,Inc.
000050: 52 65 70 72 6F 64 75 63 74 69 6F 6E 20 20 20 20   Reproduction
000060: 50 72 6F 68 69 62 69 74 65 64 20 20 62 79 20 20   Prohibited  by
000070: 4C 61 77 2E 2A 2A 2A 2A 2A 2A 2A 2A 2A 2A 2A 2A   Law.************
000080: 75 33 01 75 8B 02 75 8D 00 75 A8 00 75 89 10 75   u3.u..u..u..u..u
000090: 88 00 D2 03 E5 18 B4 FF 2A E5 43 44 80 F5 43 E5   ........*.CD..C.
0000A0: 43 90 C4 04 F0 75 19 00 E5 19 D3 94 07 50 13 E5   C....u.......P..
0000B0: 19 90 C0 00 12 1F 57 74 20 F0 78 19 74 01 26 F6   ......Wt .x.t.&.
0000C0: 50 E6 22 E5 43 54 FC F5 43 E5 43 90 C4 04 F0 75   P.".CT..C.C....u
0000D0: 24 02 85 19 32 75 88 40 75 A8 88 22 90 E1 02 50   $...2u.@u.."...P
0000E0: 44 01 90 E1 02 F0 E5 18 60 25 15 18 75 1A 01 75   D.......`%..u..u
0000F0: 19 00 AE 19 AF 1A 74 58 C3 9F 74 02 9E 40 0E 78   ......tX..t..@.x
000100: 1A 74 01 26 F6 50 04 18 E4 36 F6 50 E5 80 D7 22   .t.&.P...6.P..."
000110: E5 43 54 FC F5 43 E5 43 90 C4 04 F0 E5 18 75 F0   .CT..C.C......u.
000120: 08 A4 FF AE F0 8F 18 75 19 00 E5 19 D3 94 07 50   .......u.......P
000130: 1B E5 18 25 19 90 1C 0C 93 FE E5 19 90 C0 00 12   ...%............
000140: 1F 57 EE F0 78 19 74 01 26 F6 50 DE 22 75 18 00   .W..x.t.&.P."u..
000150: E5 18 D3 94 07 50 13 E5 18 90 C0 00 12 1F 57 74   .....P........Wt
000160: 20 F0 78 18 74 01 26 F6 50 E6 22 75 A8 00 E5 43    .x.t.&.P."u...C
000170: 44 80 F5 43 E5 43 90 C4 04 F0 90 F0 01 E4 F0 90   D..C.C..........
000180: F0 03 E4 F0 90 F0 02 E4 F0 D2 97 D2 96 90 E1 03   ................
000190: E0 54 FD 44 08 90 E1 03 F0 90 E1 03 E0 44 10 90   .T.D.........D..
0001A0: E1 03 F0 90 C4 05 E4 F0 90 E1 02 E0 44 01 90 E1   ............D...
0001B0: 02 F0 75 18 07 12 01 10 E5 1A 75 F0 0A B4 AF F0   ..u.......u.....
0001C0: 7E 00 EF 24 30 90 C0 07 F0 E5 1A 75 F0 0A 84 FF   ~..$0......u....
0001D0: 7E 00 EF 24 30 90 C0 06 F0 80 FE 90 E1 01 E0 54   ~..$0...........T
0001E0: 02 70 2D 90 E0 07 E0 14 F0 90 C4 05 E4 F0 90 C4   .p-.............
0001F0: 05 E4 F0 90 E1 01 E0 54 02 70 06 75 1A 0D 12 01   .......T.p.u....
000200: 6B 90 E0 07 E0 C3 94 F0 50 06 75 1A 0F 12 01 6B   k.......P.u....k
000210: 22 75 1C 01 75 1B 00 AE 1B AF 1C 74 2B BE 00 15   "u..u......t+...
000220: 9F 40 12 30 92 01 22 78 1C 74 01 26 F6 50 04 1B   .@.0.."x.t.&.P..
000230: E4 36 F6 50 E2 75 1A 0B 12 01 6B 22 75 89 01 75   .6.P.u....k"u..u
000240: 8A 02 75 8C F1 75 A8 82 75 B8 02 22 E5 36 C3 94   ..u..u..u.."6..
000250: 0A 50 01 22 75 36 00 30 93 06 E5 22 64 03 60 0E   .P."u6.0..."d.`.
000260: E5 22 C3 94 02 40 07 E5 22 D3 94 03 40 17 E5 31   ."...@.."...@..1
000270: FF 7E 00 0F BF 00 01 0E 74 1D 12 1F 36 0E 8E 1E   .~......t...6...
000280: 12 1C AD 80 03 12 1C 92 22 E5 2D D3 94 01 40 53   ........".-...@S
000290: E5 2C D3 94 28 50 07 E5 2D D3 94 73 50 2D E5 2C   .,..(P..-..sP-.,
0002A0: D3 94 10 50 07 E5 2D D3 94 37 50 07 A2 94 B3 92   ...P..-..7P.....
0002B0: 97 80 16 D2 97 74 0A F5 1B 12 00 DC E5 2D D3 94   .....t.......-..
0002C0: 37 40 06 75 1A 06 12 01 6B 80 16 D2 97 74 0A F5   7@.u....k....t..
0002D0: 18 12 00 DC E5 2D D3 94 73 40 06 75 1A 06 12 01   .....-..s@.u....
```

```
0002E0: 6B 80 20 D2 97 74 0A F5 18 12 00 DC E5 2D C3 94
0002F0: 02 50 10 90 E1 03 E0 44 20 90 E1 03 F0 75 1A 02
000300: 12 01 6B 22 30 94 03 02 03 AA 90 CC 00 E0 F4 54
000310: 0F F5 25 90 CC 00 E0 F4 54 0F 65 25 60 03 75 25
000320: 00 E5 25 84 01 0C 12 16 E9 E5 22 D3 94 01 40 02
000330: 80 79 E5 25 64 09 60 05 E5 25 84 0C 18 90 C4 06
000340: E4 F0 90 C4 06 E4 F0 90 C4 06 E4 F0 90 E1 01 E0
000350: 54 02 60 01 22 E5 25 70 19 E5 22 70 05 A2 93 83
000360: 40 02 80 02 80 48 E5 22 84 01 03 20 93 02 80 02
000370: 80 3F E5 22 C3 94 06 50 2F E5 25 54 0F F5 25 E5
000380: 25 60 23 E5 22 90 0E 98 F8 28 28 73 80 23 80 21
000390: 80 1F E5 25 64 02 60 02 80 17 80 0A 80 13 E5 25
0003A0: 64 0C 60 02 80 0B 80 02 80 0D 22 90 07 98 12 1F
0003B0: 71 90 07 F8 12 1F 71 90 0E 67 12 1F 71 30 01 01
0003C0: 22 90 CC 00 E0 54 20 60 06 75 18 06 12 00 80 12
0003D0: 03 04 90 E1 03 E0 44 02 90 E1 03 F0 90 CC 00 E0
0003E0: FE 90 CC 00 E0 4E 54 20 60 0C 90 E1 03 E0 44 04
0003F0: 90 E1 03 F0 90 D9 90 E1 03 E0 54 FD 90 E1 03 F0
000400: 74 0A F5 18 12 00 DC 90 CC 00 E0 FE 90 CC 00 E0
000410: 4E 54 20 60 02 80 B8 90 E1 03 E0 54 FB 90 E1 03
000420: F0 75 18 FF 12 00 80 90 CC 00 E0 54 40 60 0D 75
000430: 18 01 12 00 80 74 82 F5 46 12 17 3C 12 18 C6 22
000440: 90 CC 00 E0 54 20 60 10 90 CC 00 E0 54 20 60 08
000450: 90 CC 00 E0 54 20 70 02 80 26 E5 22 D3 94 01 40
000460: 0A 20 94 05 12 16 E9 80 35 80 13 90 E1 03 E0 54
000470: 04 FF 7E 00 EF 60 01 22 20 94 03 12 16 E9 80 1D
000480: 90 E1 03 E0 54 04 FF 7E 00 EF 60 11 74 0A F5 18
000490: 12 00 DC 90 E1 03 E0 54 FB 90 E1 03 F0 22 90 07
0004A0: 98 12 1F 71 90 CC 00 E0 54 80 60 08 90 E0 02 E0
0004B0: 04 F0 80 05 90 E0 02 E4 F0 90 CC 00 E0 54 40 60
0004C0: 08 90 E0 00 12 00 0E 80 07 90 E0 00 E4 F0 A3 F0
0004D0: 90 E0 00 E0 FE A3 E0 FF EF D3 94 B6 EE 94 03 40
0004E0: 2C 90 E0 00 E4 F0 A3 F0 75 A8 00 75 88 00 90 E1
0004F0: 02 E0 44 01 90 E1 02 F0 75 18 01 12 00 80 74 82
000500: F5 46 12 17 3C 75 A8 00 75 88 00 D3 22 90 E0 02
000510: E0 D3 94 64 40 2A 90 E0 02 E4 F0 75 A8 00 75 88
000520: 00 90 E1 02 E0 44 01 90 E1 02 F0 75 18 04 12 00
000530: 80 74 C8 F5 46 12 17 3C 75 A8 00 75 88 00 D3 22
000540: C3 22 12 1A F4 30 00 01 22 E5 35 C3 94 32 50 01
000550: 22 75 35 00 E5 43 44 01 F5 43 E5 2C 75 F0 04 84
000560: FF 7E 00 8F 18 E5 43 90 C4 04 F0 74 20 90 C0 03
000570: F0 74 30 90 C0 02 F0 74 20 90 C0 04 F0 EF 75 F0
000580: 0A 84 AD F0 7C 00 ED 24 30 90 C0 01 F0 E5 18 75
000590: F0 0A 84 FF 7E 00 8F 18 E5 18 70 08 74 20 90 C0
0005A0: 00 F0 80 08 E5 18 24 30 90 C0 00 F0 20 94 05 75
0005B0: 18 00 80 14 E5 2C 24 0F C3 95 2D 40 05 85 2D 18
0005C0: 80 06 E5 2C 24 0F F5 18 E5 18 C3 94 0F 50 05 75
0005D0: 18 00 80 07 E5 18 C3 94 0F F5 18 E5 18 04 75 F0
0005E0: 02 84 FF 7E 00 8F 18 EF 54 01 70 08 74 30 90 C0
0005F0: 07 F0 80 08 74 35 90 C0 07 F0 15 18 E5 18 75 F0
000600: 02 84 FF 7E 00 8F 18 EF 75 F0 0A 84 AD F0 7C 00
000610: ED 24 30 90 C0 06 F0 E5 18 75 F0 0A 84 FF 7E 00
000620: 8F 18 E5 18 70 08 74 20 90 C0 05 F0 80 08 E5 18
000630: 24 30 90 C0 05 F0 22 75 1D 01 E5 1D D3 94 AA 50
000640: 49 74 01 F5 18 12 00 DC 90 E8 00 E4 F0 12 02 11
000650: 90 E8 00 E0 C3 94 02 50 1E 74 0A F5 18 12 00 DC
000660: 90 E8 00 E4 F0 12 02 11 90 E8 00 E0 C3 94 02 50
000670: 06 75 1A 02 12 01 6B 90 E8 00 E0 C3 94 19 50 02
000680: 80 0E 78 1D 74 01 26 F6 50 B0 75 1A 03 12 01 6B
000690: 74 0A F5 18 12 00 DC 22 75 1B 00 90 CC 00 E0 54
0006A0: 0F 64 0F 60 05 75 1B 00 80 02 05 1B 90 CC 00 E0
0006B0: F4 54 0F B4 0C 05 E5 22 B4 05 02 80 03 12 03 04
0006C0: 74 01 F5 18 12 00 DC E5 1B C3 94 12 50 02 80 CB
0006D0: 22 C2 0A C2 B1 A2 B0 50 02 80 13 A2 B0 50 02 80
0006E0: 0D A2 B0 50 02 80 07 75 18 FF 12 00 80 22 12 03
0006F0: 04 30 0A 02 80 DD D2 0A 75 18 00 12 00 80 80 D3
000700: E5 38 C3 94 FA 50 02 05 38 90 E1 01 E0 54 01 70
000710: 0F 90 E1 01 E0 54 01 70 07 E5 38 D3 94 F5 50 02
000720: 80 02 D2 09 90 E1 01 E0 54 01 60 11 30 94 0E 30
000730: 09 08 90 E1 01 E0 54 01 60 03 20 94 02 80 05 C2
000740: 09 75 38 00 E5 38 C3 94 3F 50 0C 90 E1 02 E0 54
```

```
000750: FE 90 E1 02 F0 80 0A 90 E1 02 E0 44 01 90 E1 02
000760: F0 22 85 1C 18 12 01 10 12 06 98 75 1D 01 E5 1D
000770: D3 94 10 50 12 74 0A F5 18 12 00 DC 12 03 04 78
000780: 1D 74 01 26 F6 50 E7 22 12 1E 72 12 1D 3F 12 15
000790: B9 75 22 04 D2 07 80 00 75 A8 00 12 15 38 90 E1
0007A0: 03 E0 54 04 FF 7E 00 EF 60 02 C2 01 E5 22 C3 94
0007B0: 06 50 42 E5 22 90 1C 8C 93 F5 43 E5 43 90 C4 04
0007C0: F0 75 42 3F E5 22 64 04 60 05 E5 22 B4 05 03 75
0007D0: 42 BF E5 42 90 C4 03 F0 E5 22 90 0E AA F8 28 28
0007E0: 73 02 08 6D 02 09 49 02 0A 3B 02 08 41 02 0C 58
0007F0: 02 0C 59 80 03 02 0E 67 75 A8 00 75 98 00 E5 25
000800: 70 0D 30 93 05 75 22 00 80 03 75 22 01 80 3F E5
000810: 25 B4 08 0F E5 22 64 04 60 04 D2 07 80 02 B2 07
000820: 75 22 04 E5 25 B4 02 03 75 22 03 E5 25 B4 0C 03
000830: 75 22 05 E5 25 B4 04 15 E5 22 64 02 60 05 75 22
000840: 02 80 0B 30 93 05 75 22 00 80 03 75 22 01 E5 22
000850: C3 94 04 50 15 90 C4 05 E4 F0 90 E1 01 E0 54 02
000860: 70 08 90 C4 05 E4 F0 12 01 DB 02 07 98 75 A8 00
000870: 75 88 00 E5 25 60 07 74 00 F5 1C 12 07 62 75 18
000880: 0B 12 01 10 12 02 3C 75 2A 3E 75 2B 00 75 23 00
000890: 75 88 10 90 F0 03 E4 F0 90 E1 03 E0 44 08 90 E1
0008A0: 03 F0 12 03 04 12 04 40 12 1A F4 AE 2A AF 2B 7C
0008B0: 27 7D 00 12 00 03 7F 01 7A DC EE BF 06 8A 07 12
0008C0: 1F 36 8E 31 12 02 4C 90 E8 03 E4 F0 12 02 11 90
0008D0: E8 00 E0 F4 75 F0 96 A4 FF AE F0 EE F4 04 24 C7
0008E0: F5 45 75 44 00 20 94 0B 75 23 01 75 27 00 75 26
0008F0: 00 80 3E AE 44 AF 45 74 80 12 1F 36 7C 72 7D 00
000900: 8E 07 12 1F 0A 74 01 8C 06 8D 07 12 1F 28 8E 26
000910: 8F 27 AE 44 AF 45 74 7F 12 1F 36 7C 72 7D 00 8E
000920: 07 12 1F 0A 74 01 8C 06 8D 07 12 1F 28 8E 28 8F
000930: 29 90 E0 07 E0 C3 94 80 50 09 90 E0 07 E0 F5 1A
000940: 12 01 6B 12 01 DB 02 08 93 75 A8 00 75 88 00 E5
000950: 25 60 07 74 00 F5 1C 12 07 62 75 18 0C 12 01 10
000960: 12 02 3C 75 23 03 90 E0 10 E4 F0 A3 F0 75 88 10
000970: 90 F0 03 E4 F0 90 E1 03 E0 44 08 90 E1 03 F0 12
000980: 03 04 12 04 40 12 1A F4 90 E8 03 E4 F0 12 02 11
000990: 90 E8 00 E0 F4 F5 39 85 39 31 12 02 4C 30 94 41
0009A0: 90 E0 10 E4 F0 A3 F0 E5 39 75 F0 89 A4 FF AE F0
0009B0: 74 FF 8E 04 8F 05 FF 12 1F 0A 74 27 2D FD 50 01
0009C0: 0C 8C 44 8D 45 ED D3 94 B0 EC 94 00 40 06 75 44
0009D0: 00 75 45 B0 90 F0 01 E4 F0 E5 45 90 F0 02 F0 80
0009E0: 42 E5 39 D3 94 1E 40 08 90 E0 10 12 00 0E 80 12
0009F0: 90 E0 10 E0 FE A3 E0 FF EF 4E 60 06 90 E0 10 12
000A00: 1F 1A 90 E0 10 E0 FE A3 E0 FF EF D3 94 D0 EE 94
000A10: 07 40 06 75 1A 10 12 01 6B 90 F0 02 E4 F0 90 F0
000A20: 01 E4 F0 90 E0 07 E0 C3 94 80 50 09 90 E0 07 E0
000A30: F5 1A 12 01 6B 12 01 D9 02 09 70 75 A8 00 75 88
000A40: 00 E5 25 B4 04 07 74 01 F5 1C 12 07 62 12 06 D1
000A50: 12 03 BD 75 A8 00 75 88 00 90 E1 03 E0 54 DF 90
000A60: E1 03 F0 90 E8 04 E4 F0 12 02 11 90 E8 00 E0 75
000A70: F0 F1 A4 FF AE F0 8E 2C E5 43 44 01 F5 43 E5 43
000A80: 90 C4 04 F0 75 3B 01 12 06 37 75 35 2D 12 02 3C
000A90: 75 23 02 75 88 10 90 E0 00 E4 F0 A3 F0 90 E0 02
000AA0: E4 F0 12 04 A4 50 02 80 DB 30 94 1E 90 E1 03 E0
000AB0: 44 10 90 E1 03 F0 AE 40 AF 41 74 E9 D3 9F 74 FD
000AC0: 9E 40 05 78 40 12 1F 69 80 30 AE 40 AF 41 74 2C
000AD0: D3 9F 74 01 9E 40 08 75 41 00 75 40 00 80 1B 75
000AE0: 41 00 75 40 00 75 A8 00 75 88 00 90 E1 02 E0 44
000AF0: 01 90 E1 02 F0 12 19 F2 80 8A 30 94 08 90 E1 01
000B00: E0 54 01 70 02 80 0C 90 E1 02 E0 54 FE 90 E1 02
000B10: F0 80 0A 90 E1 02 E0 44 01 90 E1 02 F0 12 03 04
000B20: 12 04 40 12 02 89 12 05 42 90 E0 07 E0 C3 94 80
000B30: 50 09 90 E0 07 E0 F5 1A 12 01 6B 12 01 D9 02 0A
000B40: A2 75 A8 00 75 88 00 E5 25 B4 02 07 74 0E F5 1C
000B50: 12 07 62 12 03 BD 75 A8 00 75 88 00 90 E1 03 E0
000B60: 54 DF 90 E1 03 F0 90 E8 04 E4 F0 12 02 11 90 E8
000B70: 00 E0 75 F0 F1 A4 FF AE F0 8E 2C 75 31 00 E5 43
000B80: 44 01 F5 43 E5 43 90 C4 04 F0 75 3B 01 12 06 37
000B90: 75 35 2D 75 89 11 75 8A 02 75 9C B0 75 B8 08 75
000BA0: 88 02 75 8D D0 75 24 01 75 30 FF 75 23 02 75 A8
000BB0: 8A 75 88 50 75 2F 02 75 2E 00 90 E0 00 E4 F0 A3
```

```
000BC0: F0 90 E0 02 E4 F0 30 94 1E 90 E1 03 E0 44 10 90    .......0.....D..
000BD0: E1 03 F0 AE 40 AF 41 74 E8 D3 9F 74 FD 9E 40 05    ....@.At...t..@.
000BE0: 78 40 12 1F 69 80 42 75 30 FF AE 40 AF 41 74 2C    x@..i.Bu0..@.At,
000BF0: D3 9F 74 01 9E 40 12 75 41 00 75 40 00 90 E1 03    ..t..@.uA.u@....
000C00: E0 54 EF 90 E1 03 F0 80 20 75 41 00 75 40 00 75    .T...... uA.u@.u
000C10: A8 00 75 88 00 D2 96 90 F0 01 54 F0 90 F0 03 E4    ..u.......T.....
000C20: F0 D2 97 12 19 F2 02 0B 8A 12 03 04 12 04 A4 50    ...............P
000C30: 03 02 0B 8A 12 04 40 12 02 89 12 05 42 12 02 4C    ......@.....B..L
000C40: 90 E0 07 E0 C3 94 80 50 09 90 E0 07 E0 F5 1A 12    .......P........
000C50: 01 6B 12 01 DB 02 0B C6 75 A8 00 75 88 00 E5 22    .k......u..u..."
000C60: B4 05 16 E5 25 64 01 60 07 74 0A F5 1C 12 07 62    ....%d.`.t.....b
000C70: C2 07 12 06 D1 D2 B1 80 18 E5 25 B4 08 13 30 07    ..........%...0.
000C80: 09 74 0F F5 1C 12 07 62 80 07 74 0D F5 1C 12 07    .t.....b..t.....
000C90: 62 12 03 BD 75 A8 00 75 88 00 90 E1 03 E0 54 DF    b...u..u......T.
000CA0: 90 E1 03 F0 75 2C F0 75 31 00 75 3A 00 E5 43 44    ....u,.u1.u:..CD
000CB0: 01 F5 43 E5 43 90 C4 04 F0 30 07 06 75 18 0F 12    ..C.C....0..u...
000CC0: 01 10 C2 09 75 38 FF 12 06 37 75 35 2D 75 89 11    ....u8...7u5-u..
000CD0: 75 8A 02 75 8C B0 75 88 08 75 8B 02 75 8D D0 75    u..u..u..u..u..u
000CE0: 23 04 75 30 00 75 24 06 75 A8 8A 90 E0 00 E4 F0    #.u0.u$.u.......
000CF0: A3 F0 90 E0 02 E4 F0 75 44 00 C2 04 75 3B 01 C2    .......uD..u;..
000D00: 08 75 3E 00 75 39 00 75 3A 64 C2 06 D2 97 75 88    .u>.u9.u:d....u.
000D10: 50 30 07 37 E5 43 44 80 F5 43 E5 43 90 C4 04 F0    P0.7.CD..C.C....
000D20: 90 E1 02 E0 44 01 90 E1 02 F0 D2 97 A2 94 72 94    ....D.........r.
000D30: 50 0C 90 E1 03 E0 44 10 90 E1 03 F0 80 0A 90 E1    P.....D.........
000D40: 03 E0 54 EF 90 E1 03 F0 02 0D E1 30 94 1C 90 E0    ..T........0....
000D50: 20 74 17 F0 A3 74 70 F0 75 41 00 75 40 00 90 E1     t...tp.uA.u@...
000D60: 03 E0 44 10 90 E1 03 F0 80 77 90 E1 02 E0 44 01    ..D......w....D.
000D70: 90 E1 02 F0 A2 97 40 06 90 E0 20 12 1F 1A 90 E0    ......@... .....
000D80: 20 E0 FE A3 E0 FF EF 4E 70 06 75 1A 04 12 01 6B     ......Np.u....k
000D90: E5 2D C3 94 13 50 07 A2 97 B3 72 06 40 02 80 25    .-...P....r.@..%
000DA0: 75 A8 00 75 88 00 A2 05 40 06 E5 43 44 80 F5 43    u..u....@..CD..C
000DB0: E5 43 90 C4 04 F0 74 14 F5 18 12 00 DC D2 97 12    .C....t.........
000DC0: 19 F2 02 0C B9 78 40 12 1F 69 AE 40 AF 41 EF D3    .....x@..i.@.A..
000DD0: 94 D0 EE 94 07 40 0A 90 E1 03 E0 54 EF 90 E1 03    .....@.....T....
000DE0: F0 12 03 04 12 04 A4 50 03 02 0C B9 12 04 40 20    .......P......@ 
000DF0: 07 40 12 05 42 90 E1 03 E0 54 01 FF 7E 00 EF 70    .@..B....T..~..p
000E00: 04 E5 35 60 02 80 06 74 8B 90 C0 04 F0 E5 2D C3    ..5`...t......-.
000E10: 94 02 50 07 74 0A F5 19 12 00 DC E5 2D C3 94 02    ..P.t.......-...
000E20: 50 10 90 E1 03 E0 44 20 90 E1 03 F0 75 1A 02 12    P.....D ....u...
000E30: 01 6B 12 02 4C E5 22 B4 05 05 A2 07 B3 40 02 80    .k..L."......@..
000E40: 03 12 07 00 90 E0 07 E0 C3 94 80 50 09 90 E0 07    ...........P....
000E50: E0 F5 1A 12 01 6B 90 E1 01 E0 54 02 60 06 75 1A    .....k....T.`.u.
000E60: 0E 12 01 6B 02 0D 11 74 FF 90 E1 03 F0 90 F0 03    ...k...t........
000E70: E4 F0 90 F0 02 E4 F0 75 43 80 D2 97 D2 96 90 E1    .......uC.......
000E80: 02 E0 44 01 90 E1 02 F0 75 18 07 12 01 10 74 41    ..D.....u.....tA
000E90: 90 C0 06 F0 C2 90 80 FE 02 03 8C 02 03 8E 02 03    ................
000EA0: 90 02 03 92 02 03 9C 02 03 9E 02 03 E1 02 07 E4    ................
000EB0: 02 07 E7 02 07 EA 02 07 ED 02 07 F0 75 4C 1E 75    ............uL.u
000EC0: 4B 00 75 4B 02 75 4C 58 75 4C 44 75 4B 00 75 4C    K.uK.uLXuLDuK.uL
000ED0: 37 75 4B 00 30 92 06 E5 22 64 02 60 02 80 26 90    7uK.0..."d.`..&.
000EE0: E8 00 E4 F0 75 4C 28 75 4B 00 75 4B 03 75 4C 21    ....uL(uK.uK.uL!
000EF0: 75 4C 29 75 4B 00 75 4B 01 75 4C 93 30 92 06 74    uL)uK.uK.uL.0..t
000F00: 0B 90 E0 07 F0 75 4C 01 75 4B 00 AE 4B AF 4C 74    .....uL.uK..K.Lt
000F10: 28 BE 00 15 9F 40 12 30 92 01 22 78 4C 74 01 26    (....@.0.."xLt.&
000F20: F6 50 04 18 E4 36 F6 50 E2 74 0B 90 E0 07 F0 22    .P...6.P.t....."
000F30: 75 8C DB 75 8A FF 05 35 05 34 E5 3B 85 52    u..u...5.6.4.;.R
000F40: 05 A2 05 B3 40 02 80 0C E5 43 44 80 F5 43 E5 43    ....@....CD..C.C
000F50: 90 C4 04 F0 E5 39 60 02 15 3B E5 3B 70 07 E5 22    .....9`..;.;p.."
000F60: D3 94 01 50 02 80 3D A2 94 B3 40 07 E5 2D C3 94    ...P..=...@..-..
000F70: 14 50 05 75 52 00 80 2C 74 AF C3 95 2D 75 F0 8C    .P.uR..,t...-u..
000F80: A4 FF AE F0 EE 24 0F F5 52 F5 3B E5 2D D3 94 AF    .....$..R.;.-...
000F90: 40 06 74 0C F5 52 F5 3B E5 43 54 7F F5 43 E5 43    @.t..R.;.CT..C.C
000FA0: 90 C4 04 F0 E5 38 C3 94 FA 50 02 05 38 E5 23 D3    .....8...P..8.#.
000FB0: 94 04 40 03 02 11 F3 E5 23 90 15 14 F8 28 28 73    ..@.....#....((s
000FC0: 80 0B 80 3F 02 10 71 02 11 DB 02 10 9B AE 26 AF    ...?..q.......&.
000FD0: 27 EF D3 94 08 EE 94 07 40 03 02 11 F3 AE 2A AF    '.......@.....*.
000FE0: 2B AC 26 AD 27 EF 2D FD EE 3C FC 8C 2A 8D 2B ED    +.&.'.-..<..*.+.
000FF0: D3 94 00 EC 94 B0 40 09 75 2A B0 75 2B 00 75 23    ......@.u*.u+.u#
001000: 01 80 33 AE 2B AF 29 EF D3 94 08 EE 94 07 40 03    ..3.+.).......@.
001010: 02 11 F3 AE 2A AF 2B AC 28 AD 29 12 00 03 8E 2A    ....*.+.(.)....*
001020: 8F 2B 74 00 D3 9F 74 3E 9E 40 09 75 2A 3E 75 2B    .+t...t>.@.u*>u+
001030: 00 75 23 00 80 00 E5 22 60 03 02 11 F3 90 F0 03    .u#...."`.......
```

```
001040: E4 F0 90 E1 03 E0 44 C8 90 E1 03 F0 30 94 11 E5
001050: 29 C4 54 0F 90 F0 01 F0 E5 2A 90 F0 02 F0 80 10
001060: 75 2A 27 75 29 00 90 F0 01 E4 F0 90 F0 02 E4 F0
001070: 22 E5 22 64 02 60 05 E5 22 B4 03 02 80 03 02 11
001080: F3 90 E8 04 E4 F0 12 0E BC 90 E8 00 E0 75 F0 A1
001090: A4 FF AE F0 EE 54 FC F5 2C 80 3A E5 22 64 04 60
0010A0: 05 E5 22 B4 05 02 80 03 02 11 F3 90 E8 04 E4 F0
0010B0: 12 0E BC 90 E8 00 E0 75 F0 05 84 FF 7E 00 EF 24
0010C0: 33 F5 3A 90 E8 00 E0 75 F0 DD A4 FF AE F0 EE 54
0010D0: FC F5 2C 80 00 90 E8 03 E4 F0 12 0E BC 90 E8 00
0010E0: E0 F4 F5 39 90 E8 05 E4 F0 E5 22 64 04 60 05 E5
0010F0: 22 B4 05 02 80 2F E5 39 D3 94 1B 40 09 E5 39 C3
001100: 94 1C F5 39 80 03 75 39 00 E5 39 75 F0 12 A4 FF
001110: AE F0 74 04 12 1F 28 EF 85 2C F0 A4 FF AE F0 8E
001120: 4D 8F 4E 80 2D E5 39 D3 94 39 40 09 E5 39 C3 94
001130: 3A F5 4F 80 03 75 4F 00 E5 4F 75 F0 53 A4 FF AE
001140: F0 74 06 12 1F 28 EF 85 2C F0 A4 FF AE F0 8E 4D
001150: 8F 4E 12 0E BC 90 E8 00 E0 F5 4F 90 E8 00 E4 F0
001160: 12 0E BC 90 E8 00 E0 F5 2D E5 22 C3 94 02 40 07
001170: E5 22 D3 94 05 40 02 80 7A 30 94 1B E5 2D D3 94
001180: 01 40 14 E5 4E 45 4D 60 0E E5 22 64 04 60 05 E5
001190: 22 B4 05 05 30 07 02 80 13 E5 4E 54 0F 90 F0 F0
0011A0: 01 F0 E5 4D 24 0F 90 F0 03 F0 80 0A 90 F0 01 E4
0011B0: F0 90 F0 03 E4 F0 90 E8 05 E4 F0 12 0E BC 90 E8
0011C0: 00 E0 C3 95 4F C3 94 03 40 0D 90 E8 00 E0 F4 04
0011D0: 25 4F C3 94 03 50 03 85 4F 31 22 E5 22 64 01 60
0011E0: 02 80 10 90 F0 03 E4 F0 90 E1 03 E0 44 C8 90 E1
0011F0: 03 F0 22 90 0E 67 12 1F 71 75 51 00 E5 51 D3 94
001200: 07 50 1B E5 50 90 1B 84 93 FE E5 51 90 C0 00 12
001210: 1F 57 EE F0 05 50 7B 51 74 01 26 F6 50 DE 22 E5
001220: 24 90 15 23 F8 28 28 73 80 11 02 12 E2 02 14 5F
001230: 02 14 A1 02 14 FA 80 6C 02 13 15 75 8B 02 75 8D
001240: CA E5 31 D3 94 F5 40 05 75 8D CF 80 22 E5 31 D3
001250: 94 E5 40 05 75 8D CE 80 16 E5 31 D3 94 D0 40 05
001260: 75 8D CC 80 0A E5 31 D3 94 B4 40 03 75 8D C8 E5
001270: 22 64 03 60 03 02 15 0E C2 96 75 24 01 7E A6 7F
001280: 38 E5 31 75 F0 02 84 FD 7C 00 ED 24 0C 8E 14 8F
001290: 15 FF 12 1F 0A 74 FF 62 14 62 15 8C 2E 8D 2F E5
0012A0: 2E F5 30 22 75 88 02 75 8D 70 E5 22 64 04 60 05
0012B0: E5 22 B4 05 02 90 03 02 15 0E D2 06 A2 94 83 92
0012C0: 97 75 24 06 7E C2 7F 10 E5 31 75 F0 08 84 FD 7C
0012D0: 00 ED 24 0F 8E 14 9F 15 FF 12 1F 0A 74 FF 62 14
0012E0: 62 15 8C 2E 8D 2F E5 2E F5 30 22 D2 96 E5 22 64
0012F0: 03 60 03 02 15 0E A2 93 82 94 40 01 22 05 30 E5
001300: 30 60 07 75 8B 02 75 8D 00 22 75 24 00 75 8B 02
001310: E5 2F F5 8D 22 E5 22 64 04 60 05 E5 22 B4 05 02
001320: 80 03 02 15 0E 30 07 03 D2 97 22 75 8D DB 75 8B
001330: FF E5 2D C3 94 2F 50 02 C2 0C E5 3E C3 94 03 50
001340: 07 E5 39 C3 94 28 50 02 80 16 C2 0C 90 E1 03 E0
001350: 44 C1 90 E1 03 F0 75 3C 04 75 3E 03 C2 97 D2 08
001360: E5 39 C3 94 37 40 17 20 0C 02 C2 97 90 E1 03 E0
001370: 44 C1 90 E1 03 F0 75 3D 28 75 3E 04 D2 06 E5 3E
001380: B4 04 07 E5 2D D3 94 3F 50 02 80 02 D2 0C E5 39
001390: D3 94 1E 50 07 E5 3E C3 94 04 40 02 80 0B D2 97
0013A0: 75 3E 01 E5 3C 60 02 15 3C E5 3E B4 01 06 E5 22
0013B0: 64 04 60 02 80 1E E5 3C 70 0E 90 E1 01 E0 FE 90
0013C0: E1 01 E0 5E 54 01 70 02 80 0A 90 E1 03 E0 54 3E
0013D0: 90 E1 03 F0 E5 3E B4 04 07 E5 39 D3 94 1E 40 02
0013E0: 80 1C E5 2D C3 94 13 50 07 D2 97 75 3E 03 80 0E
0013F0: C2 97 15 3D E5 3D 70 06 74 07 90 E0 07 F0 30 94
001400: 08 E5 3E B4 04 03 20 0C 07 75 8B 02 75 8D 2C 22
001410: E5 30 04 75 F0 33 84 AF F0 7E 00 8F 30 E5 31 75
001420: F0 B1 A4 FD AC F0 EC 75 F0 04 84 FD 7C 00 ED 24
001430: 02 F5 3F E5 3F D3 94 2D 50 07 E5 31 D3 94 FA 40
001440: 03 75 3F 33 E5 30 70 06 C2 97 D2 08 80 10 30 08
001450: 07 E5 30 C3 95 3F 50 02 80 04 C2 09 D2 97 22 15
001460: 33 E5 33 70 3B E5 32 C3 94 05 50 04 E5 32 70 0E
001470: 30 03 06 E5 32 64 05 60 05 E5 32 B4 07 0E C2 03
001480: E5 43 54 7F F5 43 E5 43 90 C4 04 F0 E5 32 75 F0
001490: 10 A4 FF AE F0 9F 50 12 11 F9 75 33 0A 75 24 03
0014A0: 22 15 33 E5 32 B4 01 2A E5 33 C3 94 06 50 07 E5
```

```
0014B0: 33 D3 94 04 50 02 80 0E E5 43 44 80 F5 43 E5 43    3...P....CD..C.C
0014C0: 90 C4 04 F0 80 0C E5 43 54 7F F5 43 E5 43 90 C4    .......CT..C.C..
0014D0: 04 F0 E5 33 70 23 E5 43 44 80 F5 43 E5 43 90 C4    ...3p#.CD..C.C..
0014E0: 04 F0 E5 32 75 F0 10 A4 FF AE F0 EF 24 08 F5 50    ...2u.......$..P
0014F0: 12 11 F9 75 33 0A 75 24 04 22 15 33 E5 33 70 0D    ...u3.u$.".3.3p.
001500: 74 80 F5 50 12 11 F9 75 33 04 75 24 02 22 90 0E    t..P...u3.u$."..
001510: 67 12 1F 71 02 0F C0 02 0F C2 02 0F C4 02 0F C7    g..q............
001520: 02 0F CA 02 12 28 02 12 2A 02 12 2D 02 12 30 02    .....(..*..-..0.
001530: 12 33 02 12 36 02 12 38 75 A8 00 75 88 00 75 B8    .3..6..8u..u..u.
001540: 00 75 89 00 74 5F 90 74 E1 02 F0 90 01 E4 F0 90    .u..t_.t........
001550: F0 02 E4 F0 90 F0 03 E4 F0 D2 96 90 E1 02 E0 44    ...............D
001560: 01 90 E1 02 F0 74 FF 90 E0 07 F0 75 27 00 75 26    .....t.....u'.u&
001570: 00 75 29 00 75 28 00 75 2B 00 75 2A 00 C2 00 75    .u).u(.u+.u*...u
001580: 34 00 90 E1 03 E0 54 CF 44 08 90 E1 03 F0 12 1C    4.....T.D.......
001590: 92 90 CC 00 E0 54 10 60 0F 75 18 03 12 00 80 75    .....T.`.u.....u
0015A0: 18 FA 12 00 DC 75 A8 00 12 01 4D 90 E0 02 E4 F0    .....u....M.....
0015B0: 75 41 00 75 40 00 C2 04 22 75 43 80 E5 43 90 C4    uA.u@..."uC..C..
0015C0: 04 F0 74 4E 90 E1 00 F0 74 AF 90 E1 02 F0 74 FF    ..tN....t.....t.
0015D0: 90 E1 03 F0 D2 97 D2 96 90 F0 01 E4 F0 90 F0 02    ................
0015E0: E4 F0 90 F0 03 E4 F0 90 E1 03 E0 54 DF 90 E1 03    ...........T....
0015F0: F0 75 37 00 C2 01 C2 02 75 18 28 12 00 DC 75 42    .u7.....u.(...uB
001600: 00 12 1C 92 90 E8 00 E4 F0 12 02 11 90 CC 00 E0    ................
001610: 54 10 60 06 75 18 03 12 00 80 90 CC 00 E0 54 10    T.`.u.........T.
001620: 60 0A 90 CC 00 E0 54 0F 64 0F 60 02 80 02 80 EA    `.....T.d.`.....
001630: 75 18 0A 12 00 DC C2 0B 30 94 08 75 18 07 12 00    u.......0..u....
001640: 80 D2 0B 75 48 00 75 47 01 75 46 00 AE 46 AF 47    ...uH.uG.uF..F.G
001650: 74 20 C3 9F 74 03 9E 40 27 30 94 05 75 48 00 80    t ..t..@'0..uH..
001660: 02 05 48 75 18 01 12 00 DC E5 48 D3 94 14 40 02    ..Hu......H...@.
001670: 80 14 78 47 74 01 26 F6 50 04 18 E4 36 F6 50 CC    ..xGt.&.P...6.P.
001680: 75 1A 11 12 01 6B 75 88 00 75 88 00 E5 43 44 80    u....ku..u...CD.
001690: F5 43 E5 43 90 C4 04 F0 30 08 0C 75 18 08 12 01    .C.C....0..u....
0016A0: 10 75 18 64 12 00 DC 90 E8 00 E0 D3 94 13 50 09    .u.d..........P.
0016B0: 90 E8 00 E0 C3 94 0B 50 2C 75 18 32 12 00 DC 90    .......P,u.2....
0016C0: E8 00 E4 F0 12 02 11 90 E8 00 E0 F5 2D 90 E8 00    ............-...
0016D0: E0 D3 94 13 50 09 90 E8 00 E0 C3 94 0B 50 06 75    ....P........P.u
0016E0: 1A 05 12 01 6B 12 01 4D 22 90 E1 02 E0 44 01 90    ....k..M"....D..
0016F0: E1 02 F0 90 E1 03 E0 54 01 FF 7E 00 EF 70 10 90    .......T..~..p..
001700: E1 03 E0 44 01 90 E1 03 F0 75 18 14 12 00 DC 90    ...D.....u......
001710: E1 03 E0 44 04 90 E1 03 F0 75 18 1E 12 00 DC 90    ...D.....u......
001720: E1 03 E0 54 FE 90 E1 03 F0 75 18 3C 12 00 DC 90    ...T.....u.<....
001730: E1 03 E0 44 01 90 E1 03 F0 C2 01 22 D2 96 90 E1    ...D......."....
001740: 03 E0 54 F7 90 E1 03 F0 D2 97 90 F0 03 E4 F0 90    ..T.............
001750: F0 01 E4 F0 75 18 14 12 00 DC 75 41 00 75 40 00    ....u.....uA.u@.
001760: 90 E1 03 E0 54 FD 90 E1 03 F0 C2 0B 75 4A 01 75    ....T.......uJ.u
001770: 49 00 AE 49 AF 4A E5 46 BE 00 03 9F 50 03 02 18    I..I.J.F....P...
001780: 57 75 48 01 75 47 00 AE 47 AF 48 74 08 C3 9F 74    WuH.uG..G.Ht...t
001790: 07 9E 40 0E 78 48 74 01 26 F6 50 04 18 E4 36 F6    ..@.xHt.&.P...6.
0017A0: 50 E5 90 E1 01 E0 FE 90 E1 01 E0 5E 54 01 60 02    P..........^T.`.
0017B0: D2 0B 90 E8 05 E4 F0 12 02 11 90 E8 00 E0 F5 31    ...............1
0017C0: 90 E8 00 E4 F0 12 02 11 90 E8 00 E0 C3 94 02 50    ...............P
0017D0: 27 75 18 14 12 00 DC 90 E8 00 E4 F0 12 02 11 90    'u..............
0017E0: E8 00 E0 C3 94 02 50 10 90 E1 03 E0 54 DF 90 E1    ......P.....T...
0017F0: 03 F0 75 1A 02 12 01 6B E5 36 24 02 F5 36 12 02    ..u....k.6$..6..
001800: 4C E5 22 B4 04 03 20 0B 02 80 16 AE 49 AF 4A 74    L."... .....I.Jt
001810: 07 BE 00 03 9F 50 0A 90 E1 03 E0 54 FE 90 E1 03    .....P.....T....
001820: F0 AE 49 AF 4A 74 25 BE 00 03 9F 50 19 20 94 0C    ..I.Jt%....P. ..
001830: 90 E1 03 E0 54 EF 90 E1 03 F0 80 0A 90 E1 03 E0    ....T...........
001840: 44 10 90 E1 03 F0 78 4A 74 01 26 F6 50 04 18 E4    D.....xJt.&.P...
001850: 36 F6 40 03 02 17 72 90 E1 03 E0 44 02 44 08 90    6.@...r....D.D..
001860: E1 03 F0 75 18 FF 12 00 80 90 CC 00 E0 54 40 60    ...u.........T@`
001870: 08 75 19 02 12 00 80 12 03 04 80 FB 22 90 E1 03    .u.........."...
001880: E0 44 10 90 E1 03 F0 75 18 09 12 01 10 D2 02 75    .D.....u.......u
001890: 18 64 12 00 DC 75 46 01 E5 46 D3 94 3C 50 19 75    .d...uF..F..<P.u
0018A0: 18 0A 12 00 DC 12 03 04 A2 94 82 94 50 02 80 0E    ............P...
0018B0: 78 46 74 01 26 F6 50 E0 90 E1 03 E0 54 EF 90 E1    xFt.&.P.....T...
0018C0: 03 F0 12 01 4D 22 D2 08 75 18 05 12 01 10 75 18    ....M"..u.....u.
0018D0: 0A 12 00 DC D2 97 75 18 0C 12 00 DC 90 E1 03 E0    ......u.........
0018E0: 44 20 54 FD 90 E1 03 F0 75 18 0C 12 00 DC 90 E1    D T.....u.......
0018F0: 03 E0 54 F7 90 E1 03 F0 75 48 00 75 47 00 E5 48    ..T.....uH.uG..H
001900: C3 94 C8 50 07 E5 47 C3 94 48 40 02 80 2F 05 48    ...P..G..H@../.H
001910: 90 E8 00 E4 F0 75 18 01 12 00 DC 12 02 11 90 E8    .....u..........
```

```
001920: 00 E0 F5 47 E5 47 C3 94 02 50 10 90 E1 03 E0 54    ...G.G...P.....T
001930: DF 90 E1 03 F0 75 1A 02 12 01 6B 80 C1 90 E1 03    .....u....k.....
001940: E0 44 02 90 E1 03 F0 75 18 0C 12 00 DC 90 E1 03    .D.....u........
001950: E0 44 08 90 E1 03 F0 90 CC 00 E0 54 20 60 06 12    .D.........T `..
001960: 16 E9 02 19 EC 75 18 64 12 00 DC 90 E8 00 E4 F0    .....u.d........
001970: 12 02 11 E5 47 C3 94 02 40 09 90 E8 00 E0 C3 94    ....G...@.......
001980: 02 50 10 90 E1 03 E0 54 DF 90 E1 03 F0 75 1A 02    .P.....T.....u..
001990: 12 01 6B E5 47 C3 94 4B 40 0E 90 E8 00 E0 FE E5    ..k.G..K@.......
0019A0: 47 C3 94 19 C3 9E 40 02 80 18 75 18 02 12 01 10    G.....@...u.....
0019B0: 75 18 32 12 00 DC D2 01 20 02 03 12 1B 7D 12 01    u.2..... ....}..
0019C0: 4D 22 30 0B 05 C2 02 18 DC 75 18 05 12 00 80       M"0......u.....
0019D0: 90 CC 00 E0 54 20 60 08 90 CC 00 E0 54 20 70 02    ....T `.....T p.
0019E0: 80 05 12 16 E9 80 05 12 03 04 80 E4 90 07 98 12    ................
0019F0: 1F 71 90 E0 10 E4 F0 A3 F0 D2 96 D2 97 90 F0 03    .q..............
001A00: E4 F0 90 F0 01 E4 F0 C2 08 90 E1 03 E0 54 F7 90    .............T..
001A10: E1 03 F0 75 2D 0F A2 05 40 06 E5 43 44 80 F5 43    ...u-...@..CD..C
001A20: E5 43 90 C4 04 F0 C2 04 75 18 0A 12 00 DC 90 E1    .C......u.......
001A30: 03 E0 54 FD 90 E1 03 F0 75 47 01 75 46 00 AE 46    ..T.....uG.uF..F
001A40: AF 47 74 2C C3 9F 74 01 9E 50 03 02 1A E7 74 01    .Gt,..t..P....t.
001A50: 52 07 7E 00 EF 4E 70 06 75 18 01 12 00 DC 90 E1    R.~..Np.u.......
001A60: 01 E0 FE 90 E1 01 E0 5E 54 01 60 02 D2 0B 30 94    .......^T.`...0.
001A70: 02 80 74 90 E8 03 E4 F0 12 02 11 90 E8 00 E0 C3    ..t.............
001A80: 94 E1 50 06 90 E0 10 12 00 0E 90 E0 10 E0 FE A3    ..P.............
001A90: E0 FF 74 78 BE 00 03 9F 50 06 75 1A 10 12 01 6B    ..tx....P.u....k
001AA0: AE 46 AF 47 74 19 BE 00 03 9F 50 03 20 0B 02 80    .F.Gt.....P. ...
001AB0: 0F E5 22 B4 04 0A 90 E1 03 E0 54 FE 90 E1 03 F0    .."......T......
001AC0: AE 46 AF 47 74 7D BE 00 03 9F 50 0A 90 E1 03 E0    .F.Gt}....P.....
001AD0: 54 EF 90 E1 03 F0 78 47 74 01 26 F6 50 04 1B E4    T.....xGt.&.P...
001AE0: 36 F6 40 03 02 1A 3E 90 E1 03 E0 44 02 44 08 90    6.@...>....D.D..
001AF0: E1 03 F0 22 90 CC 00 E0 54 10 70 36 C2 05 75 37    ..."....T.p6..u7
001B00: 00 20 94 06 E5 43 44 80 F5 43 E5 43 90 C4 04 F0    . ...CD..C.C....
001B10: C2 00 75 34 D7 E5 22 C3 94 02 50 14 E5 35 C3 94    ..u4.."...P..5..
001B20: 32 50 01 22 75 35 00 74 0B 25 22 F5 18 12 01 10    2P."u5.t.%".....
001B30: 80 51 E5 34 D3 94 DC 40 4A 75 34 00 82 00 30 00    .Q.4...@Ju4...0.
001B40: 21 E5 37 C3 94 05 50 10 E5 43 54 7F F5 43 E5 43    !.7...P..CT..C.C
001B50: 90 C4 04 F0 D2 05 05 37 75 34 8C 75 18 04 12 01    .......7u4.u....
001B60: 10 22 E5 43 44 80 F5 43 E5 43 90 C4 04 F0 C2 05    .".CD..C.C......
001B70: 75 35 FA E5 22 C3 94 02 50 09 74 0B 25 22 F5 18    u5.."...P.t.%"..
001B80: 12 01 10 22 20 43 48 45 43 4B 20 20 43 41 42       ..." CHECK  CAB
001B90: 4C 45 20 20 54 52 41 4E 53 46 45 52 54 52 41 4E    LE  TRANSFERTRAN
001BA0: 53 46 45 52 20 43 48 45 43 4B 20 43 41 53 53       SFER CHECK CASS
001BB0: 45 54 54 45 4C 4F 57 20 41 49 52 20 50 52 45 53    ETTELOW AIR PRES
001BC0: 53 55 52 45 20 43 48 45 43 4B 20 43 4F 4E 54       SURE CHECK CONT
001BD0: 41 43 54 53 20 56 41 43 55 55 4D 20 20 20 4C 45    ACTS VACUUM   LE
001BE0: 41 4B 20 20 20 49 4E 53 45 52 54 20 43 41 53 53    AK   INSERT CASS
001BF0: 45 54 54 45 52 45 4C 45 41 53 45 20 20 46 4F 4F    ETTERELEASE  FOO
001C00: 54 53 57 20 20 20 20 20 20 20 53 43 49 53          TSW        SCIS
001C10: 53 4F 52 53 20 20 46 52 41 47 20 20 20 20 4F       SORS  FRAG    O
001C20: 4B 20 20 20 54 52 41 4E 53 46 45 52 4C 4F 57 20    K   TRANSFERLOW
001C30: 20 41 49 52 43 48 45 43 4B 49 4E 47 20 45 52 52     AIRCHECKING ERR
001C40: 4F 52 20 20 45 52 52 4F 52 20 20 20 4D 56 53 20    OR  ERROR   MVS
001C50: 56 31 2E 31 49 52 52 20 4F 50 45 4E 49 2F 41 20    V1.1IRR OPENI/A
001C60: 46 52 41 47 20 4D 55 4C 54 49 20 20 20 20 50 52    FRAG MULTI    PR
001C70: 4F 50 20 20 20 20 49 2F 41 20 20 20 20 20 56 49    OP    I/A     VI
001C80: 54 20 20 20 49 52 52 20 4F 4E 4C 59 88 88 88 A4    T   IRR ONLY....
001C90: 90 98 74 FF 90 C4 00 F0 74 FF 90 C4 01 F0 74 FF    ..t.....t.....t.
001CA0: 90 C4 02 F0 E5 42 44 3F 90 C4 03 F0 22 E5 1E D3    .....BD?...."...
001CB0: 94 1E 50 07 E5 1E C3 94 01 50 07 74 AA 90 C4 02    ..P......P.t....
001CC0: F0 22 75 1F 00 E5 1E D3 94 08 40 16 E5 1F 90 C4    ."u.......@.....
001CD0: 00 12 1F 57 74 00 F0 05 1F E5 1E C3 94 08 F5 1E    ...Wt...........
001CE0: 80 E3 E5 1F C3 94 03 50 13 E5 1E 90 1F 4E 93 FE    .......P.....N..
001CF0: E5 1F 90 C4 00 12 1F 57 EE F0 80 19 E5 1E 90 1F    .......W........
001D00: 4E 93 54 3F FE E5 42 54 C0 4E FE E5 1F 90 C4 00    N.T?..BT.N......
001D10: 12 1F 57 EE F0 05 1F E5 1F C3 94 04 50 20 E5 1F    ..W.........P ..
001D20: B4 03 0C E5 42 54 C0 44 3F 90 C4 03 F0 80 0B E5    ....BT.D?.......
001D30: 1F 90 C4 00 12 1F 57 74 FF F0 05 1F 80 D9 22 90    ......Wt......".
001D40: E8 00 E4 F0 75 1F 14 75 1E 00 75 1E 1F 75 1F 55    ....u..u..u..u.U
001D50: 75 1F 14 75 1E 00 75 1E 1F 75 1F 55 30 92 06 75    u..u..u..u.U0..u
001D60: 1A 08 12 01 6B 75 1F 01 75 1E 00 AE 1E AF 1F 74    ....ku..u......t
001D70: 28 BE 00 16 9F 40 13 30 92 02 80 14 78 1F 74 01    (....@.0....x.t.
001D80: 26 F6 50 04 18 E4 36 F6 50 E1 75 1A 0B 12 01 6B    &.P...6.P.u....k
```

What is claimed is:

1. An apparatus for sensing the proximity to a cassette receptacle of a cassette having a vacuum port and for drawing said cassette into a position in said cassette receptacle where said cassette may be evacuated, comprising:

a cassette receptacle for receiving said cassette;
proximity sensing means for sensing that a cassette has been partially pushed into said cassette receptacle;
means for supplying vacuum at a stationary vacuum supply port in said cassette receptacle;
means coupled to said sensing means for physically engaging said cassette and applying force to said cassette to place said cassette in a final position in said cassette receptacle with said vacuum port engaged in fluid communication and in sealing engagement with said vacuum supply port until the cassette is removed from the receptacle.

2. The apparatus of claim 1 wherein said cassette has a projecting portion and said means for sensing includes a switch with an actuator arm which is placed so as to contact said projecting portion when said cassette is partially in said cassette receptacle.

3. The apparatus of claim 2 wherein said means for physically engaging said cassette includes a pneumatic piston coupled to a mechanical linkage which engages said projecting portion of said cassette and a computer means coupled to said switch and to said pneumatic piston for reading the position of said switch and for causing air pressure to be applied to said pneumatic piston so as to cause said pneumatic piston to move thereby moving said mechanical linkage in such a way as to draw said cassette into sealing engagement with said vacuum supply port in said cassette receptacle.

4. The apparatus of claim 3 wherein said cassette is capable of being evacuated and has at least one vacuum port surrounded by a vacuum seal through which said evacuation can be accomplished, and wherein said receptacle has at least one vacuum supply port which mates with said vacuum port in said cassette when said cassette is fully engaged with said cassette receptacle, said vacuum supply port being surrounded by a vacuum seal so as to engage said vacuum seal on said cassette in a sealing relationship when said cassette is fully engaged with said cassette receptacle.

5. The apparatus of claim 4 wherein said proximity sensing means includes a switch having at least two states and an arm which is engaged by said cassette when said cassette is pushed into partial engagement with said cassette receptacle, thereby causing said switch to change from a first state to a second state, and said means for engaging said cassette further includes logic means coupled to said proximity sensing means for reading the state of said switch and for causing a solenoid operated valve coupled between a pneumatic air pressure supply and said pneumatic piston to gate pressurized air through to said pneumatic piston to move said piston in such a way as to cause said linkage to engage the projecting portion of said cassette and pull said cassette into seated position thereby sealing said vacuum seal.

6. The apparatus of claim 5 further comprising a cassette eject switch having first and second states, said first state for indicating when the cassette is to be ejected and wherein said logic means includes means for examining the current state of said cassette eject switch and ejecting said cassette when said switch has been actuated to said first state.

7. The apparatus of claim 6 wherein said means to examine the current state of said cassette eject switch and eject said cassette includes means for venting the pressure in said pneumatic piston to atmospheric pressure and includes an eject pneumatic piston and an extension of said eject pneumatic piston and valve means to gate pressurized air into said eject pneumatic piston after said pneumatic piston has been vented to atmosphere and after said cassette eject switch has been actuated to said first state in order to cause said extension to contact said cassette and push said cassette out of said cassette receptacle.

8. The apparatus of claim 7 wherein said logic means further includes means for testing the integrity of the sealing relationship between said vacuum seal on said cassette and said vacuum seal around said vacuum supply port after said cassette has been fully engaged in said cassette receptacle including means to check whether a predetermined level of vacuum can be achieved and means for determining whether a predetermined level of vacuum can be maintained for a predetermined interval in said cassette with no further evacuation of said cassette.

9. The apparatus of claim 8 wherein said surgical instrument includes a vacuum generation system for generating vacuum at a level controlled by a footswitch position sensor and wherein said logic means further includes means for insuring that the footswitch is not depressed before determining whether said cassette eject switch has been actuated to said first state.

* * * * *